United States Patent
Huang

(10) Patent No.: US 7,365,158 B2
(45) Date of Patent: Apr. 29, 2008

(54) PR-DOMAIN CONTAINING NUCLEIC ACIDS, POLYPEPTIDES, ANTIBODIES AND METHODS

(75) Inventor: Shi Huang, San Diego, CA (US)

(73) Assignee: The Burnham Institute, La Jolla, CA (US)

( * ) Notice: Subject to any disclaimer, the term of this patent is extended or adjusted under 35 U.S.C. 154(b) by 612 days.

(21) Appl. No.: 10/377,079

(22) Filed: Feb. 28, 2003

(65) Prior Publication Data

US 2003/0236395 A1 Dec. 25, 2003

Related U.S. Application Data

(63) Continuation of application No. 09/389,956, filed on Sep. 3, 1999, now Pat. No. 6,586,579.

(51) Int. Cl.
- *C07K 14/00* (2006.01)
- *C07H 21/04* (2006.01)
- *C12N 15/00* (2006.01)
- *C12N 5/02* (2006.01)

(52) U.S. Cl. .................. 530/350; 435/6; 435/69.1; 435/320.1; 435/325; 536/23.5

(58) Field of Classification Search ............... 536/23.5; 435/6, 69.1, 320.1, 325; 530/350
See application file for complete search history.

(56) References Cited

OTHER PUBLICATIONS

Burgess et al., The Journal of Cell Biology, 111:2129-2138, 1990.*
Huang et al 1998, J.B.C. 273 (26), 15933-15939.*
Database Uniprot_trembl, Accession No. Q8COV8, Seq. ID No. 2, 18, 64, 30, and 32.*
Alexandra Chittka and Moses V. Chao vol. 96, Issue 19, 10705-10710, Sep. 14, 1999.*
Yang and Huang 1999 ,Genomics 61:319-325.*
Bowie et al (Science, 1990, 257:1306-1310).*
Burgess et al ( J of Cell Bio. 111:2129-2138, 1990).*
Lazar et al (Molecular and Cellular Biology, 1988, 8:1247-1252).*
Scott et al (Nature Genetics 1999, 21:440-443).*
Bork (Genome Research, 2000, 10:398-400).*

* cited by examiner

*Primary Examiner*—Shanon Foley
*Assistant Examiner*—Padma Baskar
(74) *Attorney, Agent, or Firm*—McDermott Will & Emery LLP

(57) ABSTRACT

The invention provides an isolated PR Family Member (PFM) nucleic acid molecule that contains a PFM PR domain nucleotide sequence, a PFM ZF domain nucleotide sequence, or a modification thereof. The invention also provides an isolated PFM nucleic acid molecule that contains a nucleotide sequence that encodes a PFM PR domain polypeptide, or that encodes a PFM ZF domain polypeptide, or that encodes an immunologically equivalent modification thereof. Also provided are isolated PFM oligonucleotides. The invention also provides methods for detecting a PFM nucleic acid molecule in a sample. Further provided is a method of modulating cell growth by expressing an encoded PFM polypeptide in the cell. Also provided is an isolated PFM polypeptide, containing a PFM PR domain amino acid sequence, or a PFM ZF domain amino acid sequence, or a modification thereof. The invention also provides an isolated PFM peptide, containing at least 8 contiguous amino acids of a PFM polypeptide. Also provided is an antibody or antigen binding fragment thereof, which specifically binds a PFM polypeptide. Further provided is a method for detecting PFM polypeptide in a sample, by contacting the sample with a PFM antibody and detecting specifically bound antibody.

9 Claims, 23 Drawing Sheets

PFM1 nt

```
   1 attacaggtg taaatcacca cacctggct gctttatttt atagcacgtg accctggaac
  61 gcaaaccctg atgcctgtcc ccaccaccg agcgctcctt ctctgatatt ggccccaagc
 121 cgatgcatca caggatgaat gaaaatgaac ctgagtccag tggggatggc gcagctgact
 181 tcatcctctg tgagcaatgc cttgccagtc tcaggaagtc acctggatt ggctgcctca
 241 cccactcaca gtgccatccc tgccccaggc ctcccagtgg caattccaaa cctggtccc
 301 tccctgagct ctctgccttc tgctctgtct ttaatgctac caatgggtat tgggatcga
 361 ggggtgatgt gtgggttacc tgaaagaaac tacaccctac ctccaccacc ttaccctcac
 421 ctgagagagca gttattcag aaccattcta cctggcatt tatcttattt agctgacaga
 481 ccacctccac agtacatcca cctaactct ataaatgttg atggtaatac agcattatct
 541 atcaccaata acccttcagc actagatccc tatcagtcca atggaaaatgt tggattagaa
 601 ccaggcattg tttcaataga ctctcgctct gtgaacacac atggtgccca aagtcttcat
 661 cccagtgatg gccatgaggt ggccttggac acagcaatca ctatggagaa cgtttctagg
 721 gttaccagcc caatttcgac agatgaatg gcagaggagc ttacgatgga cggtgttgca
 781 ggcgagcatt cccaaatccc aaatgctcc agaagtcatg aacctctgtc tgtggattct
 841 gtgagcaaca acctgctgta agacgctgta ggacatggtg gtgtgataccc catgcatggg
 901 aatggcctgg agctccctgt ggtcatggag acagaccaca ttgcaagtcg ggtcaatgc
 961 atgtctgaca gtgccctcag tgactccatt cacactgtgg ccatgagcac caactctgta
1021 agcgtggcac tctctacctc acacaacctt gcctccctag aatctgtttc cctccatgaa
1081 gttggcctca gcctagaacc tgtggctgtc tcctccatca cccaggaggt tgctatgggg
1141 acaggtcatg tagatgtatc ttcagacagt ctttcttttg tatcaccttc actgcaaatg
1201 gaagactcca attcaaacaa ggagaacatg gcaaccttgt ttacaatttg gtgtactctg
1261 tgtgaccgcg cctatccctc ggactgtccc gaacatggac cagtgacttt tgttcctgac
1321 actccaatag agagcagagc aaggctttct ctcccaaagc agcttgttct ccgtcagtca
1381 attgtgggag cagaagttgg tgtatggact ggagaaacca ttccctgtgcg gacttgcttt
1441 ggacctctaa ttggcagca gagtcactcc atggaagtag cagaatggac agacaaggca
1501 gttaaccata tctggaagat ataccacaat ggtgtcctag aatttcgcat cattacaact
1561 gatgaaaatg aatgtaattg gatgatgttt gtgcgcaaag ccaggaaccg ggaagagcag
1621 aatttgtgg cttatcctca tgatggaaaa atcttttcct gcacctcaca agatatcct
1681 cctgaaaatg aactgctttt ttattatagc cgagattatg ctcaacagat tggtgttcct
1741 gaacacccag atgtgcatct ctgtaactgt gcaaggagt gcaattctta cacagagttc
1801 aaagcccatc tgaccagcca catccataac catcttccta ccaggggaca tagcggcagc
1861 atcgggccaa gtcacacgga agaaggaag tggaagtgct caatgtgccc ccaagctttt
```

FIGURE 1A

```
1921 atctctcctt ccaaacttca tgtctacttt atgggtcaca tgggtatgaa gccccacaag
1981 tgtgatttct gtagcaaggc gtttagtgat cccagcaacc tgcggaccca cctcaagata
2041 catacaggtc agaagaacta caggtgtacc ttgtgtgaca agtcttcac ccagaaggct
2101 cacctgggag tccacatggt tatccacact gggagaaga atcttaagtg tgattactgt
2161 gacaagttgt ttatgcggag gcaggacctc aagcagcacg tgctcatcca cactcaagaa
2221 cgccagatca agtgtcccaa gtgtgataag ctgttcttga gaacaaatca cttaaagaag
2281 catctcaatt ctcatgaagg aaaacgggat tatgtctgtg aaaaatgtac aaaggcttat
2341 ctaaccaaat accatctcac ccgccacctg aaaacctgca aagggcccac ctccagttcg
2401 tcagcaccag aggaggaaga agaggatgac tcagaagagg aagatctagc agactctgtg
2461 gggacagaag actgtaggat taacagtgct gtgtattcag cggatgagtc tcttcctgca
2521 cataaataaa aggaaaggaa ccggcatttc tggttttat tgcaaatgga aaatacaca
2581 tacccagtta tctactataa tggtttttat ataaaatggt tctgatttat tttcagccag
2641 taatcaaaac agactgggaa tgaataaagc acttacagaa gagtctctaa tgaaaacact
2701 ttaaaacaga ttgggaaaac tgagcatgtg tcctatttta agtggtggac tgggagggaa
2761 gtgtaacttc tgaggcttta ttacatgata atctgggaga tgcatttatc tgaatcaaag
2821 ctgccttctg ctcaaacaaa tcagatttat ttcacattct tccattattc cattttcctg
2881 ctgtcctgtg gacttggtaa cattctaaac ggtccttgcc ccatagccat ctgattgct
2941 gatagtgttt tatgcagact cttgtgactt atactcacca cagaatggat tgggacacag
3001 cagcataagt gtgctacttg gcagctagta agtttaaagc aggacctgcc ttaactgctc
3061 ctggccactt ggaagtttag ggtagatctt gtttccaaa gtttcggcag gtgctggagg
3121 gcaaataaaa aagcagcagt cagtcagtag tcagtgatgg agagaacaag aggagagatg
3181 cctggcctct gcccaagaaa ttagctttga tgggctcctg ctccagtcac ctggttattg
3241 taacgtggag atctttgtag gttagacat ggctccctgt agcccagcaa catccagcca
3301 ttcagacaaa ggggcctgg agatacagag agcccaata atgcctgctg gattgtctcc
3361 tgatgagtac atgtggactc acctgaggaa gggaaggaag ggaataatct tttatgtttc
3421 attaccttta tgaaaagtgt accttgtctg ccaactcaa ataacattat ttaatgcatg
3481 tgcaaagtta ggtcttccca gttgtctcag tgctgaggaa cctcatcaga gaagcatgga
3541 agatgccaaa ggattttggg aaggtaaaga aggctgaata gtgaccacat gggcctgttt
3601 tcagggtccc agcttagtta agtcaccat gcacctgttc attgtgtctc ccgtgcacat
3661 ccagcgtttc tcagaagcag acccaccctt aagttgacag gattgatgga acatgctctc
3721 ctgctcaagg cacaacctct gggctggagt agaggactct gttgggaagg tttgctgct
3781 aatgtattta tggaatgaat gtatttcatt caaatctgta ttcctctagg aaggattaaa
3841 attaaactt tttaaaatac cggaaaaaaa aaaaaaaaaa aaaaaaaaaa aaaaaaaaaa
3901 aa
```

FIGURE 1A (CONTINUED)

PFM1 aa

```
  1 MKMNLSPVGM AQLTSSSVSN ALPVSGSHLG LAASPTHSAI PAPGLPVAIP
 51 NLGPSLSSLP SALSLMLPMG IGDRGVMCGL PERNYTLPPP PYPHLESSYF
101 RTILPGILSY LADRPPPQYI HPNSINVDGN TALSITNNPS ALDPYQSNGN
151 VGLEPGIVSI DSRSVNTHGA QSLHPSDGHE VALDTAITME NVSRVTSPIS
201 TDGMAEELTM DGVAGEHSQI PNGSRSHEPL SVDSVSNNLA ADAVGHGGVI
251 PMHGNGLELP VVMETDHIAS RVNGMSDSAL SDSIHTVAMS TNSVSVALST
301 SHNLASLESV SLHEVGLSLE PVAVSSITQE VAMGTGHVDV SSDSLSFVSP
351 SLQMEDSNSN KENMATLFTI WCTLCDRAYP SDCPEHGPVT FVPDTPIESR
401 ARLSLPKQLV LRQSIVGAEV GVWTGETIPV RTCFGPLIGQ QSHSMEVAEW
451 TDKAVNHIWK IYHNGVLEFC IITTDENECN WMMFVRKARN REEQNLVAYP
501 HDGKIFFCTS QDIPPENELL FYYSRDYAQQ IGVPEHPDVH LCNCGKECNS
551 YTEFKAHLTS HIHNHLPTQG HSGSIGPSHS KERKWKCSMC PQAFISPSKL
601 HVYFMGHMGM KPHKCDFCSK AFSDPSNLRT HLKIHTGQKN YRCTLCDKSF
651 TQKAHLGVHM VIHTGEKNLK CDYCDKLFMR RQDLKQHVLI HTQERQIKCP
701 KCDKLFLRTN HLKKHLNSHE GKRDYVCEKC TKAYLTKYHL TRHLKTCKGP
751 TSSSSAPEEE EEDDSEEEDL ADSVGTEDCR INSAVYSADE SLSAHK
```

FIGURE 1B

PFM2 nt

```
   1 cggccgccgg cccgggaaaa tgctgggcat gtacgtgccg gacaggttct
  51 ccctgaagtc ctcccgggtt caggacggca tggggctcta cacggcccgc
 101 agagtgcgaa agggtgaaaa gttcggaccc tttgctggag agaagagaat
 151 gcctgaagac ttggatgaaa aatggattac aggttgatgt gggaggttcg
 201 tgggagtaag ggagaagttt tgtacatttt ggatgctacc aacccacggc
 251 actccaactg gcttcgcttc gttcatgagg caccatctca ggagcagaag
 301 aacttggctg ccattcaaga aggagaaaac atttctatt tggcagttga
 351 agatatagaa acagacacgg agcttctgat tggctacctg gatagtgaca
 401 tggaggctga ggaggaagaa cagcaaatta tgacagtcat caaagaaggg
 451 gaagttgaaa attctagaag acaatcaaca gcgggcagaa aagatcgcct
 501 tggctgtaaa gaggactatg cttgtcctca atgtgaatcg agtttacca
 551 gtgaggatat tcttgctgag catctccaga cattgcacca gaaacccaca
 601 gaggagaaag aatttaagtg caagaactgt gggaagaaat tcccagttaa
 651 gcaggctttg caaagacatg ttcttcagtg cacagcgaaa agcagtctga
 701 aggagtcttc gcgaagtttt cagtgctctg tttgcaattc ttccttcagt
 751 tcagcatcga gttttgagca gcaccaggag acttgccggg gggatgccaa
 801 gtttgtgtgc aaggctgaca gctgtggaaa gaggctgaag agcaaggatg
 851 ccctgaaaag acaccaggaa aatgtccaca ctggagatcc taagaaaaag
 901 cttatatgtt cagtgtgcaa taaaagtgt tcttcagcat caagcctaca
 951 ggaacataga aagattcatg agatatttga ttgtcaagaa tgtatgaaga
1001 aatttatttc agctaatcag ctaaaacgtc atatgatcac ctcgtgccta
1051 attcttgggc tcgag
```

FIGURE 2A

PFM2 aa

```
  1 MDYRLMWEVR GSKGEVLYIL DATNPRHSNW LRFVHEAPSQ EQKNLAAIQE
 51 GENIFYLAVE DIETDTELLI GYLDSDMEAE EEEQQIMTVI KEGEVENSRR
101 QSTAGRKDRL GCKEDYACPQ CESSFTSEDI LAEHLQTLHQ KPTEEKEFKC
151 KNCGKKFPVK QALQRHVLQC TAKSSLKESS RSFQCSVCNS SFSSASSFEQ
201 HQETCRGDAK FVCKADSCGK RLKSKDALKR HQENVHTGDP KKKLICSVCN
251 KKCSSASSLQ EHRKIHEIFD CQECMKKFIS ANQLKRHMIT SCLILGLE
```

FIGURE 2B mPFM2a nt

```
   1 tttcctcctc ccggccgccc caggcccgca ccccatctcc acgtgcggcg
  51 cctccggagc gcggccgagc cacggaggat gctgggcatg tacgtaccag
 101 acaggttcgc cctgaagtcg tcccgggtcc aggacgggat ggggctctac
 151 acggcccgcc gcgtgcgcaa gggtgaaaaa tttggaccct tcgctgggga
 201 gaagcgaatg cctgaagact tggatgaaaa tatggactac agactgatgt
 251 gggtggtacg tgggagcaag ggagaagttc tgtatatttt ggatgctacc
 301 aacccaagac actccaactg gcttcgcttt gttcacgagg caccatctca
 351 ggagcggaag aacctggctg ccattcaaga aggagaaaaa tatttctact
 401 tggcagttga tgatatagaa acagatacag agcttttgat tggctacctg
 451 gacagtgatg tggaggcaga ggaggaggag caacaagctc tgaccatgac
 501 caaagaaggc aaagttgacc actctaaggg acagttggca gctggaagta
 551 aaggtactgc atcttcgttt ggtgatctga aggaagagac atttgaagag
 601 gaaggtcacc ttggctgtga agaggacttt gcctgtccac agtgtgaatc
 651 gagcttttcc agtgaggaag tccttactga gcaccttcag agcttgcacc
 701 agaagcccac aggggagaaa gagttcaaat gcgagaactg cgggaagaaa
 751 ttccctgtga ggcaggcctt gcagagacat gttcttcagt gcacagcgaa
 801 aagcagtctg aaggagtctt cgcgaagttt tcagtgctct gtttgcaatt
 851 cttccttcag ttcagcatcg agttttgagc agcaccagga gacttgccgg
 901 ggggatgcca agtttgtgtg caaggctgac agctgtggaa agaggctgaa
 951 gagcaaggat gccctgaaaa gacaccagga aaatgtccac actggagatc
1001 ctaagagaaa actcatatgc tcggtgtgca atagaaaatg tacctcagtg
1051 tcaagcctgc aggagcacag gaagattcat gagatatttg attgtcaaga
1101 atgtatgaaa aagtttattt ctgctaatca gctgaagcgt cacatgatta
1151 cccactcaga aaagcggcct tataactgtg agatctgtaa caagtccttc
1201 aagaggctcg atcaagtggg cgcccacaaa gtgatccaca gtgaggacaa
1251 accctaccag tgcaagctct gtggcaaggg ctttgctcac agaaacgttt
1301 acaagaacca caagaagacc cactccgagg agagaccttt ccagtgtgat
1351 gcatgtaaag ccttgttccg cacgcccttt tctctgcaga gacacctgtt
1401 aatccacaac agtgagagga cttttaagtg tcaccactgt gatgccacat
1451 ttaaaaggaa ggatacatta aacgttcatg cccaggtggt ccatgaaaga
1501 cacaagaagt accgatgtga gctgtgcaat aaggcctttg tcacaccttc
1551 agtgcttagg agtcataaga agtcacacac aggagaaaag gagaaagtct
1601 gcccatattg tggccagaaa tttgccagca gtgggaccct gagagttcac
1651 atccggagcc acacaggtga gcgccctat caatgcccgt actgtgaaaa
1701 aggtttcagt aaaaatgacg gactgaagat gcacattcgt actcacacca
1751 gggagaagcc ctaccagtgc tcagagtgca gcaaggcctt cagccagaag
1801 cggggcctcg atgaacacaa gaggacacac acaggagaaa agccttttca
1851 gtgtgacgta tgtgacttgg cttttagcct gaagaaaatg cttattcgac
1901 acaagatgac acacaatcct aaccgtccga tggcagagtg ccatttctgc
1951 cataagaagt ttacaagaaa tgactacctc aaagtgcaca tggacaacat
2001 ccatggggta gctgacagct aagaggagcg gcaaggaacc acaccatgtg
2051 aaagagcttc tactatgaat cccagattct tctcacctga tcggcttaac
2101 agaaatagcc acaaggatt cattgatctg acagtgttta tgtgcctatc
2151 tttgtaatct atagatgcaa aaaaaatcct tttaccaaaa ataaattcaa
2201 aatagaaaac aataatactt tgtagattac agagtattct ggctgattaa
2251 aaattaaatc ag
```

FIGURE 3A mPFM2a aa

```
  1 MLGMYVPDRF ALKSSRVQDG MGLYTARRVR KGEKFGPFAG EKRMPEDLDE
 51 NMDYRLMWVV RGSKGEVLYI LDATNPRHSN WLRFVHEAPS QERKNLAAIQ
101 EGEKYFYLAV DDIETDTELL IGYLDSDVEA EEEEQQALTM TKEGKVDHSK
151 GQLAAGSKGT ASSFGDLKEE TFEEEGHLGC EEDFACPQCE SSFPSEEVLT
201 EHLQSLHQKP TGEKEFKCEN CGKKFPVRQA LQRHVLQCTA KSSLKESSRS
251 FQCSVCNSSF SSASSFEQHQ ETCRGDAKFV CKADSCGKRL KSKDALKRHQ
301 ENVHTGDPKR KLICSVCNRK CTSVSSLQEH RKIHEIFDCQ ECMKKFISAN
351 QLKRHMITHS EKRPYNCEIC NKSFKRLDQV GAHKVIHSED KPYQCKLCGK
401 GFAHRNVYKN HKKTHSEERP FQCDACKALF RTPFSLQRHL LIHNSERTFK
451 CHHCDATFKR KDTLNVHAQV VHERHKKYRC ELCNKAFVTP SVLRSHKKSH
501 TGEKEKVCPY CGQKFASSGT LRVHIRSHTG ERPYQCPYCE KGFSKNDGLK
551 MHIRTHTREK PYQCSECSKA FSQKRGLDEH KRTHTGEKPF QCDVCDLAFS
601 LKKMLIRHKM THNPNRPMAE CHFCHKKFTR NDYLKVHMDN IHGVADS
```

FIGURE 3B mPFM2b nt

```
   1 tttcttacgt accagacagg ttcgccctga agtcgtcccg ggtccaggac
  51 gggatggggc tctacacggc ccgccgcgtg cgcaagggtg aaaaatttgg
 101 acccttcgct ggggagaagc gaatgcctga agacttggat gaaaatatgg
 151 actacagact gatgtgggag gtacgtggga gcaagggaga agttctgtat
 201 attttggatg ctaccaaccc aagacactcc aactggcttc gctttgttca
 251 cgaggcacca tctcaggagc ggaagaacct ggctgccatt caagtgagcc
 301 tgttggttca tatttgtaca atgcactgtg agagtaatgg attaatttat
 351 aactctgctc catgtcttca atttatttcc ctgtgatcag cttcatataa
 401 cagtatctaa ctcataaaag caaagaaatc atgtagtcgg catatgcagg
 451 aaaacgcaac tgaactgtca gctaaaacca gacttctggc tttattggaa
 501 ttcttggggg aatgaattac acggtctgat actgtgcttg gcagagcttg
 551 cgttcaagta ctttgatttc cttcagtgaa tgtttttttga tagcagtttg
 601 gtttgctagt tgctttggat cgtcttactc tgctgtgggt tattctttga
 651 gaaaggaaaa aaaaaaaaaa aaaaaaaaaa aaaaaaaaaa aaaaaaaaaa
 701 taaagtgcag aagaagtcaa ggagccatgg ctgacataaa catgaaggga
 751 agcacagaac aactgcctac actgttctag attgctcatc tctatgtgat
 801 aattgctttt aggaacttat aatgtagaaa ttttctgact agtatactga
 851 tttcacttaa gtctcaagga actatagtga ggaaacatca cagcattaag
 901 tttaatccaa caataataca gttgtctgct atgtaatttt ctatcctcag
 951 ctaagtaatt tctctgttaa tacaagtgtt atagccgggt ggtggtggtg
1001 cgcgccttta atctcagcac ttgggagaca gaggcaggcg gatttctgag
1051 ttcgaggcca gctggtctca caaagtgagt tccaggacag ccagcagggc
1101 tataccaaga aaccctgtct tgaaaa
```

FIGURE 4A mPFM2b aa

```
  1 MGLYTARRVR KGEKFGPFAG EKRMPEDLDE NMDYRLMWEV RGSKGEVLYI
 51 LDATNPRHSN WLRFVHEAPS QERKNLAAIQ VSLLVHICTM HCESNGLIYN
101 SAPCLQFISL
```

FIGURE 4B

PFM3a nt

```
   1 aaagcgcagc agcccacggc ggttgagtcg ggcgcccagg tccgtccgca
  51 ctctcgcgcc ctccgcgggc ctcccaattt tctcgcttgc aggtcgggag
 101 gtttccgggc ggcacaatct ctaggactct cctcccgcgc tgctcagggg
 151 catgtagcgc acgcagggcg cacactctcg cgcacccgca cgctcaccga
 201 gacacccgcg ctggctggtc tctcggccct gccggtgtcg cagctgccgg
 251 tgttcgcgcc tctagccgcc gctgccgtcg ccgccgagcc gctgccccccc
 301 aaggaactgt gcctcggcgc cacctccggc cccgggcccg tcaagtgcgg
 351 tggtggtggc ggcggcggcg gggagggtcg cggcgccccg cgcttccgct
 401 gcagcgcaga ggagctggac tattacctgt atggccagca gcgcatggag
 451 atcatcccgc tcaaccagca caccagcgac cccaacaacc gttgcgacat
 501 gtgcgcggac aaccgcaacg gcgagtgccc tatgcatggg ccactgcact
 551 cgctgcgccg gcttgtgggc accagcagcg ctgcggccgc cgcgccccg
 601 ccggagctgc cggagtggct gcgggacctg cctcgcgagg tgtgcctctg
 651 caccagtact gtgcccggcc tggcctacgg catctgcgcg gcgcagagga
 701 tccagcaagg cacctggatt ggacctttcc aaggcgtgct tctgccccca
 751 gagaaggtgc aggcaggcgc cgtgaggaac acgcagcatc tctgggagat
 801 atatgaccag gatgggacac tacagcactt tattgatggt ggggaaccta
 851 gtaagtcgag ctggatgagg tatatccgat gtgcaaggca ctgcggagaa
 901 cagaatctaa cagtagttca gtacaggtcg aatatattct accgagcctg
 951 tatagatatc cctaggggca ccgagcttct ggtgtggtac aatgacagct
1001 atacgtcttt ctttgggatc cctttacaat gcattgccca ggatgaaaac
1051 ttaaatgtcc cttcaacggt aatggaagcc atgtgcagac aagacgccct
1101 gcagcccttc aacaaaagca gcaaactcgc cctaccacc cagcagcgct
1151 ccgttgtttt cccccagact ccgtgcagca ggaacttctc tcttctggat
1201 aagtctgggc ccattgaatc aggatttaat caaatcaacg tgaaaaacca
1251 gcgagtcctg gcaagcccaa cttccacaag ccagctccac tcggagttca
1301 gtgactggca tctttggaaa tgtgggcagt gctttaagac tttcacccag
1351 cggatcctct tacagatgca cgtgtgcacg cagaacaccg acagaccccta
1401 ccaatcgggc cactgctccc agtccttttc ccagccttca gaactgagga
1451 accacgtggt cactcactct agtgaccggc ctttcaagtg cggctactgt
1501 ggtcgtgcct tgccggggc caccaccctc aacaaccaca tccgaaccca
1551 cactggagaa aagcccttca gtgcgagag gtgtgagagg agcttcacgc
1601 aggccaccca gttgagccga caccagcgga tgcccaatga gtgcaagcca
1651 ataactgaga gcccagaatc aatcgaagtg gataacggat tgactggttg
1701 gaattaaact gcaaggaatg tcatgattaa atgtcacgga cacttaagca
1751 aaaccaaaga tttcctttga gcaactttca atcagtccca gaaaccaaaa
1801 gcagtaataa aataagtaag attgttagag atattgatcc tggcatggaa
1851 gtcagaccag gaaagagatt atttatttat gactaaggga tgagacttat
1901 ttcagtggaa aacttaactt gggattggta acattccca gtcccaccat
1951 gtatttgct ttgttttcta aaaagctttt taaaaactgt tatttaatta
2001 ccaaagggag gaatcgtatg ggttcttctg cccaccgttg tgactaagaa
2051 tgcacaggga cttggttctc gttgcacctt ttttagtaa catgtttcat
2101 ggggacccac tgtacagccc ttcattctgc tgtgtcagtt tggcctggcc
2151 tgacactggc ttgcccagcg gggaccacgg aagcagagtg agagccttcg
2201 ctgagtcaat gctacttca gccccagacg catcccattt ccatgtcttc
2251 catgctcact gctcatgcac ttttttacacg gtttcttcca aacagcccgg
2301 tcttgatgca ggagagtctg gaaaggaag aaaatggttt cagtttcaaa
2351 attcaaagga aaagttgag gacttatttt gtcctgtcaa gattgcaaga
2401 acatgtaaaa tgtacggagc ttcataatac gttatattgt tccgaagcag
2451 ctcgttgaga acatttgtt ttcaataaca ttttagct
```

FIGURE 5A

PFM3a aa

```
  1 KAQQPTAVES GAQVRPHSRA LRGPPNFLAC RSGGFRAAQS LGLSSRAAQG
 51 HVAHAGRTLS RTRTLTETPA LAGLSALPVS QLPVFAPLAA AAVAAEPLPP
101 KELCLGATSG PGPVKCGGGG GGGGEGRGAP RFRCSAEELD YYLYGQQRME
151 IIPLNQHTSD PNNRCDMCAD NRNGECPMHG PLHSLRRLVG TSSAAAAAPP
201 PELPEWLRDL PREVCLCTST VPGLAYGICA AQRIQQGTWI GPFQGVLLPP
251 EKVQAGAVRN TQHLWEIYDQ DGTLQHFIDG GEPSKSSWMR YIRCARHCGE
301 QNLTVVQYRS NIFYRACIDI PRGTELLVWY NDSYTSFFGI PLQCIAQDEN
351 LNVPSTVMEA MCRQDALQPF NKSSKLAPTT QQRSVVFPQT PCSRNFSLLD
401 KSGPIESGFN QINVKNQRVL ASPTSTSQLH SEFSDWHLWK CGQCFKTFTQ
451 RILLQMHVCT QNTDRPYQCG HCSQSFSQPS ELRNHVVTHS SDRPFKCGYC
501 GRAFAGATTL NNHIRTHTGE KPFKCERCER SFTQATQLSR HQRMPNECKP
551 ITESPESIEV DNGLTGWN
```

FIGURE 5B

PFM3b nt

```
   1 aaagcgcagc agcccacggc ggttgagtcg ggcgcccagg tccgtccgca
  51 ctctcgcgcc ctccgcgggc ctcccaattt tctcgcttgc aggtcgggag
 101 gtttccgggc ggcacaatct ctaggactct cctcccgcgc tgctcagggg
 151 catgtagcgc acgcagggcg cacactctcg cgcacccgca cgctcaccga
 201 gacacccgcg ctggctggtc tctcggccct gccggtgtcg cagctgccgg
 251 tgttcgcgcc tctagccgcc gctgccgtcg ccgccgagcc gctgccccccc
 301 aaggaactgt gcctcggcgc cacctccggc cccgggcccg tcaagtgcgg
 351 tggtggtggc ggcggcggcg gggagggtcg cggcgccccg cgcttccgct
 401 gcagcgcaga ggagctggac tattacctgt atggccagca gcgcatggag
 451 atcatcccgc tcaaccagca caccagcgac cccaacaacc gttgcgacat
 501 gtgcgcggac aaccgcaacg gcgagtgccc tatgcatggg ccactgcact
 551 cgctgcgccg gcttgtgggc accagcagcg ctgcggccgc cgcgcccccg
 601 ccggagctgc cggagtggct gcgggacctg cctcgcgagg tgtgcctctg
 651 caccagtact gtgcccggcc tggcctacgg catctgcgcg gcgcagagga
 701 tccagcaagg cacctggatt ggacctttcc aaggcgtgct tctgccccca
 751 gagaaggtgc aggcaggcgc cgtgaggaac acgcagcatc tctgggagtt
 801 aaatgtccct tcaacggtaa tggaagccat gtgcagacaa gacgccctgc
 851 agcccttcaa caaaagcagc aaactcgccc taccaccca gcagcgctcc
 901 gttgttttcc cccagactcc gtgcagcagg aacttctctc ttctggataa
 951 gtctgggccc attgaatcag gatttaatca aatcaacgtg aaaaaccagc
1001 gagtcctggc aagcccaact tccacaagcc agctccactc ggagttcagt
1051 gactggcatc tttggaaatg tgggcagtgc tttaagactt tcacccagcg
1101 gatcctctta cagatgcacg tgtgcacgca gaacaccgac agaccctacc
1151 aatgcggcca ctgctcccag tccttttccc agccttcaga actgaggaac
1201 cacgtggtca ctcactctag tgaccggcct ttcaagtgcg gctactgtgg
1251 tcgtgccttt gccggggcca ccaccctcaa caaccacatc cgaacccaca
1301 ctggagaaaa gcccttcaag tgcgagaggt gtgagaggag cttcacgcag
1351 gccacccagt tgagccgaca ccagcggatg cccaatgagt gcaagccaat
1401 aactgagagc cagaatcaa tcgaagtgga taacggattg actggttgga
1451 attaaactgc aaggaatgtc atgattaaat gtcacggaca cttaagcaaa
1501 accaaagatt tcctttgagc aactttcaat cagtcccaga aaccaaaagc
1551 agtaataaaa taagtaagat tgttagagat attgatcctg gcatggaagt
1601 cagaccagga aagagattat ttatttatga ctaagggatg agacttatt
1651 cagtggaaaa cttaacttgg gattggtaaa cattccagt cccaccatgt
1701 attttgcttt gttttctaaa aagctttta aaaactgtta tttaattacc
1751 aaagggagga atcgtatggg ttcttctgcc caccgttgtg actaagaatg
1801 cacagggact tggttctcgt tgcacctttt tttagtaaca tgtttcatgg
1851 ggacccactg tacagccctt cattctgctg tgtcagtttg gcctggcctg
1901 acactggctt gccagcggg gaccacggaa gcagagtgag agccttcgct
1951 gagtcaatgc taccttcagc cccagacgca tcccatttcc atgtcttcca
2001 tgctcactgc tcatgcactt tttacacggt ttcttccaaa cagcccggtc
2051 ttgatgcagg agagtctgga aaaggaagaa aatggtttca gtttcaaaat
2101 tcaaaggaaa aagttgagga cttatttgt cctgtcaaga ttgcaagaac
2151 atgtaaaatg tacggagctt cataatacgt tatattgttc cgaagcagct
2201 cgttgagaaa catttgtttt caataacatt ttagct
```

FIGURE 6A

PFM3b aa

```
  1 KAQQPTAVES GAQVRPHSRA LRGPPNFLAC RSGGFRAAQS LGLSSRAAQG
 51 HVAHAGRTLS RTRTLTETPA LAGLSALPVS QLPVFAPLAA AAVAAEPLPP
101 KELCLGATSG PGPVKCGGGG GGGGEGRGAP RFRCSAEELD YYLYGQQRME
151 IIPLNQHTSD PNNRCDMCAD NRNGECPMHG PLHSLRRLVG TSSAAAAAPP
201 PELPEWLRDL PREVCLCTST VPGLAYGICA AQRIQQGTWI GPFQGVLLPP
251 EKVQAGAVRN TQHLWELNVP STVMEAMCRQ DALQPFNKSS KLAPTTQQRS
301 VVFPQTPCSR NFSLLDKSGP IESGFNQINV KNQRVLASPT STSQLHSEFS
351 DWHLWKCGQC FKTFTQRILL QMHVCTQNTD RPYQCGHCSQ SFSQPSELRN
401 HVVTHSSDRP FKCGYCGRAF AGATTLNNHI RTHTGEKPFK CERCERSFTQ
451 ATQLSRHQRM PNECKPITES PESIEVDNGL TGWN
```

FIGURE 6B

PFM4 nt

```
   1 atcattccct tactcgaatg aattaaagta caggattggg gctaaataat
  51 gtgagtgcca cgctctttct gaagctctta tatcaaggaa catgcattac
 101 aactttccta atccctgctt ccctcacttc cagattgtga gatgtgtcag
 151 aacttcttca ttgacagctg tgctgctcat gggcccccta catttgtaaa
 201 ggacagtgca gtggacaagg ggcatcccaa ccgttcagcc ctcagtctgc
 251 ccccggggct gagaattggg ccatcaggca tccctcaggc tgggcttgga
 301 gtatggaacg aggcatctga tctgccactg ggtctgcact ttggcccta
 351 tgagggccga attacagaag acgaagaggc agccaacagt ggatattcct
 401 ggctaatcac caaggggaga aactgctatg agtatgtgga tggaaaagat
 451 aaatcctcgg ccaactggat gaggtatgtg aactgtgccc gggatgatga
 501 agagcagaac ctggtggcct tccagtacca caggcagatc ttctatagaa
 551 cctgccgagt cattaggcca ggctgtgaac tgctggtctg gtatggggat
 601 gagtatggcc aggaactggg catcaagtgg ggcagcaagt ggaagaaaga
 651 gctcatggca gggagagaac aaagccaga gatccatcca tgtccctcat
 701 gctgtctggc cttttcaagt caaaaatttc tcagtcaaca tgtggaacgc
 751 aatcactcct ctcagaactt cccaggacca tctgcaagaa aacttctcca
 801 accagagaat ccctgcccag gggatcagaa tcaggagcgg caatattctg
 851 atccacgctg ctgtaatgac aaaaccaaag gtcaagagat caaagaaagg
 901 tccaaactct tgaataaaag gacatgcag agggagattt caaggccctt
 951 ttctagccca cccaaaggac aaatggggag ctctagagtg ggagaaagaa
1001 tgatggaaga agagtccaga acaggccaga aagtgaatcc agggaacaca
1051 ggcaaattat ttgtgggggt aggaatctca agaattgcga aagtcaaata
1101 tggagagtgt gggcaaggtt tcagtgataa gtcagatgtt attacacacc
1151 aaaggacaca cacaggggg aagccctacg tctgcagaga gtgtggggag
1201 ggctttagcc ggaagtcaga cctcctcagt caccagagga cacacacagg
1251 ggagaagcct tatgtctgca gagagtgtga gcggggcttt agccggaagt
1301 cagtcctcct cattcaccag aggacacaca ggggagaagc cccagtctgc
1351 aggaaggatg agtaagtcat tagtaataaa accttatctc aatagccaca
1401 agaagacaaa cgtgatcacc acacact
```

FIGURE 7A

PFM4 aa

```
  1 MCQNFFIDSC AAHGPPTFVK DSAVDKGHPN RSALSLPPGL RIGPSGIPQA
 51 GLGVWNEASD LPLGLHFGPY EGRITEDEEA ANSGYSWLIT KGRNCYEYVD
101 GKDKSSANWM RYVNCARDDE EQNLVAFQYH RQIFYRTCRV IRPGCELLVW
151 YGDEYGQELG IKWGSKWKKE LMAGREPKPE IHPCPSCCLA FSSQKFLSQH
201 VERNHSSQNF PGPSARKLLQ PENPCPGDQN QERQYSDPRC CNDKTKGQEI
251 KERSKLLNKR TWQREISRAF SSPPKGQMGS SRVGERMMEE ESRTGQKVNP
301 GNTGKLFVGV GISRIAKVKY GECGQGFSDK SDVITHQRTH TGGKPYVCRE
351 CGEGFSRKSD LLSHQRTHTG EKPYVCRECE RGFSRKSVLL IHQRTHRGEA
401 PVCRKDE
```

FIGURE 7B

PFM5 nt

```
   1 aaaagcagca tcagacaaga gctttattaa tcccttacac gagcaaatgc
  51 gatctctgac ctactagact tgttttccta caatttcaca aaaagcctcg
 101 ctagaggaat gtgcaaggac agaagggaaa ctgaggagag acccgcaact
 151 cattagcgaa ataatagggt gcacttcaat aaaaatgcgg tcctgaagtg
 201 gagcagactc accggcaagg agcccggaaa atcgtcaggg gcggcggcaa
 251 aatactatca aatcagcctg ggaagcatct tttcgctcag caagttcaag
 301 agaacaaata tgttacaatc cttgcctatt cttgcctcca cttcataatg
 351 tcataaaagc cacctggggt gtcatttatc aacctctctc cagcccactc
 401 ttccaaaata acactacagt ttcctacatg tgtattttg ccaggactcc
 451 aaagagcctt gctaaagtgg aacaagcaaa atcctcccct ggcctcctgg
 501 gactgcagtc accaggctgt caaagcctca atacccact gagttccaga
 551 gaagggtctc aaagctggga gaggatcaaa ctaacatgga gtagagaatt
 601 gaactgtgaa aaagaagccc gagattcccc agcgacgtgg tgttgcagcc
 651 ccgttgaagg agtcaacttg caggctgtta aagacctcaa gtcattagca
 701 tcagctgctg cactaaaggg gcaagtcagc gcctctaagt ggcttagcgc
 751 acaaacgagg ctcccgagac ggcctcggca actccatccc ctcctccacc
 801 acccgctgga tgtgaaaagc tttccggagc ccatcttggg ggaagcttgg
 851 tagtgttggc gctcctgaag agagacgacg cccgtttatc accccaggc
 901 aactagctgc gcaaatcagc ggtggctcca gggctagaga atccctggag
 951 ctaaccgcac ccctctccct ttcacggaac gcggactccg gggaaatacg
1001 cacggggtcc gcacgcgctg ggtgtccagc tctctgtcac agcttctcca
1051 agtgcctagt gaaacgggga aaggccctct ccaatcattt tggaagagcc
1101 taaaaggcgg caacaccaac acctcttgac atggaaatac actgatacaa
1151 taggcaaaag gaaacactcg attgcatctt cccggttcca ggtggcctta
1201 tttgggagat tctatactga ccttattcct gtgatggagg atactggcat
1251 ccagcgaggc atctgggatg gagatgccaa ggctgtccaa caatgtctga
1301 cagatatttt taccagcgtt tacaccacct gcgacatccc tgagaatgct
1351 atatttggtc cctgtgtcct gagccatact tccctatatg acagcatagc
1401 tttcatagct ctcaagtcta ctgacaagag aacagtaccg tatatctttc
1451 gggtagacac ctcagcagca aatggttcct cagaaggtct catgtggctg
1501 cggttggtcc aatcggccag agataaggaa gagcagaacc ttgaagccta
1551 cataaaaaac ggacagctgt tctaccgctc tctccgcagg attgccaaag
1601 acgaggagtt actagtttgg tacgggaaag aactgactga gttactcttg
1651 ctttgcccct ctagatccca caacaaaatg aatgggtcgt ccccttacac
1701 atgcctggaa tgcagccaac gtttccagtt tgagttcccc tatgtggcgc
1751 atctgcgttt ccgctgcccc aagagacttc acagcgctga tataagtccc
1801 caagcgaac aaggcggcgg cgtgggcacc aaggaccacg ggggcggcgg
1851 cggcggtggc aaagaccagc agcagcagca gcaggaggca cctttaggcc
1901 cgggtcccaa gttttgcaaa gccggccccc tccaccacta cccatccccc
1951 tccccggaaa gcagcaaccc atccgctgcc gccggcggca gcagcgcgaa
2001 gccatccaca gacttccaca acctggccag ggagctggaa aactcccggg
2051 gaggcagcag ctgctcccca gcccagagcc tcagcagcgg tagggcagcg
2101 gcggcggcgg cggccaccag gaggcggagc tgagtcccga cggcatcgcc
2151 acgggcggcg gcaaaggaaa gaggaaattc ccggaggagg cggcggaggc
2201 cggcggtggc gctggtttgg tagggccgc gttgtaacgg ccctcccgg
2251 cctccaagga ggatctggtg tgcacaccgc agcagtaccg agcctcgggc
2301 agctacttcg gcctggaaga gaacggccgc ctcttcgcgc cgccaagtcc
2351 cgagacgggc gaggcgaagc gcagcgcctt cgtggaggtg aagaaggctg
2401 cccgcgcggc cagcctgcag gaggagggga cagccgacgg cgcgggagtc
2451 gcctccgagg accaggacgc tggcggcggc ggcggctcct ccacgcccgc
2501 ggccgc
```

FIGURE 8A

PFM5 aa

```
  1 MEDTGIQRGI WDGDAKAVQQ CLTDIFTSVY TTCDIPENAI FGPCVLSHTS
 51 LYDSIAFIAL KSTDKRTVPY IFRVDTSAAN GSSEGLMWLR LVQSARDKEE
101 QNLEAYIKNG QLFYRSLRRI AKDEELLVWY GKELTELLLL CPFKSHNKMN
151 GSSPYTCLEC SQRFQFEFPY VAHLRFRCPK RLHSADISPQ DEQGGGVGTK
201 DHGGGGGGGK DQQQQQQEAP LGPGPKFCKA GPLHHYPSPS PESSNPSAAA
251 GGSSAKPSTD FHNLARELEN SRGGSSCSPA QSLSSGRAAA AAAATRRRS
```

FIGURE 8B

PKZL1 nt

```
   1 actgcgtgag tgcaacactg tccctggtga gcatgcctgg gttttgtgtt
  51 acaggctttc ttggcatttg gggatgtcac tgtggatttc acccagaagg
 101 aatggaggct gctgagccct gctcagaggg ccctgtacag ggaggtgaca
 151 ctggagaact acagccacct ggtctcacta ggaattctcc attctaaacc
 201 agaactcatc aggcggctag agcaagggga agtgccctgg ggagaagaga
 251 gaagacgccg gccaggcccc tgtgcagaaa gacttttcgt tactgattca
 301 gtctcattgt tggtctattc tccaggaata tatgcagaac atgtcctgcg
 351 gcccaagaat cttggacttg cacatcagag gcaacagcaa ctacaatttt
 401 ctgatcaaag cttccagagt gacacagctg aaggtcaaga aaagaaaaa
 451 agcactaagc ccatggcatt tccagcccca ccctaagac atgcagtaag
 501 ctcaaggagg aggaacagtg tagtggaaat agagtctagt caaggccaga
 551 gggaaaatcc tacagaaata gacaaagtat gaaaggaat agaaaattca
 601 agatggggag cattcaagtg tgcagagtgt gggcaagact cagccggaa
 651 gatgatggta atcatacaca aaaagcaca ttccaggcag aaacttttta
 701 catgcaggga gtgtcaccag ggctttagag atgagtcagc attgctcttg
 751 caccagaaca cacacacagg agagaagtcc tatgtgtgca gtgtgtgtgg
 801 gcgaggcttc agcctcaagg ccaacctcct cagacaccag aggacacact
 851 cagaggagaa gccttatgga tgtcgggagt gtgggcgaag gtttcgggat
 901 aagtcctcct ataacaagca cctgagggca cacttgggtg agaaacgttt
 951 tttctgcagg gattgtgggc gaggctttac cttgaagcca aatctcacca
1001 tacatcagag gacacactca ggagagaagc ccttcatgtg caagcagtgt
1051 gagaaaagtt ttagtttgaa ggcaaatctt cttagacatc agtggacaca
1101 ctcgggggaa aggccattta attgcaagga ttgcgggcga ggcttcatcc
1151 taaaatcaac tctcctcttc accagaaga cacactcagg ggagaagcct
1201 ttcatctgta gtgaatgtgg gcaaggattt atctggaagt caaatcttgt
1251 gaaacaccag cttgcacatt ctggcaagca gccttttgta tgcaaggagt
1301 gtgggcgagg cttcaactgg aagggaaatc tcctcacaca ccagaggaca
1351 cactcagggg agaagccctt cgtgtgtaat gtgtgtgggc aaggcttcag
1401 ctggaagaga agtctcacca gacaccactg gcggatacac tcaaaggaga
1451 agccttttgt ttgccaggag tgtaagcgag gctataccag taagtcagac
1501 ctcactgtgc atgaaagaat acacacagga gagggccctt atgaatgcca
1551 agagtgtgga cgaaagttta gcaataagtc atactacagt aagcacttaa
1601 agagacactt acgtgagaag cgttttgta caggagtgt gggtgaggct
1651 tcatcttgaa gttatatctc accatccatc agaggacaca ctcaggagag
1701 taactttgct ttgttacaag ctttagttga ggctgcataa cttgttcgtg
1751 aagatataac agaggcagac agaatccaga gggctacaga gaacctgaat
1801 tcaacccatg tgtccccaag agattcagag aaaaga
```

FIGURE 9A

PKZL1 aa

```
  1 ACLGFVLQAF LAFGDVTVDF TQKEWRLLSP AQRALYREVT LENYSHLVSL
 51 GILHSKPELI RRLEQGEVPW GEERRRRPGP CAERLFVTDS VSLLVYSPGI
101 YAEHVLRPKN LGLAHQRQQQ LQFSDQSFQS DTAEGQEKEK STKPMAFSSP
151 PLRHAVSSRR RNSVVEIESS QGQRENPTEI DKVLKGIENS RWGAFKCAEC
201 GQDFSRKMMV IIHKKAHSRQ KLFTCRECHQ GFRDESALLL HQNTHTGEKS
251 YVCSVCGRGF SLKANLLRHQ RTHSEEKPYG CRECGRRFRD KSSYNKHLRA
301 HLGEKRFFCR DCGRGFTLKP NLTIHQRTHS GEKPFMCKQC EKSFSLKANL
351 LRHQWTHSGE RPFNCKDCGR GFILKSTLLF HQKTHSGEKP FICSECGQGF
401 IWKSNLVKHQ LAHSGKQPFV CKECGRGFNW KGNLLTHQRT HSGEKPFVCN
451 VCGQGFSWKR SLTRHHWRIH SKEKPFVCQE CKRGYTSKSD LTVHERIHTG
501 ERPYECQECG RKFSNKSYYS KHLKRHLREK RFCTGSVGEA SS
```

FIGURE 9B

PKZL2 nt

```
   1 acattcaggg atgtgactgt gatcttcaca gaagcagaat ggaagagact
  51 gagtccagag cagaggaatc tatacaaaga agtgatgctg gagaattaca
 101 ggaatcttct ctcattggaa atctacactt gttcctcctg ccttctggcc
 151 ttctcctgtc agcagttcct cagtcaacat gtacttcaga tcttcctggg
 201 cttatgtgca gaaaatcact tccatccagg gaattctagc ccagggcatt
 251 ggaaacagca ggggcagcag tattcccatg taagctgttg gtttgaaaat
 301 gcagaaggtc aggagagagg aggtggctcc aaaccctggt ctgcaaggac
 351 agaggagaga gaaacctcaa gggcattccc cagcccactc caaagacagt
 401 cagcaagtcc tagaaaaggc aacatggtgg tagaaacaga gcccagctca
 451 gcccaaagac caaaccctgt gcagctagac aaaggcttga aggaattaga
 501 aaccttgaga tttggagcaa tcaactgtag agagtatgaa ccggaccata
 551 acctggaatc aaactttatt acaaacccga ggaccctctt agggaagaag
 601 ccctacattt gcagtgattg tgggcgaagc tttaaagata gatcaaccct
 651 catcagacac catcgtatac actcgatgga gaagccttat gtgtgcagtg
 701 agtgcgggcg aggttttagc cagaagtcca acctcagcag acaccagaga
 751 acacattcag aagagaagcc ttatttgtgc agggagtgtg ggcaaagctt
 801 tagaagtaag tccatcctca atagacatca gtggactcac tcagaggaga
 851 agccctatgt ttgcagcgag tgtgggcgag gctttagcga gaagtcatcc
 901 ttcatcagac accagaggac acactccggt gagaaacct atgtgtgcct
 951 ggagtgtgga cgaagctttt gtgataagtc aaccctcaga aaacaccaga
1001 ggatacactc aggggagaag ccttatgttt gcagggagtg tgggcgaggc
1051 tttagccaga actcagatct catcaaacac cagaggacac acttggatga
1101 gaagccttat gtttgcaggg agtgtgggcg aggcttttgt gacaagtcaa
1151 ccctcatcat acacgagcgg acgcactctg gagagaagcc ttatgtgtgt
1201 ggtgagtgtg gcgaggctt tagtcggaaa tcactcctcc ttgtccacca
1251 gaggacacac tcaggggaga agcattatgt ctgcagggag tgtaggcgag
1301 gttttagcca gaagtcaaat ctcatcagac accagaggac gcactcaaat
1351 gagaagcctt atatttgcag ggaatgtggg cgaggctttt gtgacaagtc
1401 aaccctcatt gtacatgaga ggacacactc aggagagaag ccttacgtgt
1451 gcagtgagtg tggccgaggc tttagccgga atcactcct ccttgtccac
1501 cagaggacac actcagggga gaagcattat gtttgtaggg agtgtgggcg
1551 aggctttagt cataagtcaa atctcatcag acaccagagg acacactgac
1601 gggagaaacc tgtgtatgca ggggtcatga acaagacctg agtgaccagt
1651 caagcctcat gttaccccag agagacacat ggggagtaga ccctgtgtac
1701 acagattgtg agtgaagttc cagagatgtg tcagcccta tcaggcatgg
1751 gagggacacg ttcaggagag gagccttatg agtatagagt acgggcaact
1801 gtagccatca gtcagccttg agcatgcaca aaggacaca cttaggagag
1851 aagtttatgt gtagggactg tgggaaggct ttagcaataa tcaacattta
1901 ccagacatcc aatgacagcc tcagggaaa gcaccttgt ctggggagtg
1951 ttggggagca tcagtaaaag
```

FIGURE 10A

PKZL2 aa

```
  1 TFRDVTVIFT EAEWKRLSPE QRNLYKEVML ENYRNLLSLE IYTCSSCLLA
 51 FSCQQFLSQH VLQIFLGLCA ENHFHPGNSS PGHWKQQGQQ YSHVSCWFEN
101 AEGQERGGGS KPWSARTEER ETSRAFPSPL QRQSASPRKG NMVVETEPSS
151 AQRPNPVQLD KGLKELETLR FGAINCREYE PDHNLESNFI TNPRTLLGKK
201 PYICSDCGRS FKDRSTLIRH HRIHSMEKPY VCSECGRGFS QKSNLSRHQR
251 THSEEKPYLC RECGQSFRSK SILNRHQWTH SEEKPYVCSE CGRGFSEKSS
301 FIRHQRTHSG EKPYVCLECG RSFCDKSTLR KHQRIHSGEK PYVCRECGRG
351 FSQNSDLIKH QRTHLDEKPY VCRECGRGFC DKSTLIIHER THSGEKPYVC
401 GECGRGFSRK SLLLVHQRTH SGEKHYVCRE CRRGFSQKSN LIRHQRTHSN
451 EKPYICRECG RGFCDKSTLI VHERTHSGEK PYVCSECGRG FSRKSLLLVH
501 QRTHSGEKHY VCRECGRGFS HKSNLIRHQR TH
```

FIGURE 10B

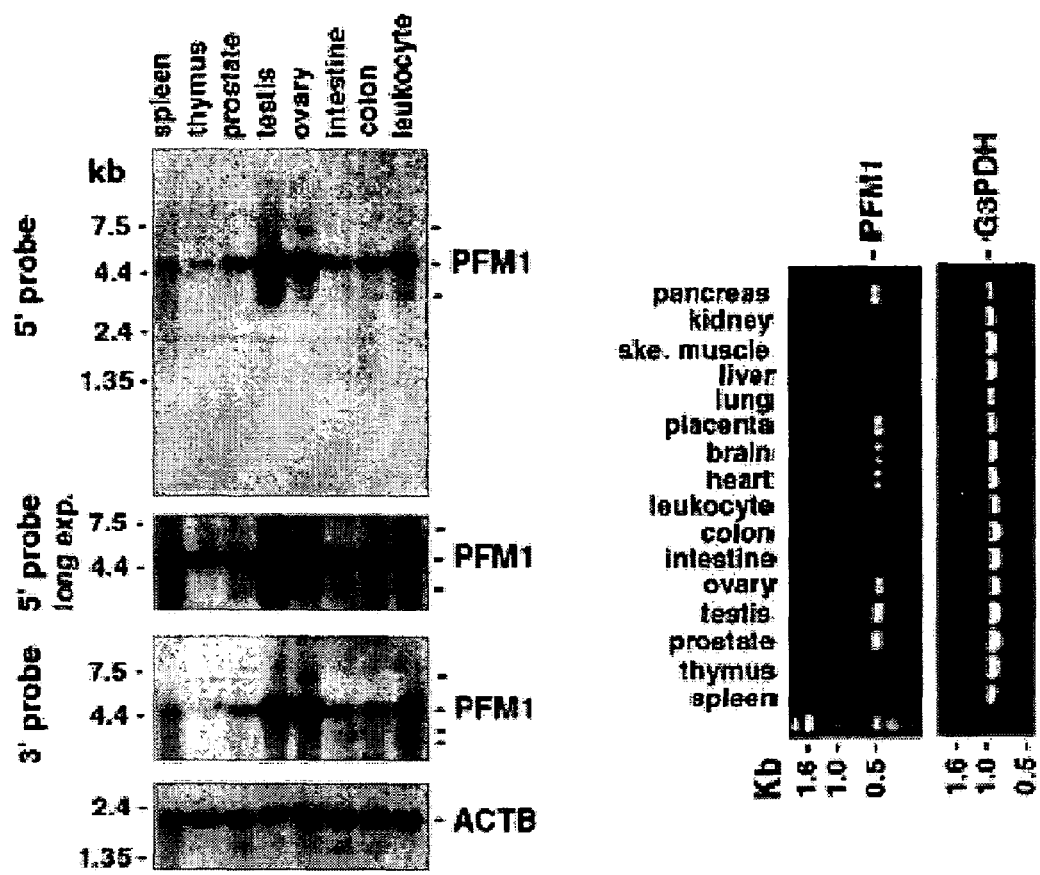
Figure 11 B
Figure 11 C
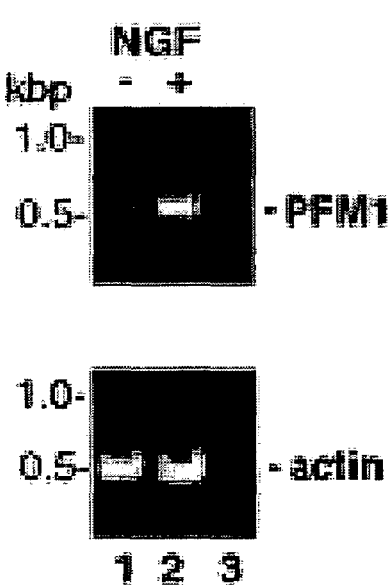
Figure 11 D

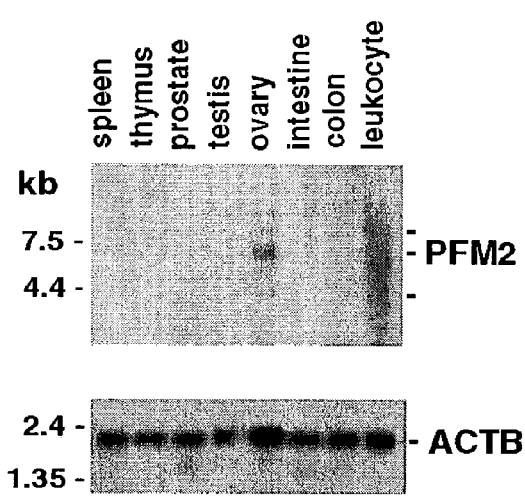
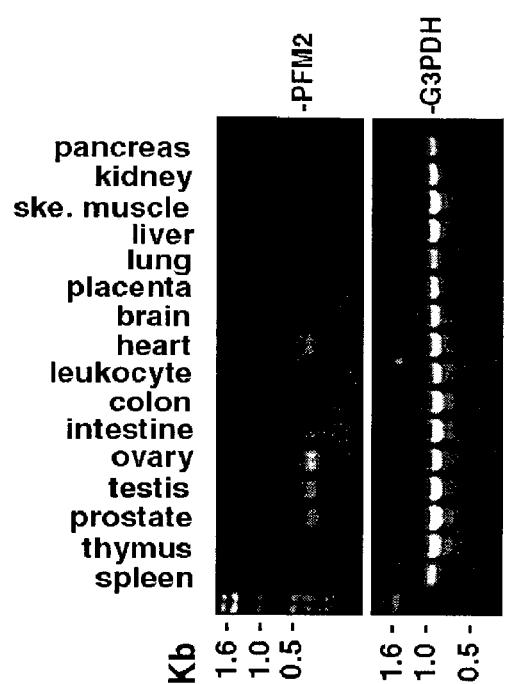
FIGURE 12B
FIGURE 12C

FIGURE 13A
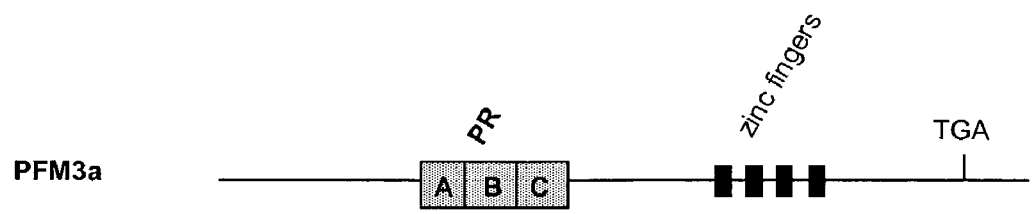
PFM3a
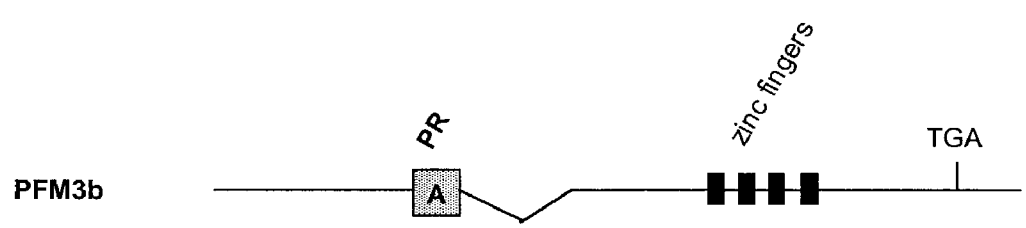
PFM3b
FIGURE 13B human PFM4 cDNA structure human PFM5 cDNA structure

PR-DOMAIN CONTAINING NUCLEIC ACIDS, POLYPEPTIDES, ANTIBODIES AND METHODS This application is a continuation of application Ser. No. 09/389,956, filed Sep. 3, 1999, now U.S. Pat. No. 6,586,579.

This invention was made in part with government support under grant number RO1 CA76146, awarded by the National Institutes of Health. Accordingly, the United States government has certain rights in this invention.

BACKGROUND OF THE INVENTION

1. Field of the Invention

This invention relates generally to proliferative disorders such as cancer and, more specifically, to PR-domain containing genes and gene products that can be used to diagnose and treat proliferative disorders.

2. Background Information

Cancer is one of the leading causes of death in industrialized nations. Cancerous tumors result when a cell escapes from its normal growth regulatory mechanisms and proliferates in an uncontrolled fashion. Cells from the primary tumor generally metastasize to vital organs if treatment of the primary tumor is either not complete or not initiated early enough. Thus, early diagnosis and effective treatment of tumors is essential for survival.

Cancer involves the clonal replication of populations of cells that have gained competitive advantage over normal cells through the alteration of regulatory genes. Regulatory genes can be broadly classified into "oncogenes" which, when activated or overexpressed promote unregulated cell proliferation, and "tumor suppressor genes" which, when inactivated or underexpressed fail to prevent abnormal cell proliferation. Loss of function or inactivation of tumor suppressor genes is thought to play a central role in the initiation and progression of a significant number of human cancers.

A number of tumor suppressor genes have been identified that, when inactivated, are involved in the initiation or progression of human cancers. Known tumor suppressor genes include RB, p53, DCC, APC/MCC, NF1, NF2, WT1, VHL, BRCA1, MST1 and WAF1/CIP1. Approaches for treating cancer by modulating the function of several of these tumor suppressor genes, either with pharmaceutical compounds that target their encoded proteins, or by gene therapy methods, have yielded promising results in animal models and in human clinical trials.

Approaches for diagnosing and prognosing cancer by identifying mutations in tumor suppressor genes have also been developed. For example, identifying individuals containing germline mutations in known tumor suppressor genes has permitted the identification of individuals at increased risk of developing cancer. Such individuals are then closely monitored or treated prophylactically to improve their chance of survival. Identifying the pattern of alterations of known tumor suppressor genes in biopsy samples is also being used to determine the presence or stage of a tumor. Being able to determine whether a cancer is benign or malignant, or at an early or late stage of progression, provides the patient and clinician with a more accurate prognosis and can be used to determine and monitor the course of treatment.

One important family of tumor suppressor genes that has recently been identified are PR-domain containing genes. A "PR domain" is a motif of approximately 100 to 125 amino acids first identified as a region of homology between the Rb-binding zinc finger protein RIZ, and the transcriptional repressor protein PRD1-BF1/Blimp1, which promotes B-cell differentiation (Buyse et al., *Proc. Natl. Acad. Sci. USA* 92:4467-4471 (1995); Huang, *Cell* 78:9 (1994)). A PR domain motif is also found in the MDS1-EVI1 myeloid leukemia gene (Fears et al., *Proc. Natl. Acad. Sci. USA* 93:1642-1647 (1996)). PR domain-encoding genes have also been identified in other mammals and in lower organisms, including *C. elegans* and *Drosophila*, suggesting an evolutionarily conserved function for this domain.

Several observations indicate that PR-domain containing gene products are negative regulators of cell growth and tumorigenesis, whereas the PR-deficient products of these genes are involved in growth promotion and oncogenesis. For example, the PR region of MDS1-EVI1 is often disrupted by leukemia-associated chromosomal insertions and translocations. These disruptions result in loss of the PR-containing MDS1-EVI1 product and selective retention of the PR-deficient EVI1 product. In contrast, the PR-EVI1 product is overexpressed in some tumor cells, and acts as an oncogene (Morishita et al., *Cell* 54:831-840 (1988); Morishita et al., *Proc. Natl. Acad. Sci. USA* 89:3937-3941 (1992))

Similarly, the RIZ gene produces two products, a PR-containing protein, RIZ1, and a PR-deficient protein, RIZ2, which is generated from an internal promoter. RIZ1 is commonly absent or underexpressed in a number of human neoplasias, including breast cancer, neuroblastoma and lung cancer. In these cases, the PR-deficient product, RIZ2, is expressed at normal levels (He et al., *Cancer Res.* 58:4238-4244 (1998)). These results suggest that the PR-containing RIZ1 product is a negative regulator of cell proliferation and tumorigenesis, whereas maintenance of RIZ2 expression may be required for oncogenesis.

As further evidence that RIZ is a tumor suppressor gene, forced expression of the RIZ1 product in breast cancer cells causes cell cycle arrest at the G2/M phase of the cell cycle, and programmed cell death (He et al., *Cancer Res.* 58:4238-4244 (1998)). Additionally, consistent with a role of RIZ1 in growth suppression, mice in which RIZ1, but not RIZ2, is inactivated, are tumor prone.

A third PR domain-containing gene, PRDI-BF1/BLIMP1 is also likely to be a tumor suppressor gene. PRD1-BF1/BLIMP1 maps to the 6q21 region commonly deleted in non-Hodgkin's lymphoma (Mock et al., *Genomics* 37:24-28 (1996)) and is thus a strong candidate tumor suppressor for B-cell non-Hodgkin's lymphoma. Additionally, PRDI-BF1/BLIMP1 is a transcriptional repressor of c-Myc (Lin et al., *Science* 276:596-598 (1997)), which is an oncogene critically involved in B cell lymphoma.

In view of the importance of tumor suppressor genes and related molecules in the detection and treatment of cancer, there exists a need to identify additional tumor suppressor genes. In particular, in view of the established role of PR-domain containing genes as tumor suppressor genes, there exists a need to identify and characterize additional PR-domain family members. The present invention satisfies this need and provides related advantages as well.

SUMMARY OF THE INVENTION

The invention provides an isolated PR Family Member (PFM) nucleic acid molecule that contains a PFM PR domain nucleotide sequence selected from the group consisting of SEQ ID NOS:17, 19, 21, 23, 25 and 27; or a PFM ZF domain nucleotide sequence selected from the group consisting of SEQ ID NOS:63, 65, 67, 69, 71, 73 and 75; or a modification thereof.

The invention also provides an isolated PFM nucleic acid molecule that contains a nucleotide sequence that encodes a PFM PR domain polypeptide having an amino acid sequence selected from the group consisting of SEQ ID NOS:18, 20, 22, 24, 26 and 28; or a nucleotide sequence that encodes a PFM ZF domain polypeptide having an amino acid sequence selected from the group consisting of SEQ ID NOS:64, 66, 68, 70, 72, 74 and 76; or a nucleotide sequence that encodes an immunologically equivalent modification thereof.

Further provided is an isolated PFM oligonucleotide, containing between 15 and 300 contiguous nucleotides of SEQ ID NOS:2, 4, 6, 8, 10, 12, 14 or 16.

Also provided are methods for detecting a PFM nucleic acid molecule in a sample. In one embodiment, the method consists of contacting the sample with a PFM nucleic acid molecule under conditions that allow specific hybridization to PFM nucleic acid, and detecting specific hybridization. In another embodiment, the method consists of contacting the sample with a PFM primer pair under conditions that allow amplification of PFM nucleic acid, and detecting amplified PFM nucleic acid.

Further provided is a method of modulating cell growth. The method consists of introducing a vector containing a PFM nucleic acid operatively linked to a promoter of RNA transcription into a host cell, and expressing encoded PFM polypeptide in an amount effective to modulate growth of the cell.

The invention also provides an isolated PFM polypeptide, containing a PFM PR domain amino acid sequence selected from the group consisting of SEQ ID NOS:18, 20, 22, 24, 26 and 28; or a PFM ZF domain amino acid sequence selected from the group consisting of SEQ ID NOS:64, 66, 68, 70, 72, 74 and 76; or a modification thereof.

Also provided is an isolated PFM peptide, containing at least 8 contiguous amino acids of SEQ ID NOS:2, 4, 6, 8, 10, 12, 14 and 16.

The invention also provides an antibody or antigen binding fragment thereof, which specifically binds a PFM polypeptide. Further provided is a method for detecting PFM polypeptide in a sample, by contacting the sample with a PFM antibody under conditions that allow specific binding of the antibody to PFM polypeptide, and detecting specifically bound antibody.

BRIEF DESCRIPTION OF THE DRAWINGS

FIG. 1A shows the nucleotide sequence (SEQ ID NO:1) and FIG. 1B shows the deduced amino acid sequence SEQ ID NO:2) of PFM1. The zinc finger motifs are shown by underlining, and the regions of similarity between PFM polypeptides including and extending beyond the A, B and C boxes are shown by italics, in FIG. 1B.

FIG. 2A shows the nucleotide sequence (SEQ ID NO:3) and FIG. 2B shows the deduced amino acid sequence SEQ ID NO:4) of PFM2. The zinc finger motifs are shown by underlining, and the regions of similarity between PFM polypeptides including and extending beyond the A, B and C boxes are shown by italics, in FIG. 2B.

FIG. 3A shows the nucleotide sequence (SEQ ID NO:5) and FIG. 3B shows the deduced amino acid sequence SEQ ID NO:6) of mPFM2a. The zinc finger motifs are shown by underlining, and the regions of similarity between PFM polypeptides including and extending beyond the A, B and C boxes are shown by italics, in FIG. 3B.

FIG. 4A shows the nucleotide sequence (SEQ ID NO:7), and FIG. 4B shows the deduced amino acid sequence SEQ ID NO:8) of mPFM2b.

FIG. 5A shows the nucleotide sequence (SEQ ID NO:9) and FIG. 5B shows the deduced amino acid sequence SEQ ID NO:10) of PFM3a. The zinc finger motifs are shown by underlining, and the regions of similarity between PFM polypeptides including and extending beyond the A, B and C boxes are shown by italics, in FIG. 5B.

FIG. 6A shows the nucleotide sequence (SEQ ID NO:11) and FIG. 6B shows the deduced amino acid sequence SEQ ID NO:12) of PFM3b.

FIG. 7A shows the nucleotide sequence (SEQ ID NO:13) and FIG. 7B shows the deduced amino acid sequence SEQ ID NO:14) of PFM4. The zinc finger motifs are shown by underlining, and the regions of similarity between PFM polypeptides including and extending beyond the A, B and C boxes are shown by italics, in FIG. 7B.

FIG. 8A shows the nucleotide sequence (SEQ ID NO:15) and FIG. 8B shows the deduced amino acid sequence SEQ ID NO:16) of PFM5. The zinc finger motif is shown by underlining, and the regions of similarity between PFM polypeptides including and extending beyond the A, B and C boxes are shown by italics, in FIG. 8B.

FIG. 9A shows the nucleotide sequence (SEQ ID NO:77) and FIG. 9B shows the deduced amino acid sequence SEQ ID NO:78) of PKZL1.

FIG. 10A shows the nucleotide sequence (SEQ ID NO:79) and FIG. 10B shows the deduced amino acid sequence SEQ ID NO:80) of PKZL2.

FIG. 11B shows expression of PFM1 in various human tissues by Northern blot analysis. FIG. 11C show expression of PFM1 in various human tissues by RT-PCR analysis. FIG. 11D show expression of PFM1 in NGF-treated and non-treated PC12 cells.

FIG. 12B shows expression of PFM2 in various human tissues by Northern blot analysis. FIG. 12C show expression of PFM2 in various human tissues by RT-PCR analysis.

FIG. 13A shows a schematic representation of the structure of PFM3a and PFM3b. FIG. 13B shows expression of PFM3 in various human tissues by RT-PCR analysis.

DETAILED DESCRIPTION OF THE INVENTION

Figure 11A:
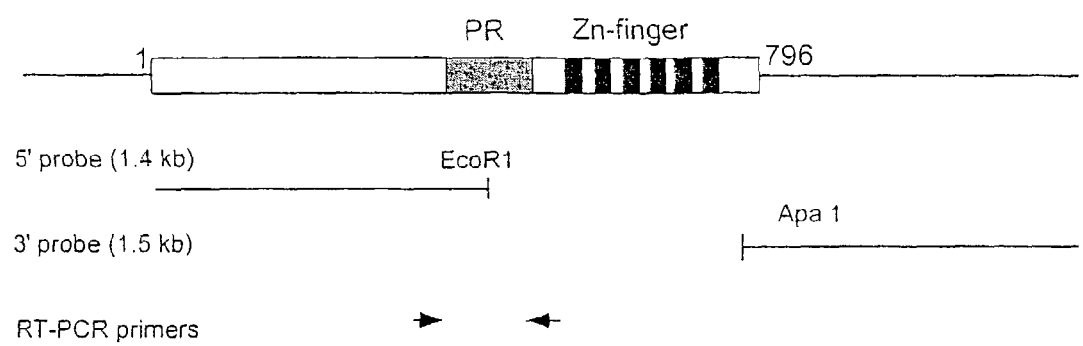
FIG. 11A shows a schematic representation of the structure of PFM1, and also shows the boundaries of the probes and primers used to detect PFM1 expression.

The present invention provides novel "PR Family Member," or "PFM," nucleic acid molecules, polypeptides, antibodies, modulatory compounds, and related methods. The PFM nucleic acids and polypeptides of the invention are important regulators of cell proliferation. Therefore, the molecules and methods of the invention can be used to modulate cell proliferation so as to prevent or treat proliferative disorders, including cancer. Additionally, the molecules and methods of the invention can be used to diagnose and prognose proliferative disorders.

PFM nucleic acid molecules and polypeptides are generally characterized by encoding or containing a "PR domain" and a "zinc finger domain." Exemplary PFM nucleic acid molecules include RIZ, MDS1-EVI1 and PRDI-BF1 (BLIMP1).

The PR domain has been demonstrated to be a protein binding motif involved in the regulation of gene expression (Huang et al., *J. Biol. Chem.* 273:15933-15940 (1998); Soderholm et al., *Leukemia* 11:352-358 (1997)). In particular, the PR domain is considered to function in the assembly of chromatin-based multiprotein complexes involved in either euchromatin-mediated gene activation, or heterochromatin-mediated gene silencing. Lack or inactivation of the PR domain can thus specifically inactivate the chromatin-associated functions of a PFM, without affecting other activities such as DNA binding and chromatin-independent transcriptional activation or repression. Differential chromatin regulation by the PR+ and PR– forms of a PFM gene may therefore underlie the opposite roles of these products in tumorigenesis.

The PR domain is about 100 to 125 amino acids in length, and contains three highly conserved sequences, designated the A, B and C boxes, each of which consists of about 6 to 12 amino acids. Each of boxes A, B and C is encoded by a separate exon. Alternative exon usage of the A, B and C boxes, and transcription from internal promoters, can result in PFM transcripts and polypeptides containing all, some or none of the A, B or C boxes.

PFM nucleic acid molecules and encoded polypeptides additionally contain a zinc finger domain, or "ZF domain." Generally, the ZF domain contains one or several C2H2 or Krüppel-like Zinc finger motifs, which can be represented by the structure: Cys-X2-Cys-X12-His-X3-His. However, a zinc finger motif of a PFM can have an amino acid other than Cys or His at one or more of the four conserved positions, and/or alternative spacings between the four conserved positions. The zinc finger motif is found in at least 300 human genes, and is known to specifically bind DNA or RNA sequences (Bellefroid et al., *DNA* 8:377-387 (1989)).

The PFM nucleic acid molecules and polypeptides of the invention are designated PFM1, PFM2, mPFM2a, mPFM2b, PFM3a, PFM3b, PFM4 and PFM5. The nucleotide sequences of these PFM nucleic acid molecules are shown in FIGS. 1A-8A, respectively, and are set forth as SEQ ID NO:1 (PFM1); SEQ ID NO:3 (PFM2); SEQ ID NO:5 (mPFM2a); SEQ ID NO:7 (mPFM2b); SEQ ID NO:9 (PFM3a); SEQ ID NO:11 (PFM3b); SEQ ID NO:13 (PFM4); and SEQ ID NO:15 (PFM5). The amino acid sequences of the encoded PFM polypeptides are also shown in FIGS. 1B-8B, respectively, and are set forth as SEQ ID NO:2 (PFM1); SEQ ID NO:4 (PFM2); SEQ ID NO:6 (mPFM2a); SEQ ID NO:8 (mPFM2b) SEQ ID NO:10 (PFM3a); SEQ ID NO:12 (PFM3b) SEQ ID NO:14 (PFM4); and SEQ ID NO:16 (PFM5).

The nucleotide (nt) boundaries of the PR domains, and of the A, B and C boxes thereof, of PFM1, PFM2, mPFM2a, PFM3a, PFM4 and PFM5, with respect to the sequences shown in FIGS. 1A, 2A, 3A, 5A, 7A and 8A, respectively, with their corresponding SEQ ID NOS, are provided in Table 1, below. The amino acid (aa) boundaries of the PR domains, and of the A, B and C boxes thereof, of PFM1, PFM2, mPFM2a, PFM3a, PFM4 and PFM5, with respect to the sequences shown in FIGS. 1B, 2B, 3B, 5B, 7B and 8B, respectively, with their corresponding SEQ ID NOS, are also provided in Table 1, below.

TABLE 1

| PFM | PR DOMAIN | A BOX | B BOX | C BOX |
|---|---|---|---|---|
| PFM1 | nt 1372–1740 | nt 1420–1455 | nt 1549–1584 | nt 1690–1707 |
|  | (SEQ ID NO:17) | (SEQ ID NO:29) | (SEQ ID N0:31) | (SEQ ID NO:33) |
|  | aa 412–534 | aa 428–439 | aa 471–482 | aa 518–523 |
|  | (SEQ ID NO:18) | (SEQ ID NO:30) | (SEQ ID NO:32) | (SEQ ID NO:34) |
| PFM2 | nt 172–402 | NOT APPLICABLE | nt 229–264 | nt 370–387 |
|  | (SEQ ID NO:19) |  | (SEQ ID NO:35) | (SEQ ID NO:37) |
|  | aa 1–77 |  | aa 20–31 | aa 67–72 |
|  | (SEQ ID NO:20) |  | (SEQ ID NO:36) | (SEQ ID NO:38) |
| mPFM2a | nt 118–474 | nt 163–198 | nt 289–324 | nt 430–447 |
|  | (SEQ ID NO:21) | (SEQ ID NO:39) | (SEQ ID NO:41) | (SEQ ID NO:43) |
|  | aa 14–131 | aa 29–40 | aa 71–82 | aa 118–123 |
|  | (SEQ ID NO:22) | (SEQ ID NO:40) | (SEQ ID NO:42) | (SEQ ID NO:44) |
| PFM3a | nt 652–1020 | nt 699–735 | nt 832–867 | nt 973–990 |
|  | (SEQ ID NO:23) | (SEQ ID NO:45) | (SEQ ID NO:47) | (SEQ ID NO:49) |
|  | aa 218–340 | aa 234–245 | aa 277–289 | aa 325–330 |
|  | (SEQ ID NO:24) | (SEQ ID NO:46) | (SEQ ID NO:48) | (SEQ ID NO:50) |
| PFM4 | nt 277–618 | nt 332–357 | nt 436–471 | nt 577–594 |
|  | (SEQ ID NO:25) | (SEQ ID NO:51) | (SEQ ID NO:53) | (SEQ ID NO:55) |
|  | aa 46–159 | aa 61–72 | aa 99–110 | aa 146–151 |
|  | (SEQ ID NO:26) | (SEQ ID NO:52) | (SEQ-ID NO:54) | (SEQ ID NO:56) |
| PFM5 | nt 1306–1647 | nt 1336–1368 | nt 1453–1500 | nt 1606–1623 |
|  | (SEQ ID NO:27) | (SEQ ID NO:57) | (SEQ ID NO:59) | (SEQ ID NO:61) |
|  | aa 25–138 | aa 35–45 | aa 74–89 | aa 125–130 |
|  | (SEQ ID NO:28) | (SEQ ID NO:58) | (SEQ ID NO:60) | (SEQ ID NO:62) |

When the PFM polypeptides of the invention are aligned with other PFM polypeptides, including RIZ1, BLIMP1 and MDS1-EVI1, it is apparent that there is a region of sequence similarity that extends beyond the A, B and C boxes set forth in Table I. The amino acid (aa) boundaries of the region of sequence similarity including and extending beyond the A, B and C boxes of the PR domains of PFM1, PFM2, mPFM2a, PFM3a, PFM4 and PFM5 are shown by italics in FIGS. 1B, 2B, 3B, 5B, 7B and 8B, respectively.

The nucleotide (nt) boundaries of the zinc finger (ZF) domains of PFM1, PFM2, mPFM2a, PFM3a, PFM4 (2 separate domains) and PFM5, with respect to the sequences shown in FIGS. 1A, 2A, 3A, 5A, 7A and 8A, respectively, with their corresponding SEQ ID NOS, are provided in Table 2, below. The amino acid (aa) boundaries of the ZF domains of PFM1, PFM2, mPFM2a, PFM3a, PFM4 (2 separate domains) and PFM5, with respect to the sequences shown in FIGS. 1B, 2B, 3B, 5B, 7B and 8B, respectively, with their corresponding SEQ ID NOS, are also provided in Table 2, below. The amino acid (aa) boundaries of each of the individual zinc finger motifs within the ZF domains of PFM1, PFM2, mPFM2a, PFM3a, PFM4 and PFM5 are shown by underlining in FIGS. 1B, 2B, 3B, 5B, 7B and 8B, respectively.

TABLE 2

| PFM | Zinc Finger Domain (nucleotides) | Zinc Finger Domain (amino acids) |
| --- | --- | --- |
| PFM1 | nt 1897–2379 (SEQ ID NO:63) | aa 587–747 (SEQ ID NO:64) |
| PFM2 | nt 523–1047 (SEQ ID NO:65) | aa 118–292 (SEQ ID NO:66) |
| mPFM2a | nt 634–2005 (SEQ ID NO:67) | aa 186–642 (SEQ ID NO:68) |
| PFM3a | nt 1321–1635 (SEQ ID NO:69) | aa 441–545 (SEQ ID NO:70) |
| PFM4 | nt 691–756 (SEQ ID NO:71) | aa 184–205 (SEQ ID NO:72) |
|  | nt 1099–1329 (SEQ ID NO:73) | aa 320–396 (SEQ ID NO:74) |
| PFM5 | nt 1702–1767 (SEQ ID NO:75) | aa 157–178 (SEQ ID NO:76) |

Both PFM2 and mPFM2a polypeptides contain a sequence motif, LXCXE, which is also present in RIZ gene products. The LXCXE motif is known to bind the retinoblatoma (Rb) tumor suppressor gene product (Buyse et al., *J. Virol.* 71:6200-62-3 (1997)). The LXCXE motif in PFM2 has the sequence LGCKE (SEQ ID NO:89), which corresponds to amino acids 110-114 of the sequence shown in FIG. 2B, and is encoded by nucleotides 498-513 (SEQ ID NO:88) of the sequence shown in FIG. 2A. The LXCXE motif in mPFM2a has the sequence LGCEE (SEQ ID NO:91), which corresponds to amino acids 178-182 of the sequence shown in FIG. 3B, and is encoded by nucleotides 610-624 (SEQ ID NO:90) of the sequence shown in FIG. 3A.

PFM4 additionally contains a domain of approximately 100 amino acids having about 35-40% identity to the KRAB-domain-containing zinc finger protein 133 (ZNF133). This domain is designated PKZL, for "PR and KRAB zinc finger protein-linked." The PKZL domain of PFM4 corresponds to amino acids 207-306 of the sequence shown in FIG. 7B, and is encoded by nucleotides 760-1059 of the sequence shown in FIG. 7A. The PKZL domain likely is important in mediating protein-protein interactions with cellular regulatory molecules.

The PKZL domain is also found in two other KRAB-domain-containing zinc finger proteins, designated PKZL1 and PKZL2. The nucleotide sequence of PKZL1 (SEQ ID NO:77) is shown in FIG. 9A, and the encoded amino acid sequence of PKZL1 (SEQ ID NO:78) is shown in FIG. 9B. The nucleotide sequence of PKZL2 (SEQ ID NO:79) is shown in FIG. 10A, and the encoded amino acid sequence of PKZL2 (SEQ ID NO:80) is shown in FIG. 10B. The amino acid (aa) boundaries of the KRAB Domain, PKZL and ZF domains of PKZL1 and PKZL2, with respect to the sequences shown in FIGS. 9B and 10B, respectively, are provided in Table 3, below.

TABLE 3

| PKZL | KRAB Domain | PKZL Domain | ZF Domain |
| --- | --- | --- | --- |
| PKZL1 | aa 9–65 | aa 99–192 | aa 197–509 |
| PKZL2 | aa 1–39 | aa 63–172 | aa 204–515 |

The cDNA structures of PFM1, PFM2, mPFM2a, mPFM2b, PFM3a, PFM3b, PFM4 and PFM5, with the boundaries of their PR domains, A, B and C boxes, zinc finger motifs, LXCXE motif, and PKZL domain indicated, are schematically depicted in FIGS. 11A, 12A, 13A, 14 and 15A.

Figure 12A:
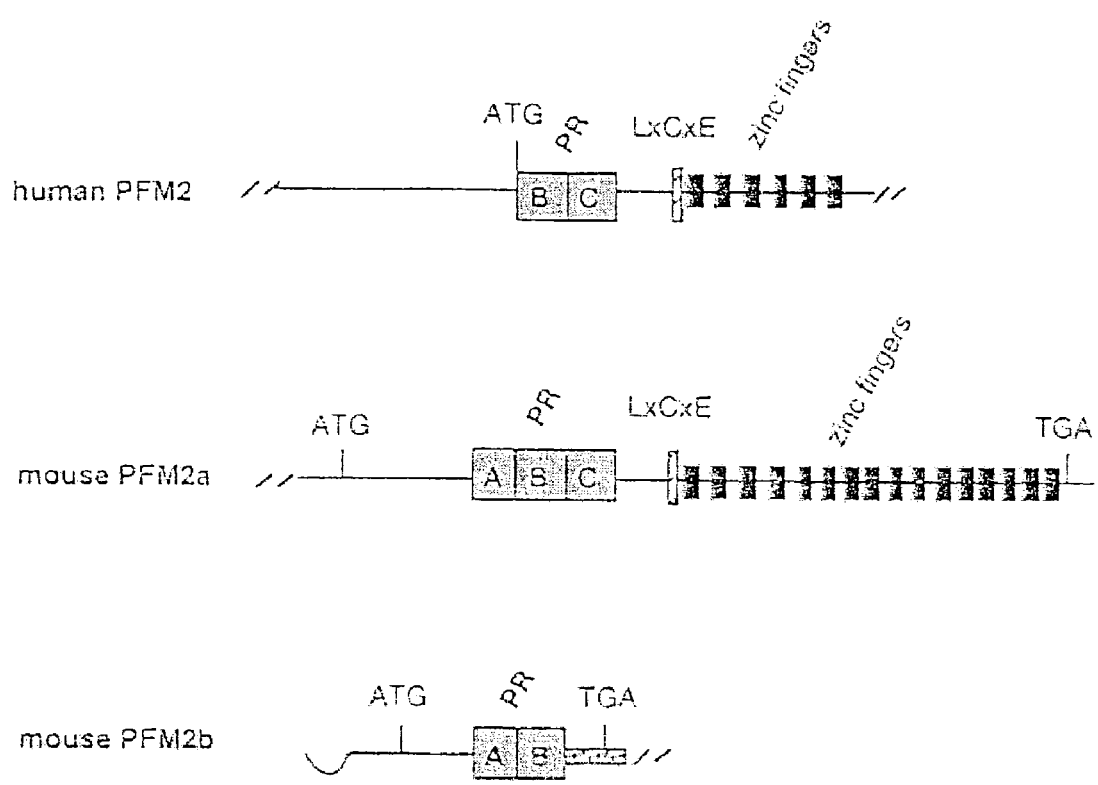
FIG. 12A shows a schematic representation of the structure of PFM2, mPFM2a and mPFM2b.
Figure 14:
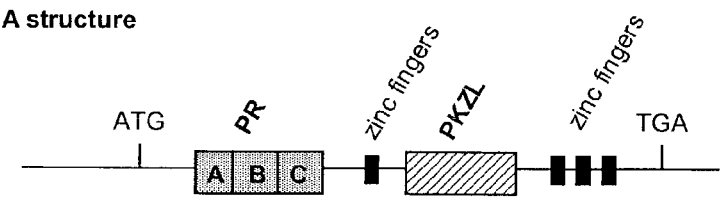
FIG. 14 shows a schematic representation of the structure of PFM4.

As shown in FIGS. 12A and 13A, certain of the PFM genes disclosed herein exist as alternatively spliced products. For example, the PFM2 sequence disclosed herein lacks the PR domain A box. The mPFM2 exists as a PR+ form, namely mPFM2a, and a PR– form lacking the PR domain C box, namely mPFM2b. Likewise, PFM3 exists as a PR+ form, namely PFM3a, and a PR– form lacking the PR domain B and C boxes. Additionally, as described further in the Examples, below, mRNA transcripts of several different sizes are observed for certain of the PFM genes, consistent with alternative exon usage.

The PFM genes disclosed herein are localized to regions of human chromosomes predicted to harbor tumor suppressor genes, because deletion of these regions is closely associated with various human tumors. In particular, PFM1 localizes to chromosome band 12q23-q24.1, a region commonly deleted in ovarian cancer, pancreatic cancer and gastric cancer; PFM2 localizes to chromosome band 4q25-4q26, a region commonly deleted in ovarian cancer, breast cancer, lung cancer and hepatoma; PFM3 localizes to chromosome band 5q21, a region often deleted in ovarian cancer, colon cancer, lung cancer and gastric cancer; PFM4 localizes to chromosome band 16q24, a region deleted in prostate cancer, breast cancer, ovarian cancer and hepatoma; and PFM5 localizes to chromosome band 4q21.1, which is deleted in mesothelioma, lung cancer, colon cancer and hepatoma. These observations are consistent with a role for these PFMs as tumor suppressors.

PFM Nucleic Acid Molecules

The invention provides isolated PFM nucleic acid molecules. The isolated PFM nucleic acid molecules of the invention can be used in a variety of diagnostic and therapeutic applications. For example, as described in more detail below, the isolated PFM nucleic acid molecules of the invention can be used as probes and primers to detect PFM nucleic acid molecules in samples; as templates for the recombinant expression of PFM polypeptides; in two-hybrid assays to identify cellular molecules that bind PFM; and in in vivo and ex vivo gene therapy applications to positively or negatively modulate cell proliferation.

In one embodiment, the invention provides an isolated PFM nucleic acid molecule containing a PFM PR domain nucleotide sequence selected from the group consisting of SEQ ID NOS:17, 19, 21, 23, 25 and 27. In another embodiment, the invention provides an isolated PFM nucleic acid molecule containing a PFM ZF domain nucleotide sequence selected from the group consisting of SEQ ID NOS:63, 65, 67, 69, 71, 73 and 75. Modifications of these sequences that hybridizes thereto under moderately stringent conditions, and modifications of these sequences having at least 60% identity thereto are also provided.

Exemplary isolated PFM nucleic acid molecules provided by the invention that contain a PFM PR domain or that contain a PFM ZF domain are nucleic acid molecules having the sequence of SEQ ID NOS:1, 3, 5, 7, 8, 11, 13 or 15, or modification thereof that hybridizes thereto under moderately stringent conditions.

Other exemplary isolated PFM nucleic acid molecules of the invention contain both the PR domain and the ZF domain of a PFM, as set forth above, and, optionally, can also contain PFM sequence between the PR domain and the ZF domain.

The term "isolated," in reference to a PFM nucleic acid molecule is intended to mean that the molecule is substantially removed or separated from components with which it is naturally associated, or otherwise modified by the hand of man. Thus, the term "isolated PFM nucleic acid molecule" excludes PFM nucleic acid molecules as they exist in nature.

The term "nucleic acid molecule," as used herein, refers to an oligonucleotide or polynucleotide of natural or synthetic origin. A nucleic acid molecule can be single- or double-stranded genomic DNA, cDNA or RNA, and can represent the sense strand, the antisense strand, or both.

The term "moderately stringent conditions," as used herein, refers to hybridization conditions that permit a nucleic acid molecule to bind a nucleic acid that has substantial identity to the recited sequence. Moderately stringent conditions are conditions equivalent to hybridization of filter-bound nucleic acid in 50% formamide, 5× Denhart's solution, 5×SSPE, 0.2% SDS at 42° C., followed by washing in 0.2×SSPE, 0.2% SDS, at 50°. In contrast, "highly stringent conditions" are conditions equivalent to hybridization of filter-bound nucleic acid in 50% formamide, 5× Denhart's solution, 5×SSPE, 0.2% SDS at 42° C., followed by washing in 0.2×SSPE, 0.2% SDS, at 65°. Other suitable moderately stringent and highly stringent hybridization buffers and conditions are well known to those of skill in the art and are described, for example, in Sambrook et al., *Molecular Cloning: A Laboratory Manual*, Cold Spring Harbor Laboratory, New York (1992) and in Ansubel et al., *Current Protocols in Molecular Biology*, John Wiley and Sons, Baltimore, Md. (1998).

In general, a nucleic acid molecule that hybridizes to a recited sequence under moderately stringent conditions will have greater than about 60% identity, such as greater than about 70% identity, preferably greater than about 80% identity to the reference sequence over the length of the two sequences being compared. A nucleic acid molecule that hybridizes to a recited sequence under highly stringent conditions will generally have greater than about 90% identity, including greater than about 95% identity, to the reference sequence over the length of the two sequences being compared. Identity of any two nucleic acid sequences can be determined by those skilled in the art based, for example, on a BLAST 2.0 computer alignment, using default parameters. BLAST 2.0 searching is available at www.ncbi.nlm.nih.gov/gorf/bl2.html., as described by Tatiana et al., *FEMS Microbiol Lett.* 174:247-250 (1999).

Thus, a "modification" of a reference nucleic acid sequence can include one or several nucleotide additions, deletions, or substitutions with respect to the recited sequence. Such modifications can correspond to variations that are made deliberately, or which occur as mutations during nucleic acid replication.

Exemplary "modifications" of the recited PFM sequences include sequences that correspond to homologs of other species, such as primates, mouse, rat, rabbit, bovine, porcine, ovine, canine or feline species. The sequences of corresponding PFMs of non-human species can be determined by methods known in the art, such as by PCR or by screening genomic, cDNA or expression libraries.

Furthermore, exemplary "modifications" of the recited PFM can correspond to splice variant forms of recited PFM sequences. Thus, for example, a modification of a PFM nucleic acid molecule of the invention can lack one or more of the exons that encode the A, B or C boxes of the PR domain. Exon usage by splice variants of PFM nucleic acid molecules can be readily determined by those skilled in the art by comparing the sequence of the PFM cDNA to the sequence of the corresponding PFM genomic DNA.

Additionally, a "modification" of a reference sequence can include one or more non-native nucleotides, having, for example, modifications to the base, the sugar, or the phosphate portion, or having a modified phosphodiester linkage. Such modifications can be advantageous in increasing the stability of the nucleic acid molecule.

Furthermore, a "modification" of a reference sequence can include, for example, a detectable moiety, such as a radiolabel, a fluorochrome, a ferromagnetic substance, a luminescent tag or a detectable binding agent such as biotin. Such modifications can be advantageous in applications where detection of a PFM nucleic acid molecule is desired.

In another embodiment, the invention provides an isolated PFM nucleic acid molecule containing a nucleotide sequence that encodes a PFM PR domain polypeptide having an amino acid sequence selected from the group consisting of SEQ ID NOS:18, 20, 22, 24, 26 and 28. In a further embodiment, the invention provides a PFM ZF domain polypeptide having an amino acid sequence selected from the group consisting of SEQ ID NOS:64, 66, 68, 70, 72, 74 and 76. Nucleic acid molecules having nucleic acid sequences that encode modified polypeptides that are immunologically equivalent to the recited PFM amino acid sequences are also provided. The term "immunologically equivalent" is described further below in regard to PFM polypeptides.

The term "isolated PFM nucleic acid molecule" specifically excludes nucleic acid molecules consisting of certain nucleotide sequences, such as Expressed Sequence Tags (ESTs), Sequence Tagged Sites (STSs) and genomic fragments, deposited in public databases such as the nr, dbest, dbsts, gss and htgs databases, which are available for searching at www.ncbi.nlm.nih.gov/blast/blast.cgi?J-form=0, using the program BLASTN 2.0.9 [May-07-1999] described by Altschul et al., *Nucleic Acids Res.* 25:3389-3402 (1997).

In particular, the term "PFM nucleic acid molecule" specifically excludes nucleic acid molecules consisting of any of the nucleotide sequences having the Genbank (gb), EMBL (emb) or DDBJ (dbj) Accession numbers set forth in Table 4, below:

TABLE 4

| PFM | PR domain | ZF domain |
|---|---|---|
| PFM1 | gb|AC007622.10; gb|AQ680319.1; gb|AQ589875.1; gb|T07037; dbj|D77868; gb|W95618 | gb|AI767612.1; gb|AI200380; gb|AI031897; gb|AI274279; gb|AA564783; gb|AA052953; gb|AI206448; gb|W95619; gb|T75408; gb|R14633; emb|F13077; gb|T67867; gb|AA074438; emb|F08157; gb|AA361586; gb|W95618; gb|AI422938.1; |

TABLE 4-continued

| PFM | PR domain | ZF domain |
|---|---|---|
| | | gb\|AA547654; gb\|AI422940; gb\|AA542340; gb\|AA151863; gb\|W23287; gb\|AC007622.10; gb\|B90692; gb\|AQ119702 |
| PFM2 | gb\|AA917968; gb\|AI528057; gb\|AA884744; gb\|AI315936; gb\|AI049009; gb\|AI197291; | gb\|AQ491694.1; emb\|X96881; |
| mPFM2 | gb\|AI315936; gb\|AI528057; gb\|AI049009; gb\|AA917968; gb\|AA884744; gb\|AI197291; gb\|AI521783.1; | emb\|X96881; gb\|AI893133.1; gb\|W11621; gb\|AA511711; gb\|AI894176.1; gb\|AI314715; gb\|AI785273.1; gb\|W33556; dbj\|AU018120; dbj\|AU017087; gb\|M79273; gb\|AA014148; gb\|AI854760.1; gb\|AI894050.1; gb\|AQ451739.1; gb\|AQ480567.1; gb\|AQ120015; gb\|AQ491694.1; |
| PFM3 | gb\|AI243539; gb\|AI324149; gb\|AI914660.1; gb\|AI322509; gb\|AI348223; gb\|AA917645; gb\|N29774; gb\|AA008751; gb\|AA018011; gb\|AC008606.1 | gb\|AI862130.1; gb\|AA546652; gb\|N83355; gb\|AA917645; gb\|AI322509; gb\|AA018011; gb\|AA008751; gb\|AC008606.1 |
| PFM4 | gb\|AC007046.1; gb\|AF03975 | gb\|AC007046.1; emb\|Z96314; gb\|AF114816.1; gb\|AF114817.1; emb\|AL049650.8; gb\|M20675; gb\|U28251; emb\|AL031673.16; emb\|AL049942.1; emb\|Z98745; gb\|AC005678; gb\|AQ772417.1; gb\|AQ266860.1; emb\|AL047439.1; gb\|T88890; gb\|T09047; gb\|AA341469; gb\|AI810272.1; gb\|T70255; gb\|W85779; gb\|T23204; gb\|AA385857; gb\|AI603959.1; gb\|AA612532; |
| PFM5 | gb\|AI570404.1; gb\|AI594999.1; gb\|AA056286; gb\|H43774; gb\|AA054104; gb\|H83463; gb\|R88858; | gb\|AI594999.1; gb\|G18801 |

The invention also provides isolated PFM oligonucleotides containing at least 15 contiguous nucleotides of PFM1, hPFM2, mPFM3, PFM4, or PFM5. As used herein, the term "oligonucleotide" refers to a nucleic acid molecule that includes at least 15 contiguous nucleotides from the reference nucleotide sequence, can include at least 16, 17, 18, 19, 20 or at least 25 contiguous nucleotides, and often includes at least 30, 40, 50, 60, 70, 80, 90, 100, 125, 150, 175, 200, 225, 250, 275, 300, 325, up to 350 contiguous nucleotides from the reference nucleotide sequence.

In one embodiment, the isolated PFM oligonucleotides contain a nucleotide sequence that encodes a PR domain A, B, or C box. Thus, the invention provides isolated oligonucleotides containing a nucleotide sequence selected from the group consisting of SEQ ID NOS:29, 31, 33, 35, 37, 39, 41, 43, 45, 47, 49, 51, 53, 55, 57, 59 and 61.

In another embodiment, the invention provides isolated PFM oligonucleotides that contain a nucleotide sequence that encodes one or more ZF domain zinc finger motifs. The PFM zinc finger motifs of PFM nucleic acid molecules are underlined in FIGS. 1B, 2B, 3B, 5B, 7B and 8B.

In yet another embodiment, the invention provides an isolated PFM oligonucleotide that contains at least a part of the nucleotide sequence that encodes the PKZL domain of PFM4, which is nucleotides 760-1059 of the sequence shown in FIG. 7A.

In a further embodiment, the invention provides isolated PFM oligonucleotides that contain a nucleotide sequence that encodes the RB-binding LXCXE motif of PFM2 or mPFM2. Thus, the invention provides an oligonucleotide selected from the group consisting of SEQ ID NOS:88 and 90.

The PFM oligonucleotides of the invention that contain at least 15 contiguous nucleotides from the reference PFM nucleotide sequence are able to hybridize to PFM under moderately stringent hybridization conditions and thus can be advantageously used, for example, as probes to detect PFM DNA or RNA in a sample, and to detect splice variants thereof that contain or lack particular PFM domains; as sequencing or PCR primers; as antisense reagents to block transcription of PFM RNA in cells; or in other applications known to those skilled in the art in which hybridization to a PFM is desirable.

In one embodiment, the invention provides oligonucleotides containing at least 15 contiguous PFM nucleotides that are able to "specifically hybridize" with a PFM nucleic acid molecule. As used herein, the term "specifically hybridize" refers to the ability of a nucleic acid molecule to hybridize, under moderately stringent conditions as described above, to the reference PFM nucleic acid molecule, without hybridization under the same conditions with nucleic acid molecules that are not PFMs, such as actin cDNA.

In one embodiment, the invention provides a primer pair for detecting PFM nucleic acid. The primer pair contains two PFM oligonucleotides. The primer pair can be used, for example, to amplify PFM DNA by RT-PCR or PCR. Exemplary PFM primer pairs and their uses are provided in Examples I-III and V, below.

The isolated PFM nucleic acid molecules and oligonucleotides of the invention can be produced or isolated by methods known in the art. The method chosen will depend, for example, on the type of nucleic acid molecule one intends to isolate. Those skilled in the art, based on knowledge of the nucleotide sequences disclosed herein, can readily isolate PFM nucleic acid molecules as genomic DNA, or desired introns, exons or regulatory sequences therefrom; as full-length cDNA or desired fragments therefrom; or as full-length mRNA or desired fragments therefrom, by methods known in the art.

One useful method for producing an isolated PFM nucleic acid molecule of the invention involves amplification of the nucleic acid molecule using the polymerase chain reaction (PCR) and PFM-specific primers and, optionally, purification of the resulting product by gel electrophoresis. Either PCR or reverse-transcription PCR (RT-PCR) can be used to produce a PFM nucleic acid molecule having any desired nucleotide boundaries. Desired modifications to the nucleic acid sequence can also be introduced by choosing an appropriate primer with one or more additions, deletions or substitutions. Such nucleic acid molecules can be amplified exponentially starting from as little as a single gene or mRNA copy, from any cell, tissue or species of interest.

A futher method of producing an isolated PFM nucleic acid molecule of the invention is by screening a library, such as a genomic library, cDNA library or expression library, with a detectable agent. Such libraries are commercially available or can be produced from any desired tissue, cell, or species of interest using methods known in the art. For example, a cDNA or genomic library can be screened by hybridization with a detectably labeled nucleic acid molecule having a nucleotide sequence disclosed herein. Additionally, an expression library can be screened with an antibody raised against a polypeptide corresponding to the coding sequence of a PFM nucleic acid disclosed herein. The library clones containing PFM molecules of the invention can be isolated from other clones by methods known in the art and, if desired, fragments therefrom can be isolated by restriction enzyme digestion and gel electrophoresis.

Furthermore, isolated PFM nucleic acid molecules and oligonucleotides of the invention can be produced by synthetic means. For example, a single strand of a nucleic acid molecule can be chemically synthesized in one piece, or in several pieces, by automated synthesis methods known in the art. The complementary strand can likewise be synthesized in one or more pieces, and a double-stranded molecule made by annealing the complementary strands. Direct synthesis is particularly advantageous for producing relatively short molecules, such as oligonucleotide probes and primers, and nucleic acid molecules containing modified nucleotides or linkages.

The invention also provides a vector containing an isolated PFM nucleic acid molecule. The vectors of the invention are useful for subcloning and amplifying an isolated PFM nucleic acid molecule, and for recombinantly expressing a PFM polypeptide. A vector of the invention can include a variety of elements useful for cloning and/or expression of PFM nucleic acid molecules, such as enhancer sequences and promoter sequences from a viral, bacterial or mammalian gene, which provide for constitutive, inducible or cell-specific RNA transcription; transcription termination and RNA processing signals, including polyadenylation signals, which provide for stability of a transcribed mRNA sequence; an origin of replication, which allows for proper episomal replication; selectable marker genes, such as a neomycin or hygromycin resistance gene, useful for selecting stable or transient transfectants in mammalian cells, or an ampicillan resistance gene, useful for selecting transformants in prokaryotic cells; and versatile multiple cloning sites for inserting nucleic acid molecules of interest.

Cloning vectors of the invention include, for example, viral vectors such as a bacteriophage, a baculovirus or a retrovirus; cosmids or plasmids; and, particularly for cloning large nucleic acid molecules, bacterial artificial chromosome vectors (BACs) and yeast artificial chromosome vectors (YACs). Such vectors are commercially available, and their uses are well known in the art.

If it is desired to express PFM RNA transcripts or polypeptides, a PFM nucleic acid molecule can be inserted into an expression vector such that it is operatively linked to a promoter of RNA transcription. The term "operatively linked," as used herein, is intended to mean that the nucleic acid molecule is positioned with respect to a PFM promoter, or heterologous promoter, in such a manner that the promoter will direct the transcription of RNA using the nucleic acid molecule as a template. Methods for operatively linking a nucleic acid to a desired promoter are well known in the art and include, for example, cloning the nucleic acid into a vector containing the desired promoter, or appending the promoter to a nucleic acid sequence using PCR. Thus, an expression vector containing a PFM nucleic acid molecule operatively linked to a promoter of RNA transcription can be used to express PFM transcripts and polypeptides in a desired host cell, or in an in vitro system, such as an extract or lysate that supports transcription and translation. Contemplated expression vectors include vectors containing regulatory sequences known in the art to provide for expression in bacterial cells, yeast cells, insect cells, mammalian cells and other vertebrate cells.

A variety of expression vectors are commercially available, and can be further modified, if desired, to include appropriate regulatory elements to provide for the desired level of expression or replication in the host cell. For example, appropriate promoter and enhancer elements can be chosen to provide for constitutive, inducible or cell type-specific expression. Useful constitutive promoter and enhancer elements for expression of PFM in mammalian cells include, for example, RSV, CMV, SV40 and IgH elements. An exemplary inducible expression element is a steroid response element, while an exemplary cell-specific expression element is a prostate specific antigen (PSA) regulatory sequence. Other constitutive, inducible and cell type-specific regulatory elements are well known in the art.

Exemplary host cells that can be used to express recombinant PFM molecules include mammalian primary cells; established mammalian cell lines, such as COS, CHO, HeLa, NIH3T3, HEK 293-T and PC12 cells; amphibian cells, such as Xenopus embryos and oocytes; and other vertebrate cells. Exemplary host cells also include insect cells (e.g. *Drosophila*), yeast cells (e.g. *S. cerevisiae, S. pombe,* or *Pichia pastoris*) and prokaryotic cells (e.g. *E. coli*).

Methods for introducing a cloning or expression vector into a host cell are well known in the art and include, for example, various methods of transfection such as calcium phosphate, DEAE-dextran and lipofection methods, viral transduction, electroporation and microinjection. Host cells expressing PFM nucleic acid molecules can be used, for example, as a source to isolate recombinantly expressed PFM polypeptides, to identify and isolate molecules that regulate or interact with PFM nucleic acids and polypeptides, or to screen for compounds that enhance or inhibit the activity of a PFM molecule of the invention, as described further below.

The methods of isolating, cloning and expressing nucleic acid molecules of the invention referred to herein are routine in the art and are described in detail, for example, in Sambrook et al., *Molecular Cloning: A Laboratory Manual*, Cold Spring Harbor Laboratory, New York (1992) and in Ansubel et al., *Current Protocols in Molecular Biology*, John Wiley and Sons, Baltimore, Md. (1998), which are incorporated herein by reference.

PFM Polypeptides

The invention also provides isolated PFM polypeptides. The isolated PFM polypeptides of the invention can be used in a variety of diagnostic and therapeutic applications. For example, as described in more detail below, the isolated PFM polypeptides can be used to generate antibodies that can be used as reagents to detect PFM expression in a sample, or in screening methods to identify compounds and cellular molecules that bind PFM and modulate cell proliferation.

In one embodiment, the invention provides an isolated polypeptide, containing a PFM PR domain amino acid sequence selected from the group consisting of SEQ ID NOS:18, 20, 22, 24, 26 and 28. In another embodiment, the invention provides an isolated polypeptide, containing a PFM ZF domain amino acid sequence selected from the group consisting of SEQ ID NOS:64, 66, 68, 70, 72, 74 and 76. Also provided are modifications of these polypeptides that are immunologically equivalent thereto, or that have at least 60% identity thereto.

Exemplary isolated polypeptides provided by the invention that contain a PFM PR domain or that contain a PFM ZF domain are polypeptides having the sequence of SEQ ID NOS:2, 4, 6, 8, 10, 12, 14 or 16, or are immunologically equivalent modifications thereof.

Other isolated polypeptides provided by the invention contain both the PR domain and ZF domain of a PFM, as set forth above, and, optionally, contain PFM amino acid sequences between the PR domain and ZF domain.

The term "isolated," in reference to a PFM polypeptide of the invention, is intended to mean that the molecule is substantially removed or separated from components with which it is naturally associated, or otherwise modified by the hand of man. Thus, the term "isolated PFM polypeptide" excludes PFM polypeptides as they exist in nature.

As used herein, the term "immunologically equivalent," in reference to a PFM polypeptide of the invention, refers to an amino acid sequence that is capable of being recognized by an antibody that also specifically binds to the reference PFM sequence. The term "specifically binds," as used herein, refers to binding with high affinity to the subject polypeptide, and binding with substantially lower affinity to an unrelated polypeptide, such as bovine serum albumin. High affinity binding includes binding with a dissociation constant (Kd) of less than about $10^{-6}$ M, preferably less than about $10^{-7}$ M, such as less than about $10^{-8}$ M. Methods of determining binding affinity are well known in the art and are described, for example, in Harlow and Lane, *Antibodies: A Laboratory Manual*, Cold Spring Harbor Laboratory, New York (1989).

In general, an amino acid sequence that is immunologically equivalent to a PFM polypeptide of the invention will have greater than about 60% identity, such as greater than about 70% identity, preferably greater than about 80% identity to the reference sequence. Identity of any two amino acid sequences can be determined by those skilled in the art based, for example, on a BLAST 2.0 computer alignment, using default parameters.

Those skilled in the art understand that two polypeptides with a high percentage of identity over the entire sequence, or over a substantial portion of the sequence, are more likely to exhibit similar biological activities than two molecules with the same percentage identity over a shorter portion of the sequence. Furthermore, two polypeptides that fold into common epitope structures are also more likely to exhibit similar biological activities than two molecules that do not share a common three-dimensional structure. Accordingly, an amino acid sequence that is "immunologically equivalent" to a PFM polypeptide can further be "biologically equivalent" to a PFM polypeptide.

As used herein, the term "biologically equivalent" is intended to indicate that the polypeptide has one or more of the biological properties characteristic of the reference polypeptide. As disclosed herein, biological properties characteristic of PFM polypeptides include, for example, growth modulating activity, regulation of chromatin-mediated gene expression, specific binding to cellular proteins and specific binding to DNA.

Thus, a polypeptide that is a "modification" of a reference amino acid sequence can include one or more additions, deletions or substitutions with respect to the reference sequence. In particular, a modification can include a conservative substitution, such as substitution of an apolar amino acid with another apolar amino acid (such as replacement of leucine with isoleucine), or substitution of a charged amino acid with a similarly charged amino acid (such as replacement of a glutamic acid with an aspartic acid). A modification can also include a nonconservative change, wherein a substituted amino acid has different but sufficiently similar structural or chemical properties that permits such a substitution without adversely affecting the desired immunological or biological activity.

A "modification" of a reference amino acid sequence that is "immunologically equivalent" or "biologically equivalent" to the reference amino acid sequence can also be a chemical or enzymatic modification, including but not limited to replacement of hydrogen by an alkyl, acyl, or amino group; esterification of a carboxyl group with a suitable alkyl or aryl moiety; alkylation of a hydroxyl group to form an ether derivative; phosphorylation or dephosphorylation of a serine, threonine or tyrosine residue; or N- or O-linked glycosylation.

Exemplary "modifications" of the recited PFM sequences include sequences that correspond to homologs of other species, such as primates, mouse, rat, rabbit, bovine, porcine, ovine, canine or feline species. Furthermore, exemplary "modifications" of the recited PFM can correspond to splice variant forms, or internal translation products, of recited PFM sequences. Thus, for example, a modification of a PFM polypeptide of the invention can lack one or more of the A, B or C boxes of the PR domain.

Those skilled in the art can determine appropriate amino acid modifications for a given application. For example, a modification can serve to increase the stability, bioavailability, bioactiviy or immunogenicity of the polypeptide, or to facilitate its purification. Thus, introduction of a D-amino acid or an amino acid analog for its corresponding L-amino acid, or deletion of a lysine residue, can stabilize a polypeptide and reduce degradation. Addition of tag sequences, such as epitope tags, histidine tags, glutathione-S-transferase (GST) and the like, or addition of sorting sequences, can facilitate purification of a recombinant polypeptide. Addition of carrier sequences, such as keyhole lympet hemocyanin, can enhance recognition of the polypeptide by the immune system. Depending on the modification and the source of the polypeptide, the modification can be introduced into the polypeptide, or into the encoding nucleic acid sequence.

Computer programs known in the art can provide guidance in determining which amino acid residues can be modified as indicated above without abolishing the immunological activity or a desired biological activity of a PFM polypeptide (see, for example, Eroshkin et al., *Comput. Appl. Biosci.* 9:491-497 (1993)). Additionally, guidance in modifying amino acid sequences while retaining functional activity is provided by aligning homologous PFM polypeptides from various species. Those skilled in the art understand that evolutionarily conserved amino acid residues and domains are more likely to be important for maintaining biological activity than less well-conserved residues and domains.

In yet another embodiment, the invention provides an isolated PFM peptide, having at least 8 contiguous amino acids of SEQ ID NOS:2, 4, 6, 8, 10, 12, 14 or 16. As used herein, the term "PFM peptide" refers to a peptide having at least 8 contiguous amino acids of PFM, such as at least 10, 12, 15, 20 or 25 contiguous amino acids, preferably at least 30, 40 or 50 contiguous amino acids of PFM, up to the full-length protein minus one amino acid.

A peptide of such size contains at least one epitope specific to PFM, and can thus be used as an immunogen to produce PFM-specific antibodies, or as an antigen to purify PFM antibodies. PFM peptides that are likely to be antigenic or immunogenic can be predicted using methods and algorithms known in the art and described, for example, by Irnaten et al., *Protein Eng.* 11:949-955 (1998), and Savoie et al., *Pac. Symp. Biocomput.* 1999:182-189 (1999). Immunogenicity of the PFM peptides of the invention can be determined by methods known in the art, such as assay of a delayed-type hypersensitivity response in an animal sensitized to a PFM polypeptide, or by elicitation of PFM specific antibodies. Likewise, antigenicity of the PFM peptides of the invention can be determined by methods known in the art, such as by ELISA analysis, as described, for example, in Harlow and Lane, supra (1988).

The PFM peptides of the invention can also be used in screening methods to identify PFM-binding cellular molecules and modulatory compounds, as described further below.

In one embodiment, the invention provides PFM peptides having an amino acid sequence of an A, B or C box of a PFM PR domain. Thus, the invention provides PFM peptides selected from the group consisting of SEQ ID NOS:30, 32, 34, 36, 38, 40, 42, 44, 46, 48, 50, 52, 54, 56, 58, 60 and 62.

In another embodiment, the invention provides PFM peptides that contain an amino acid sequence of a PFM ZF domain zinc finger motif. The PFM zinc finger motifs are underlined in FIGS. 1B, 2B, 3B, 4B, 5B, 7B and 8B.

In yet another embodiment, the invention provides isolated PFM peptides that contain at least part of the amino acid sequence of the PKZL domain of PFM4, which is amino acids 207-306 of the sequence shown in FIG. 7B.

In a further embodiment, the invention provides isolated PFM peptides that contain the amino acid sequence of the LXCXE motif of PFM2 or mPFM2. Thus, the invention provides PFM peptides containing an amino acid sequence selected from the group consisting of SEQ ID NOS:89 and 91, such as containing the amino acid sequence DRLGCKEDY (SEQ ID NO:92) or the amino acid sequence GHLGCEEDF (SEQ ID NO:93).

The isolated PFM polypeptides and peptides of the invention can be prepared by methods known in the art, including biochemical, recombinant and synthetic methods. For example, PFM can be purified by routine biochemical methods from a cell or tissue source that expresses abundant amounts of the corresponding transcript or polypeptide. The diagnostic methods disclosed herein can be adapted for determining which cells and tissues, and which subcellular fractions therefrom, are appropriate starting materials. Biochemical purification can include, for example, steps such as solubilization of the appropriate tissue or cells, isolation of desired subcellular fractions, size or affinity chromatography, electrophoresis, and immunoaffinity procedures. The methods and conditions for biochemical purification of a polypeptide of the invention can be chosen by those skilled in the art, and purification monitored, for example, by an ELISA assay or a functional assay, such as a DNA-binding or protein-binding assay.

A PFM polypeptide or peptide having any desired boundaries, and a polypeptide having a modification to the native PFM amino acid sequences, can also be produced by recombinant methods. Recombinant methods involve expressing a nucleic acid molecule encoding the desired polypeptide or fragment in a host cell or cell extract, and isolating the recombinant polypeptide or fragment, such as by routine biochemical purification methods described above. To facilitate identification and purification of the recombinant polypeptide, it is often desirable to insert or add, in-frame with the coding sequence, nucleic acid sequences that encode epitope tags, polyhistidine tags, glutathione-S-transferase (GST) domains, and similar affinity binding sequences, or sequences that direct expression of the polypeptide in the periplasm or direct secretion. Methods for producing and expressing recombinant polypeptides in vitro and in prokaryotic and eukaryotic host cells are well known in the art.

Thus, the invention provides a method of isolating PFM polypeptide, by growing a host cell containing an expression vector encoding PFM polypeptide, under conditions appropriate for expression of the encoded PFM polypeptide, and isolating the PFM polypeptide.

The PFM polypeptide fragments and peptides of the invenition can also be produced, for example, by enzymatic or chemical cleavage of the full-length polypeptide. Methods for enzymatic and chemical cleavage and for purification of the resultant peptide fragments are well known in the art (see, for example, Deutscher, *Methods in Enzymology*, Vol. 182, "Guide to Protein Purification," San Diego: Academic Press, Inc. (1990), which is incorporated herein by reference).

Furthermore, PFM polypeptides and peptides can be produced by chemical synthesis. If desired, such as to optimize their functional activity, stability or bioavailability, such molecules can be modified to include D-stereoisomers, non-naturally occurring amino acids, and amino acid analogs and mimetics. Examples of modified amino acids and their uses are presented in Sawyer, *Peptide Based Drug Design*, ACS, Washington (1995) and Gross and Meienhofer, *The Peptides: Analysis, Synthesis, Biology*, Academic Press, Inc., New York (1983), both of which are incorporated herein by reference.

PFM Antibodies

The invention also provides an antibody or antigen binding fragment thereof which specifically binds a PFM polypeptide. Such antibodies can be used, for example, to affinity purify a PFM polypeptide from a cell or tissue source, or in therapeutic and diagnostic applications described below.

An "antigen binding fragment" of an antibody of the invention includes, for example, individual heavy or light chains and fragments thereof, such as VL, VH and Fd; monovalent fragments, such as Fv, Fab, and Fab'; bivalent fragments such as $F(ab')_2$; single chain Fv (scFv); and Fc fragments. Antigen binding fragments include, for example, fragments produced by protease digestion or reduction of an antibody, as well as fragments produced by recombinant DNA methods known to those skilled in the art.

The antibodies of the invention can be produced by any method known in the art. For example, a PFM polypeptide or immunogenic peptide of the invention, or a nucleic acid expressing such a polypeptide, can be administered to an animal, using standard methods, and polyclonal antibodies isolated therefrom. Such polypeptides of peptides, if desired, can be conjugated to a carrier, such as KLH, serum albumin, tetanus toxoid and the like, using standard linking techniques, to increase their immunogenicity. Additionally, such peptides can be formulated together with an adjuvant known in the art, such as Freund's complete or incomplete adjuvant. The antibodies so generated can be used in the form of serum isolated from an immunized animal, or the antibody can be affinity purified from the serum using PFM peptides or polypeptides.

Additionally, the PFM antibodies of the invention can be monoclonal antibodies produced by a hybridoma cell line, by chemical synthesis, or by recombinant methods. Modified antibodies, such as chimeric antibodies, humanized antibodies and CDR-grafted or bifunctional antibodies, can also be produced by methods well known to those skilled in the art.

Methods of preparing and using antibodies and antigen-binding fragments, including detectably labeled antibodies, are described, for example, in Harlow and Lane, *Antibodies: A Laboratory Manual*, Cold Spring Harbor Laboratory, New York (1989); in Day, E. D., *Advanced Immunochemistry*, Second Ed., Wiley-Liss, Inc., New York, N.Y. (1990); and in Borrebaeck (Ed.), *Antibody Engineering*, Second Ed., Oxford University Press, New York (1995), which are incorporated herein by reference.

PFM Modulatory Compounds

The invention also provides methods of identifying cellular and non-cellular molecules that modulate PFM expression and activity. These molecules can be used in ex vivo and in vivo therapeutic applications, as described further below, to promote or inhibit cell proliferation.

As disclosed herein, the PR domain of the PFM polypeptides of the invention functions as a specific protein binding domain. By specifically binding particular cellular proteins, the intact PR domain contributes to the function of PFM polypeptide as a suppressor of cell growth. Likewise, the LXCXE motif is known to bind RB and likely to bind other cellular proteins. The PKZL domain is also likely to bind cellular proteins. Thus, an isolated PFM polypeptide of the invention containing a PR domain, and LXCXE motif or a PKZL domain can be used, for example, in binding assays to identify cellular proteins that normally bind PFM.

Such cellular proteins are themselves likely to have positive or negative growth modulating activity and are also appropriate targets for therapeutic intervention to prevent or treat proliferative disorders. Furthermore, peptides or analogs corresponding to the PFM binding interface of such cellular proteins, or of PFM, can be administered as therapeutic compounds to specifically interfere with PFM function.

Various binding assays to identify cellular proteins that interact with protein binding domains are known in the art and include, for example, yeast two-hybrid screening assays (see, for example, Luban et al., *Curr. Opin. Biotechnol.* 6:59-64 (1995)) and affinity column chromatography methods using cellular extracts. By synthesizing or expressing polypeptide fragments containing various PFM sequences or deletions, the PFM binding interface can be readily identified.

As further disclosed herein, the zinc finger (ZF) domain of the PFM polypeptides of the invention functions as a specific DNA binding domain. By specifically binding particular DNA sequences, the ZF domain contributes to the function of PFM polypeptide as a suppressor of cell growth. Thus, an isolated PFM polypeptide of the invention containing a ZF domain, or one or more ZF motifs therefrom, can be used, for example, in binding assays to identify cellular DNA sequences that normally bind PFM. Such cellular DNA sequences are likely to be regulatory sequences for genes which themselves have positive or negative growth modulating activity, and which are appropriate targets for therapeutic invervention to prevent or treat proliferative disorders. Furthermore, oligonucleotides or analogs corresponding the PFM binding DNA sequences, can be administered as therapeutic compounds to specifically interfere with PFM function. Additionally, the ZF domain, or one or more ZF motifs therefrom, can be administered as therapeutic compounds to specifically interfere with PFM function.

Various assays to identify DNA sequences that bind DNA binding domains are known in the art and include, for example, Cyclic Amplification and Selection of Targets (CASTing), as described by Wright et al., *Mol. Cell. Biol.* 11:4104-4110 (1991), and the Multiplex Selection Technique (MuST), as described by Nallur et al., *Proc. Natl. Acad. Sci. USA* 93:1184-1189 (1996).

The invention also provides a method of identifying non-cellular molecules, or "PFM modulatory compounds," that modulate PFM expression or activity. As used herein, the term "PFM modulatory compound" refers to a molecule that specifically binds a PFM nucleic acid molecule or PFM polypeptide and alters its expression or activity. A PFM modulatory compound can be a Naturally occurring macromolecule, such as a peptide, nucleic acid, carbohydrate, lipid, or any combination thereof. A PFM modulatory compound also can be a partially or completely synthetic derivative, analog or mimetic of such a macromolecule, or a small organic or inorganic molecule prepared partly or completely by combinatorial chemistry methods.

Methods for producing pluralities of compounds to use in screening for PFM modulatory compounds, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422-428 (1998); Tietze et al., *Curr. Biol.*, 2:363-371 (1998); Sofia, *Mol. Divers.* 3:75-94 (1998); Eichler et al., *Med. Res. Rev.* 15:481-496 (1995); and the like. Libraries containing large numbers of natural and synthetic compounds also can be obtained from commercial sources.

A variety of low- and high-throughput assays known in the art are suitable for detecting specific binding interactions between a PFM nucleic acid molecule or polypeptide and a candidate PFM modulatory compound. Both direct and competitive assays can be performed, including, for example, fluorescence correlation spectroscopy (FCS) and scintillation proximity assays (SPA) reviewed in Major, *J. Receptor and Signal Transduction Res.* 15:595-607 (1995); and in Sterrer et al., *J. Receptor and Signal Transduction Res.* 17:511-520 (1997)). Other assays for detecting specific binding interactions include, for example, ELISA assays, FACS analysis, and affinity separation methods, which are described, for example, in Harlow and Lane, Eds., *Antibodies: A Laboratory Manual*, Cold Spring Harbor Laboratory (1988).

Assays to identify compounds that modulate PFM gene expression can involve first transducing cells with a PFM promoter-reporter nucleic acid construct such that a change in expression of a protein such as β-lactamase, luciferase, green fluorescent protein or β-galactosidase will be detected in response to contacting the cell with a PFM modulatory compound that upregulates or downregulates expression of PFM. Such assays and reporter systems are well known in the art and are described, for example, at www.aurorabio.com/tech_platform-assay_technologies.html (visited Aug. 5, 1999). Other assays to identify compounds that modulate PFM gene expression include assays that measure levels of PFM transcripts, such as Northern blots, RNase protection assays, and RT-PCR.

Assays to identify compounds that modulate PFM polypeptide expression can involve detecting a change in PFM polypeptide abundance in response to contacting the cell with a PFM modulatory compound. Assays for detecting changes in polypeptide expression include, for example, immunoassays with specific PFM antibodies, such as immunofluorescence, immunohistochemistry and immunoprecipitation assays.

Appropriate assays to determine whether a PFM modulatory compound affects PFM activity so as to inhibit or promote cell proliferation, can be determined by those skilled in the art. The skilled artisan appreciates that molecular pathways involved in cell proliferation are generally well conserved among eukaryotic organisms. Therefore, a proliferation assay can be performed in any eukaryotic cell type in which altered proliferation can be detected including, for example, primary mammalian cells, normal and transformed mammalian cell lines, yeast, insect cells and amphibian cells.

A molecule that modulates cell proliferation can, for example, cause cell cycle arrest at a particular stage of mitosis or meiosis, induce or prevent apoptosis, or promote progression through the cell cycle when normal cells would arrest. Such qualitative changes in the cell cycle can be determined by methods known in the art, and which depend on the cell type used in the assay. A molecule that modulates cell proliferation can also, for example, cause faster or slower progression through the cell cycle, resulting in an increased or decreased number of cells in the population after a given period of time. Those skilled in the art can choose an appropriate assay to determine whether, and by what mechanism, a molecule of the invention affects cell proliferation.

A molecule that modulates cell proliferation can also restore more normal proliferative characteristics to a neoplastic cell. Such a molecule can advantageously be used in therapeutic applications to prevent or treat cancer. To determine whether a molecule of the invention restores more normal proliferative characteristics on a neoplastic cell, an assay can be performed in a mammalian cell that exhibits neoplastic proliferative characteristics, such as soft agar colony formation, overgrowth of a cell monolayer, proliferation in low serum, abnormally rapid proliferation, or tumor formation in an animal. Such cells are known in the art and include both tumor cell lines and primary tumor cells. A molecule of the invention can be introduced or expressed in such a cell, and a determination can be made whether the molecule restores more normal proliferative characteristics to the cell, such as slower growth in culture, fewer foci, fewer soft agar colonies, or a reduction in tumor size, as compared to the parental cell.

Therapeutic Applications

As disclosed herein, PFM nucleic acid molecules encoding PFM polypeptides with intact PR domains inhibit cell growth. In contrast, PFM nucleic acid molecules encoding PFM polypeptides with partial PR domains, or lacking PR domains, promote cell growth. Thus, by selectively manipulating the expression or activity of either the PR+ or PR− forms of the PFM molecules of the invention, or both, it is readily apparent that cell growth can be modulated in either a positive or negative manner, as desired.

Accordingly, the invention provides PFM molecules and therapeutic methods that can be used to inhibit the growth of cells in culture, or in a subject. Advantageously, the molecules and therapeutic methods can be used to treat proliferative disorders in a subject. As used herein, the term "proliferative disorder" refers to a condition in which unwanted cell proliferation of one or more subset of cells in a mammal, such as a human, occurs, resulting in harm (e.g., discomfort or decreased life expectancy) to the mammal. Cell proliferative disorders include diseases such as cancer, in which the cells are neoplastically transformed, but also include diseases resulting from overgrowth of normal cells. For example, cell proliferative disorders include diseases associated with the overgrowth of connective tissues, such as various fibrotic diseases, including scleroderma, arthritis, alcoholic liver cirrhosis, keloid, and hypertropic scarring; vascular proliferative disorders, such as atherosclerosis; and benign tumors.

The invention also provides PFM molecules and therapeutic methods that can be used to enhance proliferation of normal cells. For some therapeutic applications, it may be useful to increase the proliferation of normal cells, without rendering the cells cancerous. In particular, in diseases of cell degeneration, such as Duchenne's muscular dystrophy, insulin-dependent diabetes mellitus, Parkinson's disease, Huntington's disease, Alzheimer's disease, paralysis, cerebellar atrophy, and the like, it may be useful to remove some of the remaining normal cells from the affected tissue of the individual, and culture the cells in large numbers ex vivo for reimplantation into the patient. Additionally, in applications such as wound healing and skin grafts, it is often desirable to increase the proliferation of normal cells.

In one embodiment, the invention provides a method for modulating cell growth, by introducing a vector containing an isolated PFM1, hPFM2, mPFM2, PFM3, PFM4 or PFM5 nucleic acid molecule of the invention, operatively linked to a promoter of RNA expression, into a host cell, and expressing the encoded PFM polypeptide in an amount effective to modulate growth of the cell. For applications in which inhibition of cell growth is desirable, expression vectors containing isolated full-length PFM nucleic acid molecules, or modifications of full-length PFM nucleic acid molecules that retain the growth inhibitory activity of PFM, can be introduced into cells under conditions in which the PFM polypeptide is expressed in an effective amount to inhibit cell proliferation. For applications in which promotion of cell growth is desirable, expression vectors which contain portions of the PFM nucleic acid molecules that compete with PFM for substrates or effectors, such as the PR domain or zinc finger domain, or both, can be introduced into cells under conditions in which the PFM polypeptide is expressed in an effective amount to promote cell proliferation.

Useful mammalian expression vectors for such therapeutic applications, and methods of introducing such vectors into mammalian cells either ex vivo or in vivo, for expression of the encoded polypeptide, are well known in the art. For example, a plasmid expression vector can be introduced into a cell by calcium-phosphate mediated transfection, DEAE-Dextran-mediated transfection, lipofection, polybrene- or polylysine-mediated transfection, electroporation, or by conjugation to an antibody, gramacidin S, artificial viral envelopes or other intracellular carriers. A viral expression vector can be introduced into a cell in an expressible form by infection or transduction, for example, or by encapsulation in a liposome. Appropriate viral vectors for gene therapy applications are well known in the art and include, for example, retroviruses, adenoviruses, adeno-associated viruses and herpes virus.

In another embodiment, the invention provides a method for modulating cell growth by introducing into a cell an effective amount of an antisense oligonucleotide or a ribozyme that inhibits expression of PFM, thereby modulating growth of the cell. Methods for modulating gene expression using antisense oligonucleotides and ribozymes are also well known in the art. Thus, an antisense molecule or ribozyme that selectively inhibits expression of the PR−, growth promoting form of PFM, can be used to inhibit cell proliferation. In contrast, an antisense molecule or ribozyme that selectively inhibits expression of the PR+, growth suppressing form of PFM, can be used to promote cell proliferation.

Antisense oligonucleotides that inhibit PFM gene expression generally are from about 15 to about 30 nucleotides in length, and often include sequences found within the first 30 nucleotides of the transcript being targeted. The preparation and use of antisense oligonucleotides are well known in the art and described in detail, for example, in Cohen (ed), *Oligonucleotides: Antisense Inhibitors of Gene Expression*, CRC Press Inc., Boca Raton (1989). Likewise, methods of preparing and using hairpin and hammerhead ribozymes for the selective inhibition of gene expression are known in the art and are described, for example, in Poeschla et al., *Curr. Opin. Oncol.* 6:601-606 (1994).

In a further embodiment, the invention provides a method for modulating cell growth by contacting the cell with an effective amount of a PEM modulatory compound. Methods of identifying PFM modulatory compounds have been described above.

In yet another embodiment, the invention provides a method for modulating cell growth by administering antibodies that specifically bind PFM. For example, antibodies that selectively detect a growth promoting structural variant of PFM, such as the PR− form of PFM polypeptide, can be administered to selectively target cells that express this variant. If desired, such antibodies can be administered in conjuction with a cytotoxic or cytostatic moiety, such as a radioisotope or toxin, in order to neutralize or kill cells expressing the desired structural variant.

The PFM therapeutic molecules of the invention described herein, including expression vectors, antisense oligonucleotides and ribozymes, PFM modulatory compounds, and antibodies, can optionally be formulated together with a pharmaceutically acceptable carrier for delivery to a cultured cell or to a subject. Suitable pharmaceutically accepable carriers are well known in the art and include, for example, aqueous or organic solvents such as physiologically buffered saline, glycols, glycerol, oils or injectable organic esters. A pharmaceutically acceptable carrier can also contain a physiologically acceptable compound that acts, for example, to stabilize or increase the solubility of a pharmaceutical composition. Such a physiologically acceptable compound can be, for example, a carbohydrate, such as glucose, sucrose or dextrans; an antioxidant, such as ascorbic acid or glutathione; a chelating agent; a low molecular weight protein; or another stabilizer or excipient. Pharmaceutically acceptable carriers, including solvents, stabilizers, solubilizers and preservatives, are described, for example, in Martin, *Remington's Pharm. Sci.*, 15th Ed. (Mack Publ. Co., Easton, 1975).

Those skilled in the art can formulate the therapeutic molecules to ensure proper distribution in vivo. For example, the blood-brain barrier (BBB) excludes many highly hydrophilic compounds. To ensure that the therapeutic molecules of the invention cross the BBB, if desired, they can be formulated, for example, in liposomes, or chemically derivatized. Methods of ensuring appropriate distribution in vivo can also be provided by rechargable or biodegradable devices, particularly where gradients of concentrations of drug in a tissue are desired. Various slow release polymeric devices are known in the art for the controlled delivery of drugs, and include both biodegradable and non-degradable polymers and hydrogels. Those skilled in the art understand that the choice of the pharmaceutical formulation and the appropriate preparation of the composition will depend on the intended use and mode of administration.

The PFM therapeutic molecules of the invention, including expression vectors, antisense oligonucleotides and ribozymes, PFM modulatory compounds, and antibodies, can be administered to a subject by any effective route. Suitable routes for delivering the therapeutic molecules of the invention include topically, intraocularly, intradermally, parenterally, orally, intranasally, intravenously, intramuscularly, intraspinally, intracerebrally and subcutaneously. In a preferred embodiment, the therapeutic PFM molecules are directly injected into a solid tumor, tumor-containing organ or tumor containing body cavity, in a effective amount to inhibit proliferation of the tumor cells. Alternatively, the therapeutic PFM molecules of the invention can be administered systemically into the blood or lymphatic circulation to reach cells in the circulatory system or in any organ or tissue.

An effective dose of a therapeutic molecule of the invention can be determined, for example, by extrapolation from the concentration required for binding an isolated PFM nucleic acid or polypeptide in the binding assays described herein; from the dose required to modulate PFM nucleic acid or polypeptide expression in the expression assays described herein; or from the dose required to modulate cell proliferation in the proliferation assays described herein.

An effective dose of a molecule of the invention for the treatment of proliferative disorders can also be determined from appropriate animal models, such as xenografts of human tumors in rats or mice. Human cancer cells can be introduced into an animal by a number of routes, including subcutaneously, intraveneously and intraperitoneally. Following establishment of a tumor, the animals can be treated with different doses of a molecule of the invention, and tumor mass or volume can be determined. An effective dose for treating cancer is a dose that results in either partial or complete regression of the tumor, reduction in metastasis, reduced discomfort, or prolonged lifespan.

The appropriate dose for treatment of a human subject with a therapeutic molecule of the invention can be determined by those skilled in the art, and is dependent on the nature and bioactivity of the particular compound, the desired route of administration, the gender, age and health of the individual, the number of doses and duration of treatment, and the particular condition being treated.

Diagnostic Applications

The PFM nucleic acids and polypeptides disclosed herein exist in different forms, depending on the splice variant expressed. PFM nucleic acids and polypeptides that express or contain an intact PR domain (PR+) are associated with regulated, or normal, cell proliferation. A decrease in the total amount, or relative amount, of the PR+ form of a PFM, or an increase in the total amount, or relative amount, of the PR− form of a PFM, is associated with unregulated, or pathological, cell proliferation. Therefore, determining the total or relative abundance of the. PR+ and PR− forms of PFM, or identifying alterations in the expression or structure of PFM nucleic acid molecules or polypeptides, can be used to distinguish between normal and pathologically proliferative cells in a sample.

The invention thus provides methods of detecting PFM nucleic acids and polypeptides in a sample. As used herein, the term "sample" is intended to mean any biological fluid, cell, tissue, organ or portion thereof, that includes or potentially includes PFM nucleic acids or polypeptides. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid or protein preparation. A sample can be prepared by methods known in the art suitable for the particular format of the detection method employed.

The detection methods of the invention can advantageously be used, for example, to identify pathologically proliferative cells, such as neoplastic cells, in a sample. As used herein, the term "neoplastic cell" is intended to mean a cell that exhibits histological or proliferative features of a malignant or premalignant cell. For example, by histological methods, a neoplastic cell can be observed to invade into surrounding normal tissue, have an increased mitotic index, an increased nuclear to cytoplasmic ratio, altered deposition of extracellular matrix, or a less differentiated phenotype. A neoplastic cell can also exhibit unregulated proliferation, such as anchorage independent cell growth, proliferation in reduced-serum medium, loss of contact inhibition, or rapid proliferation compared to normal cells. The diagnostic methods described herein are applicable to the identification of any type of neoplastic cell, such as neoplastic cells present in solid tumors (carcinomas and sarcomas) such as breast, colorectal, gynecological, lung, prostate, bladder, renal, liver, urethral, endocrinal, melanoma, basal cell, central nervous system, lymphoma, stomach, esophageal, squamous cell cancers, as well as all forms of leukemias, and metastases therefrom.

The diagnostic methods described herein can also be adapted for use as prognostic assays. Such an application takes advantage of the observation that alterations in expression or structure of different tumor suppressor molecules take place at characteristic stages in the progression of a proliferative disease or of a tumor. Knowledge of the stage of the tumor allows the clinician to select the most appropriate treatment for the tumor and to predict the likelihood of success of that treatment.

The diagnostic methods described herein can also be used to identify individuals at increased risk of developing a proliferative disease, such as cancer, due to hereditary mutations in a PFM.

The invention thus provides methods for detecting PFM nucleic acid in a sample. In one embodiment, the method consists of contacting the sample with an isolated PFM1, mPFM2, hPFM2, PFM3, PFM4 or PFM5 nucleic acid molecule, under conditions that allow specific hybridization to PFM nucleic acid, and detecting specific hybridization. The method of the invention is exemplified in Examples I, II and V, below, in which detection of PFM nucleic acid in tissue samples is described.

In another embodiment, the method consists of contacting the sample with a PFM primer pair, under conditions that allow amplification of PFM nucleic acid, and detecting amplified PFM nucleic acid. The method of the invention is exemplified in Examples I, II, III and V, below, in which detection of PFM nucleic acid in tissue samples is described.

The methods of detecting PFM nucleic acid in a sample can be either qualitative or quantitative, as desired. For example, the presence, abundance, integrity or structure of a PFM, or of particular splice variants thereof, can be determined, as desired, depending on the assay format and the probe or primer pair chosen.

Useful assays for detecting PFM nucleic acid based on specific hybridization with an isolated PFM nucleic acid molecule are well known in the art and include, for example, in situ hybridization, which can be used to detect altered chromosomal location of the nucleic acid molecule, altered gene copy number, and RNA abundance, depending on the assay format used. Other hybridization assays include, for example, Northern blots and RNase protection assays, which can be used to determine the abundance and integrity of different RNA splice variants, and Southern blots, which can be used to determine the copy number and integrity of DNA. A PFM hybridization probe can be labeled with any suitable detectable moiety, such as a radioisotope, fluorochrome, chemiluminescent marker, biotin, or other detectable moiety known in the art that is detectable by analytical methods.

Useful assays for detecting PFM nucleic acid in a sample based on amplifying PFM nucleic acid with a PFM primer pair are also well known in the art, and include, for example, qualitative or quantitative polymerase chain reaction (PCR); reverse-transcription PCR (RT-PCR); SSCP analysis, which can readily identify a single point mutation in DNA, such as in a PCR or RT-PCR product; and coupled PCR, transcription and translation assays, such as the Protein Truncation Test, in which a mutation in DNA is determined by an altered protein product on an electrophoresis gel. Additionally, the amplified PFM nucleic acid can be sequenced to detect mutations and mutational hot-spots, and specific assays for large-scale screening of samples to identify such mutations can be developed.

The invention also provides methods for detecting PFM polypeptide in a sample, by contacting the sample with an agent specific for PFM, under conditions that allow specific binding of the agent to PFM polypeptide, and detecting the specifically bound agent. As used herein the term "agent specific for PFM" refers to a molecule that specifically binds PFM. An-example of a molecule that specifically binds PFM is a PFM antibody, or antigen binding fragment thereof. Additionally, the PFM binding and modulatory compounds identified in the affinity screening methods described above are also suitable agents that can be used in methods of detecting PFM polypeptides.

Assays for detecting PFM polypeptides include, for example, immunohistochemistry, immunofluorescence, ELISA assays, radioimmunoassay, Facs analysis, immunoprecipitation, and immunoblot analysis, using antibodies or antigen binding fragments specific for PFM. Various immunoassays are well known in the art, and can be readily modified by those skilled in the art in cases in which the agent is a PFM binding molecule other than an antibody. If desired, the agent or antibody can be rendered detectable by incorporation of, or by conjugation to, a detectable moiety, or binding to a secondary molecule that is itself detectably labeled.

In the detection methods of the invention, the nucleic acid probes or primers, and polypeptide binding agents, can advantageously be directed against the PR domain of PFM, or the A, B or C boxes thereof. Therefore, these assays can be used to distinguish between PR+ growth-inhibiting, and PR−, growth-promoting, forms of PFM in a sample.

The following examples are intended to illustrate but not limit the present invention.

EXAMPLE I

Identification and Characterization of PFM1

This example shows identification of the gene encoding the PR-domain containing polypeptide designated PFM1, and characterization of its structure, expression pattern and chromosomal location.

cDNA libraries and EST databases were screened using the PR domain of RIZ1 as probe or query. This led to the identification of a mouse EST clone (mouse embryonic carcinoma cell line F9 cDNA clone B9H02, Accession Number D77868) encoding a PR domain. By sequence analysis of overlapping human cDNA clones obtained from the EST database and RACE, a contiguous full length cDNA sequence of 3.902 kb was identified (see FIG. 1A, SEQ ID NO:1), encoding an open reading frame of 796 amino acids from nt 139 to 2527 (see FIG. 1B, SEQ ID NO:2). The amino acid sequence is apparently full length because the ATG start codon at nucleotide 139 is preceded by an inframe stop codon. The predicted peptide sequence shows a PR domain in the middle portion of the protein followed by 6 zinc finger motifs at the carboxyl terminal half. The amino-terminal region did not show significant similarity to known genes and contains a Ser-rich region and a Pro-rich region. This gene was designated PFM1 for PR family member 1.

The structural features of PFM1 protein suggest a role for the protein as a DNA binding transcription factor. The PR domain of PFM1 is more related to BLIMP1 than to other PR genes. The location of the PR domain in the middle of the PFM1 protein is unusual in comparison with other PR family members, in which the PR domains of are located at the amino-terminus.

To determine the expression pattern of PFM1, Northern blot analysis was performed using either a 5' probe or a non-overlapping 3' probe of PFM1 cDNA (see FIG. 11A). Three different mRNA species were detected with the 5' probe, whereas four mRNA species were detected with the 3' probe (FIG. 11B, middle two panels). The major PFM1 mRNA species was ~4.6 kb in size. The 4.6 kb species was observed in all human tissues tested but was significantly more abundant in ovary and testis (FIG. 11B). The relatively high levels of the housekeeping gene beta-actin mRNA in ovary may reflect its actual abundance or may indicate that a slightly higher amount of ovary mRNA was loaded (FIG. 11B, bottom panel). Even taking into account possible mRNA overloading, the level of PFM1 transcript in ovary was still higher than in other tissues, as was independently confirmed by RT-PCR analysis based on normalization to a different housekeeping gene, G3PDH (FIG. 11C).

Northern blot analysis using the 5' probe also identified two alternative PFM1 mRNA species of ~7.0 kb and ~3.4 kb. The ~7.0 kb transcript was specifically found in ovary and testis; the ~3.4 kb transcript was found at low levels in peripheral blood leukocytes, colon, ovary, testis, prostate, and spleen (FIG. 11B, top two panels). All of these mRNA species were also detected with the 3' probe (FIG. 11B, third panel from top). In addition, an mRNA species of ~3.9 kb was specifically detected by the 3' probe, most evidently in peripheral blood leukocytes but also visible in ovary and testis. Because this mRNA was not detected with the 5' probe, which contains about 150 bp of the PR domain and all of the amino terminal regions (see FIG. 11A), this species likely represents a product of the PFM1 gene lacking the PR domain. Identification of a PR− PFM1 transcript reinforces previous observations that the expression of an alternative PR-lacking product appears to be a conserved feature of the PR domain gene family.

By RT-PCR analysis, eight other human tissue mRNAs were examined, in addition to those contained in the northern blot. Relatively high levels of PFM1 mRNA, similar to levels found in ovary and testis, were also observed in pancreas, prostate, placenta, heart, and brain (FIG. 11C). The lowest amount of PFM1 mRNA was found in skeletal muscle and liver. These data indicate that PFM1 gene is fairly ubiquitously expressed, but that the amount of expression varies in a tissue specific manner.

Obtaining the PFM1 cDNA sequence also allowed identification of an EST clone, gb|H33244 of PFM1 present in NGF treated PC-12 cells that was not present in non-treated PC-12 cells (Lee et al., *Proc. Natl. Acad. Sci. USA* 92:8303-8307 (1995)). This observation suggested that PFM1 expression may be higher in NGF-treated versus non-treated PC-12 cells. To test the effect of NGF on PFM1 expression, mRNA prepared from PC-12 cells that were in NGF-containing media for 9 days was used for RT-PCR analysis using primers derived from PFM cDNA sequences. The housekeeping gene beta-actin was amplified as a control for NGF non-responsive genes. As shown in FIG. 11D, NGF induced PFM1 gene expression between four- and eight-fold, indicating that PFM1 gene expression is induced upon neuronal cell differentiation. Therefore, PFM1 is likely to be involved in cell differentiation control and to play a role in the NGF signal transduction pathway.

Using PFM1 human cDNA as a query sequence, an STS (sequence tagged site) sequence, A005M11, of approximately 300 bp, which is identical to a portion of PFM1 sequence, was identified. This STS marker maps to between the markers D12S78 and D12S79 on human chromosome 12q (see Human Genome Resources at www.ncbi.nlm.nih.gov/genome/guide/). Several disease genes known to reside on 12q23-q24.1 have been mapped between D12S78 and D12S79, including SCA2 mutated in cerebellar ataxia (Gispert et al., *Nature Genet.* 4:295-299 (1993)), and ATP2A2 mutated in Darier disease (Sakuntabhai et al., *Nature Genet.* 21:271-277 (1999)). Based on the cytogenetic locations of these disease genes, it was concluded that PFM1 maps to 12q23-q24. 1 on the cytogenetic map.

The localization of PFM1 to human chromosome 12 was confirmed by analysis of somatic cell hybrids. PCR amplification of DNAs was performed, using a panel of human x rodent somatic cell hybrids, each retaining one intact human chromosome. A PCR fragment of PFM1 was only found in DNAs from the hybrid NA10868A, which contains chromosome 12.

Human chromosome band 12q23-q24.1 is thought to harbor tumor suppressor genes. Gene deletion or loss of heterozygosity in this region is found in several types of human cancers, including ovarian cancer (Hatta et al., *Br. J. Cancer* 75:1256-1262 (1997); Sato et al., *Cancer Res.* 51:5118-5122 (1991)), pancreatic cancer (Kimura et al., *Cancer Res.* 58:2456-2460 (1998)), and gastric cancer (Schmutte et al., *Cancer Res.* 57:3010-3015 (1997)). In addition, a gene involved in spinal muscular atrophies is thought to reside on 12q23-q24.1, which remains to be cloned (van der Vleuten et al., *Eur. J. Hum. Genet.* 6:376-382 (1998)).

Thus, because of the known involvement of PR-domain family members in cell differentiation and cancer, the chromosomal location of PFM1 suggests a role for PFM1 in human diseases including cancer and muscular atrophies.

Furthermore, the specific high level expression of PFM1 in normal ovary and pancreas suggests that PFM1 is a particularly strong candidate for the ovarian and pancreatic cancer suppressor gene located on 12q23-q24.1.

EXAMPLE II

Identification and Characterization of PFM2

This example shows identification of the gene encoding the PR-domain containing polypeptides designated PFM2 (human) and mPFM2 (mouse), and characterization of their structure, expression pattern and chromosomal location.

An EST sequence (1467290, Accession number AA884744) was identified that shows partial homology to the RIZ1 PR domain. Sequence analysis of this EST and other overlapping EST clones allowed the assembly of a contiguous cDNA sequence of 1.065 kb, designated PFM2 (FIG. 2A; SEQ ID NO:3). PFM2 cDNA encodes an open reading frame of 298 amino acids (FIG. 2B; SEQ ID NO:4). The predicted open reading frame of PFM2 contains the B and C boxes of the PR domain and six zinc finger domains (see FIG. 12A). The A box found in other PR-domain containing proteins was absent from the reading frame because of deletion of one nucleotide next to the B box region. This lack of one nucleotide has been confirmed by sequencing normal human genomic DNA.

Scanning of the peptide sequence also identified a LXCXE motif which is a sequence motif known to bind retinoblastoma protein. A similar motif is present in the RIZ gene products.

To analyze PFM2 gene expression, an MTN blot (Clontech) was probed with a 0.5 kb XbaI-NotI fragment from the plasmid 1467290, which corresponds to the N-terminal region of PFM2 immediately upstream of the zinc finger domain. Northern blot analysis identified abundant expression of PFM2 in the ovary (FIG. 12B). A major mRNA species of 6.0 kb and two alternative, less abundant transcripts of 8.0 and 4.0 kb were observed when using the PR domain region of PFM2 as a probe.

To further analyze PFM2 expression, MTC cDNAs (Clontech) were analyzed by PCR using primer PFM2.15 having the sequence 5'-GGTGAAAAGTTCGGACCCTTT-3' (SEQ ID NO:81) and primer PFM2.18 having the sequence 5'-TGCCCGCTGTTGATTGTCTTC-3' (SEQ ID NO:82). RT-PCR analysis of various human tissue RNAs confirmed that PFM2 expression is more abundant in ovary (FIG. 12C).

To map the chromosomal location of PFM2, the Standford TNG radiation hybrid panel was screened with a pair of PCR primers that amplify PFM2 gene. This mapped PFM2 to within 420 kb from the marker SHGC4-1184 on 4q25-4q26. The 4q25-4q26 region is commonly deleted in human ovarian cancer, (Sonoda et al., *Genes, Chroms. and Cancer* 20:320-328 (1997)) lung cancer (Shivapurkar et al., *Clin. Cancer Res.* 5:17-23 (1999), hepatoma (Chou et al., *Cancer Letters* 123:1-6 (1998); Piao et al., *Int. J. Cancer* 79:356-60 (1998)), cervical cancer (Mitra et al., *Cancer Res.* 54:4481-4487 (1994)), breast cancer (Schwendel et al., *Brit. J. Cancer* 78:806-811 (1998); Tirkkonen et al., *Cancer Res.* 57:1222-1227 (1997)), head and neck squamous cell carcinoma (Pershouse et al., *Oncogene* 14:369-373 (1997)), colon cancer (Arribas et al., *Laboratory Invest.* 79:111-122 (1999)), and oral cancer (Wang et al., *Oncogene* 18, 823-825 (1999)). The chromosomal location of PFM2 is thus consistent with it being a tumor suppressor gene. Given the tissue specific expression of PFM2 in ovary, PFM2 is a strong candidate for the ovarian cancer suppressor locus on 4q25-4q26.

PFM2 is also a candidate for the iris hypoplasia locus on 4q25 (Heon et al., *Human Mol. Genet.* 4:1435-1439 (1995)). Iris hypoplasia is an autosomal dominant disorder which is frequently associated with glaucoma.

Analysis of EST databases identified two alternative forms of PFM2 in the mouse. mPFM2a contains 2262 nt of cDNA (FIG. 3A, SEQ ID NO:5) with an open reading frame of 648 aa (FIG. 3B, SEQ ID NO:6). As shown schematically in FIG. 12A, mPFMa has 16 zinc finger domains and an intact PR domain. mPFM2b has 1127 nt of cDNA (FIG. 4A, SEQ ID NO:7) with an open reading frame of 110 aa (FIG. 4B, SEQ ID NO:8). PFM2b has no zinc finger domains and lacks the C box of the PR domain (FIG. 12A). PFM2b is likely an alternatively spliced form of PFM2 gene.

EXAMPLE III

Identification and Characterization of PFM3

This example shows identification of the gene encoding the PR-domain containing polypeptide designated PFM3, and characterization of its structure, expression pattern and chromosomal location.

Sequence analysis of EST clones related to the PR domain of RIZ1 (EST clone 1853988, Accession Number AI243539) identified a PR gene designated PFM3a. The PFM3a cDNA is 2.187 kb (FIG. 5A; SEQ ID NO:9) and encodes an open reading frame of 402 aa (FIG. 5B; SEQ ID NO:10). As shown schematically in FIG. 13A, PFM3a contains a PR domain and four zinc finger domains. An alternatively spliced form of PFM3 is also expressed, designated PFM3b (FIG. 6A; SEQ ID NO:11), that encodes an open reading frame of 318 amino acids (FIG. 6B; SEQ ID NO:12). PFM3b lacks the B and C boxes of the PR domain, as shown in FIG. 13A. These alternative structures are reminiscent of the alternative PR-plus and PR-minus products of RIZ1 and MDS1-EVI1 genes.

RT-PCR analysis was performed on human tissue RNA to examine PFM3 expression. The primers used were PFM3.1 (5'-GCTGCCTGAAAGTCTTAAAGCA-3'; SEQ ID NO:83) and PFM3.2 (5'-CAGCAAGGCACCTGGATTG-GACC-3'; SEQ ID NO:84). As shown in FIG. 13B, PFM3a was detected in ovary, prostate, pancreas and kidney. Relatively weaker expression was also found in other tissues.

To map the chromosomal location of PFM3, the Standford TNG radiation hybrid panel was screened by a pair of PCR primers that amplifies PFM3 gene. This analysis mapped PFM3 to within 1000 kb from the marker SHGC-69102 on 5q21. The 5q21 region also contains the APC gene, which is deleted in colon cancer. In addition, the 5q21 region is deleted in lung cancer (Cooper et al., *J. Pathology* 180: 33-37 (1996); Endo et al., *Brit. J. Cancer* 78:612-615(1998); Wieland et al., *Oncogene* 12:97-102 (1996)), gastric cancer (Sanz-Ortega et al., *Pathology, Research & Practice* 192: 1206-1210 (1996); Tamura et al., *Cancer Res.* 56:612-615 (1996)), MDS and AML (Pedersen, *Leukemia* 10: 1883-1890 (1996)), and ovarian cancer (Saretzki et al., *Cancer* 80:1241-1249 (1997); Tavassoli et al., *Brit. J. Cancer* 74, 115-119 (1996)). The chromosomal location of PFM3 is consistent with PFM3 being a tumor suppressor gene. The relatively high level expression of PFM3 in ovary suggests that PFM3 is a strong candidate for the ovarian tumor suppressor on 5q21.

EXAMPLE IV

Characterization of PFM4

This example shows identification of the gene encoding the PR-domain containing polypeptide designated PFM4, and characterization of its structure and chromosomal location.

Sequence analysis of human genomic DNA databases identified a PR family member, designated PFM4, present in clone 439G8 located on 16q (GenBank Accession number AC007046). The full length cDNA sequence was assembled from predicted exons.

No EST clones of PFM4 were observed by querying publically available databases, indicating that PFM4 mRNA levels are extremely low in most tissues.

The predicted PFM4 cDNA contains four exons. The PFM4 cDNA (FIG. 7A, SEQ ID NO:13) encodes an open reading frame of 407 amino acids (FIG. 7B, SEQ ID NO:14). PFM4 protein has one PR domain at the amino-terminus, one zinc finger domain in the middle followed by a domain of approximately 100 residues, and three zinc finger domains at the C-terminus, as depicted schematically in FIG. 14.

The 100 residue domain exhibits 34% identity to the N-terminal region of the KRAB-domain containing zinc finger protein 133, ZNF133, and is thus designated PKZL, for "PR and KRAB zinc-finger protein linked." Analysis of human genomic sequences revealed two additional zinc finger-containing genes, designated PKZL1 (FIG. 9) and PKZL2 (FIG. 10), that contain PKZL domains. The PKZL domains of these genes share 35-40% amino acid identity. ZNF133, PKZL1 and PKZL2 all map to chromosome 20. The PKZL2 genomic clone contains STS marker D20S826 which maps to 20p13.

Clone 439G8 sequence also contains the growth-arrest specific GAS11 gene which maps to 16q24 (Whitmore et al., *Genomics* 52:325-331 (1998)). This region is commonly deleted in prostate cancer (Cher et al., *J. Urology* 153:249-254 (1995); Pan et al., *Prostate* 36:31-38 (1998)), breast cancer (Driouch et al., *Genes, Chromosomes & Cancer* 19:185-191 (1997); Harada et al., *Cancer* 74, 2281-2286 (1994); Tsuda et al., *Cancer Res.* 54, 513-517 (1990)), and hepatoma (Tsuda et al., *Proc. Natl. Acad. Sci. U.S.A.* 87:6791-6794 (1994)).

A polymorphic allele of PFM4 was identified and used to detect loss of heterozygosity (LOH) of PFM4 gene in breast cancer. These results showed 50% loss of heterozygosity at the PFM4 locus, consistent with a role for PFM4 as a tumor suppressor gene in breast tissue.

EXAMPLE V

Characterization of PFM5

This example shows identification of the gene encoding the PR-domain containing polypeptide designated PFM5, and characterization of its structure, expression pattern and chromosomal location.

An EST clone (2164030, Accession number AI570404) was identified encoding a PR-containing gene designated PFM5. A total of 2.5 kb of cDNA sequence (FIG. 8A, SEQ ID NO:15) has been obtained which encodes an open reading frame of 299 amino acids (FIG. 8B, SEQ ID NO:16). The PR domain of PFM5 is most similar to the T21B10.5 open reading frame from the *C. elegans* genome. In contrast to T21B10.5, which lacks zinc finger domains, PFM5 has a single zinc finger domain. Therefore, PFM5 is likely the human homolog of the *C. elegans* T21B10.5 gene.

Using PFM5 cDNA as a query sequence, 34 human EST sequences were identified in the database. Of these sequences, 68% (23/34) are from the human retina, suggesting retina specific expression of PFM5.

Figure 15A:
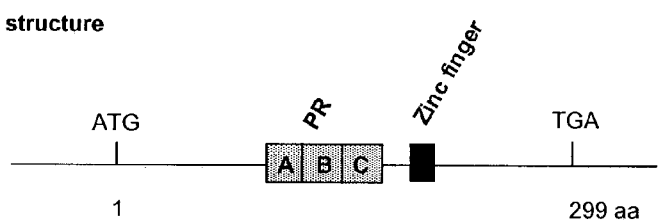
FIG. 15A shows a schematic representation of the structure of PFM5.
Figure 15B:
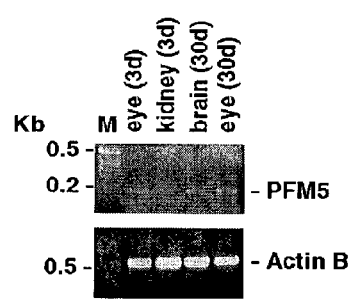
FIG. 15B shows expression of PFM5 in various mouse tissues by Northern blot analysis.

To examine PFM5 expression, mouse tissue RNAs were analyzed by RT-PCR using primers PFM5.7 (5'-AACGGA-CAGCTGTTCTACCGC-3'; SEQ ID NO:85) and PFM5.11 (5'-AAGTCTCTTGGGGCAGCGGAA-3'; SEQ ID NO:86). RT-PCR analysis of mouse tissues suggests that PFM5 is expressed in mouse retina and brain but not in kidney (FIG. 15B).

Figure 15C:
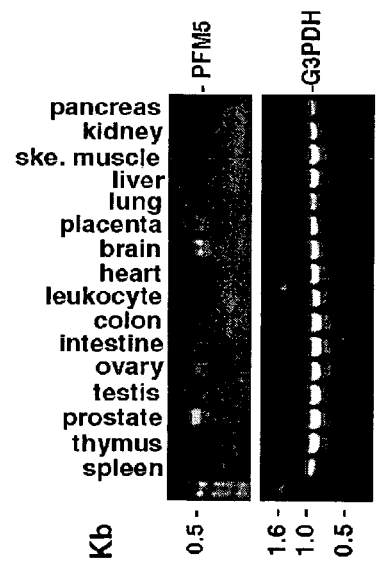
FIG. 15C show expression of PFM5 in various human tissues by RT-PCR analysis.

Human multiple tissue cDNAs tissues were amplified by PCT using primer PFM5.6 (5'-CTCCGGGAATTTC-CTCTTTG-3') (SEQ ID NO:87) and primer PFM5.7. In human tissues, PFM5 was most abundant in prostate and brain relative to other tissues, although retina was not examined (FIG. 15C).

Screening of TNG-radiation hybrid panel mapped the PFM5 gene to human chromosome 4q21.1. This region contains a susceptibility locus for Parkinson's disease (Polymeropoulos et al., *Science* 274, 1197-1199 (1996)), as well as tumor suppressor genes for lung cancer and mesothelioma (Shivapurkar et al., *Clin. Cancer Res.* 5: 17-23 (1999)), colon cancer (Arribas et al., *Lab. Invest.* 79:111-122 (1999), and hepatoma (Huang et al., *Cancer Genet. & Cytogenet.* 111:21-27 (1999)). PFM5 EST clones have also been found in colon cancer and B cell leukemia.

Therefore, based on its structure, expression pattern and chromosomal location, the PR-domain gene PFM5 is likely to be a tumor suppressor gene.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the claims.

What is claimed is:

1. An isolated PR family member 1 (PFM1) polypeptide, comprising amino acid sequence SEQ ID NO:2.

2. The isolated PFM1 polypeptide of claim 1, consisting of amino acid sequence SEQ ID NO:2.

3. An isolated PR family member 1 (PFM1) polypeptide consisting of a PFM1 PR domain amino acid sequence SEQ ID NO: 18; or a PFM1 ZF domain amino acid sequence SEQ ID NO:64.

4. The isolated PFM1 polypeptide of claim 3, consisting of amino acid sequence SEQ ID NO:18.

5. The isolated PFM1 polypeptide of claim 3, consisting of amino acid sequence SEQ ID NO:64.

6. An isolated PR family member 1 (PFM1) peptide, consisting of amino acid sequence SEQ ID NO:30, SEQ ID NO:32 or SEQ ID NO:34.

7. The isolated PFM1 peptie of claim 6, consisting of amino acid sequence SEQ ID NO:30.

8. The isolated PFM 1 peptide of claim 6, consisting of amino acid sequence SEQ ID NO:32.

9. The isolated PFM1 peptide of claim 6, consisting of amino acid sequence SEQ ID NO:34.

\* \* \* \* \*

SEQUENCE LISTING

<160> NUMBER OF SEQ ID NOS: 93

<210> SEQ ID NO 1
<211> LENGTH: 3902
<212> TYPE: DNA

-continued

```
<213> ORGANISM: Homo sapiens
<220> FEATURE:
<221> NAME/KEY: CDS
<222> LOCATION: (139)..(2529)

<400> SEQUENCE: 1
attacaggtg taaatcacca cacctgggct gctttatttt atagcacgtg accctggaac      60
gcaaaccctg atgcctgtcc ccaccacccg agcgctcctt ctctgatatt ggccccaagc     120
cgatgcatca caggatga atg aaa atg aac ctg agt cca gtg ggg atg gcg      171
                    Met Lys Met Asn Leu Ser Pro Val Gly Met Ala
                     1               5                  10 cag ctg act tca tcc tct gtg agc aat gcc ttg cca gtc tca gga agt      219
Gln Leu Thr Ser Ser Ser Val Ser Asn Ala Leu Pro Val Ser Gly Ser
            15                  20                  25 cac ctg gga ttg gct gcc tca ccc act cac agt gcc atc cct gcc cca      267
His Leu Gly Leu Ala Ala Ser Pro Thr His Ser Ala Ile Pro Ala Pro
        30                  35                  40 ggc ctc cca gtg gca att cca aac ctg ggt ccc tcc ctg agc tct ctg      315
Gly Leu Pro Val Ala Ile Pro Asn Leu Gly Pro Ser Leu Ser Ser Leu
    45                  50                  55 cct tct gct ctg tct tta atg cta cca atg ggt att ggg gat cga ggg      363
Pro Ser Ala Leu Ser Leu Met Leu Pro Met Gly Ile Gly Asp Arg Gly
60                  65                  70                  75 gtg atg tgt ggg tta cct gaa aga aac tac acc cta cct cca cca cct      411
Val Met Cys Gly Leu Pro Glu Arg Asn Tyr Thr Leu Pro Pro Pro Pro
                80                  85                  90 tac cct cac ctg gag agc agt tat ttc aga acc att cta cct ggc att      459
Tyr Pro His Leu Glu Ser Ser Tyr Phe Arg Thr Ile Leu Pro Gly Ile
            95                 100                 105 tta tct tat tta gct gac aga cca cct cca cag tac atc cac cct aac      507
Leu Ser Tyr Leu Ala Asp Arg Pro Pro Pro Gln Tyr Ile His Pro Asn
        110                 115                 120 tct ata aat gtt gat ggt aat aca gca tta tct atc acc aat aac cct      555
Ser Ile Asn Val Asp Gly Asn Thr Ala Leu Ser Ile Thr Asn Asn Pro
    125                 130                 135 tca gca cta gat ccc tat cag tcc aat gga aat gtt gga tta gaa cca      603
Ser Ala Leu Asp Pro Tyr Gln Ser Asn Gly Asn Val Gly Leu Glu Pro
140                 145                 150                 155 ggc att gtt tca ata gac tct cgc tct gtg aac aca cat ggt gcc caa      651
Gly Ile Val Ser Ile Asp Ser Arg Ser Val Asn Thr His Gly Ala Gln
                160                 165                 170 agt ctt cat ccc agt gat ggc cat gag gtg gcc ttg gac aca gca atc      699
Ser Leu His Pro Ser Asp Gly His Glu Val Ala Leu Asp Thr Ala Ile
            175                 180                 185 act atg gag aac gtt tct agg gtt acc agc cca att tcg aca gat gga      747
Thr Met Glu Asn Val Ser Arg Val Thr Ser Pro Ile Ser Thr Asp Gly
        190                 195                 200 atg gca gag gag ctt acg atg gac ggt gtt gca ggc gag cat tcc caa      795
Met Ala Glu Glu Leu Thr Met Asp Gly Val Ala Gly Glu His Ser Gln
    205                 210                 215 atc cca aat ggc tcc aga agt cat gaa cct ctg tct gtg gat tct gtg      843
Ile Pro Asn Gly Ser Arg Ser His Glu Pro Leu Ser Val Asp Ser Val
220                 225                 230                 235 agc aac aac ctt gca gca gac gct gta gga cat ggt ggt gta ata ccc      891
Ser Asn Asn Leu Ala Ala Asp Ala Val Gly His Gly Gly Val Ile Pro
                240                 245                 250 atg cat ggg aat ggc ctg gag ctc cct gtg gtc atg gag aca gac cac      939
Met His Gly Asn Gly Leu Glu Leu Pro Val Val Met Glu Thr Asp His
            255                 260                 265
```

```
att gca agt cgg gtc aat ggc atg tct gac agt gcc ctc agt gac tcc    987
Ile Ala Ser Arg Val Asn Gly Met Ser Asp Ser Ala Leu Ser Asp Ser
        270                 275                 280 att cac act gtg gcc atg agc acc aac tct gta agc gtg gca ctc tct   1035
Ile His Thr Val Ala Met Ser Thr Asn Ser Val Ser Val Ala Leu Ser
285                 290                 295 acc tca cac aac ctt gcc tcc cta gaa tct gtt tcc ctc cat gaa gtt   1083
Thr Ser His Asn Leu Ala Ser Leu Glu Ser Val Ser Leu His Glu Val
300                 305                 310                 315 ggc ctc agc cta gaa cct gtg gct gtc tcc tcc atc acc cag gag gtt   1131
Gly Leu Ser Leu Glu Pro Val Ala Val Ser Ser Ile Thr Gln Glu Val
                320                 325                 330 gct atg ggg aca ggt cat gta gat gta tct tca gac agt ctt tct ttt   1179
Ala Met Gly Thr Gly His Val Asp Val Ser Ser Asp Ser Leu Ser Phe
            335                 340                 345 gta tca cct tca ctg caa atg gaa gac tcc aat tca aac aag gag aac   1227
Val Ser Pro Ser Leu Gln Met Glu Asp Ser Asn Ser Asn Lys Glu Asn
        350                 355                 360 atg gca acc ttg ttt aca att tgg tgt act ctg tgt gac cgc gcc tat   1275
Met Ala Thr Leu Phe Thr Ile Trp Cys Thr Leu Cys Asp Arg Ala Tyr
365                 370                 375 ccc tcg gac tgt ccc gaa cat gga cca gtg act ttt gtt cct gac act   1323
Pro Ser Asp Cys Pro Glu His Gly Pro Val Thr Phe Val Pro Asp Thr
380                 385                 390                 395 cca ata gag agc aga gca agg ctt tct ctc cca aag cag ctt gtt ctc   1371
Pro Ile Glu Ser Arg Ala Arg Leu Ser Leu Pro Lys Gln Leu Val Leu
                400                 405                 410 cgt cag tca att gtg gga gca gaa gtt ggt gta tgg act gga gaa acc   1419
Arg Gln Ser Ile Val Gly Ala Glu Val Gly Val Trp Thr Gly Glu Thr
            415                 420                 425 att cct gtg cgg act tgc ttt gga cct cta att ggc cag cag agt cac   1467
Ile Pro Val Arg Thr Cys Phe Gly Pro Leu Ile Gly Gln Gln Ser His
        430                 435                 440 tcc atg gaa gta gca gaa tgg aca gac aag gca gtt aac cat atc tgg   1515
Ser Met Glu Val Ala Glu Trp Thr Asp Lys Ala Val Asn His Ile Trp
445                 450                 455 aag ata tac cac aat ggt gtc cta gaa ttc tgc atc att aca act gat   1563
Lys Ile Tyr His Asn Gly Val Leu Glu Phe Cys Ile Ile Thr Thr Asp
460                 465                 470                 475 gaa aat gaa tgt aat tgg atg atg ttt gtg cgc aaa gcc agg aac cgg   1611
Glu Asn Glu Cys Asn Trp Met Met Phe Val Arg Lys Ala Arg Asn Arg
                480                 485                 490 gaa gag cag aat ttg gtg gct tat cct cat gat gga aaa atc ttt ttc   1659
Glu Glu Gln Asn Leu Val Ala Tyr Pro His Asp Gly Lys Ile Phe Phe
            495                 500                 505 tgc acc tca caa gat atc cct cct gaa aat gaa ctg ctt ttt tat tat   1707
Cys Thr Ser Gln Asp Ile Pro Pro Glu Asn Glu Leu Leu Phe Tyr Tyr
        510                 515                 520 agc cga gat tat gct caa cag att ggt gtt cct gaa cac cca gat gtg   1755
Ser Arg Asp Tyr Ala Gln Gln Ile Gly Val Pro Glu His Pro Asp Val
525                 530                 535 cat ctc tgt aac tgt ggc aag gag tgc aat tct tac aca gag ttc aaa   1803
His Leu Cys Asn Cys Gly Lys Glu Cys Asn Ser Tyr Thr Glu Phe Lys
540                 545                 550                 555 gcc cat ctg acc agc cac atc cat aac cat ctt cct acc cag gga cat   1851
Ala His Leu Thr Ser His Ile His Asn His Leu Pro Thr Gln Gly His
                560                 565                 570 agc ggc agc atc ggg cca agt cac agc aaa gaa agg aag tgg aag tgc   1899
Ser Gly Ser Ile Gly Pro Ser His Ser Lys Glu Arg Lys Trp Lys Cys
            575                 580                 585
```

```
tca atg tgc ccc caa gct ttt atc tct cct tcc aaa ctt cat gtc tac    1947
Ser Met Cys Pro Gln Ala Phe Ile Ser Pro Ser Lys Leu His Val Tyr
    590                 595                 600 ttt atg ggt cac atg ggt atg aag ccc cac aag tgt gat ttc tgt agc    1995
Phe Met Gly His Met Gly Met Lys Pro His Lys Cys Asp Phe Cys Ser
605                 610                 615 aag gct ttt agt gat ccc agc aac ctg cgg acc cac ctc aag ata cat    2043
Lys Ala Phe Ser Asp Pro Ser Asn Leu Arg Thr His Leu Lys Ile His
620                 625                 630                 635 aca ggt cag aag aac tac agg tgt acc ttg tgt gac aag tct ttc acc    2091
Thr Gly Gln Lys Asn Tyr Arg Cys Thr Leu Cys Asp Lys Ser Phe Thr
        640                 645                 650 cag aag gct cac ctg gga gtc cac atg gtt atc cac act ggg gag aag    2139
Gln Lys Ala His Leu Gly Val His Met Val Ile His Thr Gly Glu Lys
    655                 660                 665 aat ctt aag tgt gat tac tgt gac aag ttg ttt atg cgg agg cag gac    2187
Asn Leu Lys Cys Asp Tyr Cys Asp Lys Leu Phe Met Arg Arg Gln Asp
670                 675                 680 ctc aag cag cac gtg ctc atc cac act caa gaa cgc cag atc aag tgt    2235
Leu Lys Gln His Val Leu Ile His Thr Gln Glu Arg Gln Ile Lys Cys
685                 690                 695 ccc aag tgt gat aag ctg ttc ttg aga aca aat cac tta aag aag cat    2283
Pro Lys Cys Asp Lys Leu Phe Leu Arg Thr Asn His Leu Lys Lys His
700                 705                 710                 715 ctc aat tct cat gaa gga aaa cgg gat tat gtc tgt gaa aaa tgt aca    2331
Leu Asn Ser His Glu Gly Lys Arg Asp Tyr Val Cys Glu Lys Cys Thr
        720                 725                 730 aag gct tat cta acc aaa tac cat ctc acc cgc cac ctg aaa acc tgc    2379
Lys Ala Tyr Leu Thr Lys Tyr His Leu Thr Arg His Leu Lys Thr Cys
    735                 740                 745 aaa ggg ccc acc tcc agt tcg tca gca cca gag gag gaa gaa gag gat    2427
Lys Gly Pro Thr Ser Ser Ser Ala Pro Glu Glu Glu Glu Glu Asp
750                 755                 760 gac tca gaa gag gaa gat cta gca gac tct gtg ggg aca gaa gac tgt    2475
Asp Ser Glu Glu Glu Asp Leu Ala Asp Ser Val Gly Thr Glu Asp Cys
765                 770                 775 agg att aac agt gct gtg tat tca gcg gat gag tct ctt tct gca cat    2523
Arg Ile Asn Ser Ala Val Tyr Ser Ala Asp Glu Ser Leu Ser Ala His
780                 785                 790                 795 aaa taa aaggaaagga accggcattt ctggatgaaa atgcaaatgg aaaaatacac      2579
Lys atacccagtt atctactata atggttttta tataaaatgg ttctgattta ttttcagcca   2639
gtaatcaaaa cagactggga atgaataaag cacttacaga agagtctcta atgaaaacac   2699
tttaaaacag attgggaaaa ctgagcatgt gtcctatttt aagtggtgga ctgggaggga   2759
agtgtaactt ctgaggcttt attacatgat aatctgggag atgcatttat ctgaatcaaa   2819
gctgccttct gctcaaacaa atcagattta tttcacattc ttccattatt ccattttcct   2879
gctggtcctg tgacttggta acattctaaa cggtccttgc cccatagcca tcctgattgc   2939
tgatagtgtt ttatgcagac tcttgtgact tatactcacc acagaatgga ttgggacaca   2999
gcagcataag tgtgctactt ggcagctagt aagtttaaag caggacctgc cttaactgct   3059
cctggccact tggaagttta gggtagatct tgttttccaa agtttcggca ggtgctggag   3119
ggcaaataaa aaagcagcag tcagtcagta gtcagtgatg agagaacaa gaggagagat    3179 gcctggcctc tgcccaagaa attagctttg atggaagcct gagcaagtca cctggttatt   3239
gtaacgtgga gatctttgta ggtttagaca tggctccctg tctccagtaa acatccagcc   3299
```

-continued

```
attcagacaa agggggcctg gagatacaga gagcccaaat aatgcctgct ggattgtctc    3359
ctgatgagta catgtggact cacctgagga agggaaggaa gggaataatc ttttatgttt    3419
catttacctt atgaaaagtg ttaaaacatt gccaactcaa aataacatta tttaatgcat    3479
gtgcaaagtt aggtcttccc agttgtctca gtgctgagga acctcatcag agaagcatgg    3539
aagatgccaa aggattttg gaaggtaaag aaggctgaat agtgaccaca tgggcctgtt    3599
ttcagggtcc cagcttagtt aagtcaccca tgcacctggt cattgtgtct cccgtgcaca    3659
tccagcgttt ctcagaagca gacccaccct taagttgaca ggattgatgg aacatgctct    3719
cctgctcaag gcacaacctc tgggctggag tagaggactc tggtgggaag gttttgctgc    3779
taatgtattt atggaatgaa tgtatttcat tcaaatctgt attcctctag gaaggattaa    3839
aattaaactt ttttaaaata ccggaaaaaa aaaaaaaaaa aaaaaaaaaa aaaaaaaaa     3899 aaa                                                                 3902
```

<210> SEQ ID NO 2
<211> LENGTH: 796
<212> TYPE: PRT
<213> ORGANISM: Homo sapiens

<400> SEQUENCE: 2

```
Met Lys Met Asn Leu Ser Pro Val Gly Met Ala Gln Leu Thr Ser Ser
 1               5                  10                  15

Ser Val Ser Asn Ala Leu Pro Val Ser Gly Ser His Leu Gly Leu Ala
            20                  25                  30

Ala Ser Pro Thr His Ser Ala Ile Pro Ala Pro Gly Leu Pro Val Ala
        35                  40                  45

Ile Pro Asn Leu Gly Pro Ser Leu Ser Ser Leu Pro Ser Ala Leu Ser
    50                  55                  60

Leu Met Leu Pro Met Gly Ile Gly Asp Arg Gly Val Met Cys Gly Leu
65                  70                  75                  80

Pro Glu Arg Asn Tyr Thr Leu Pro Pro Pro Tyr Pro His Leu Glu
                85                  90                  95

Ser Ser Tyr Phe Arg Thr Ile Leu Pro Gly Ile Leu Ser Tyr Leu Ala
            100                 105                 110

Asp Arg Pro Pro Gln Tyr Ile His Pro Asn Ser Ile Asn Val Asp
        115                 120                 125

Gly Asn Thr Ala Leu Ser Ile Thr Asn Asn Pro Ser Ala Leu Asp Pro
    130                 135                 140

Tyr Gln Ser Asn Gly Asn Val Gly Leu Glu Pro Gly Ile Val Ser Ile
145                 150                 155                 160

Asp Ser Arg Ser Val Asn Thr His Gly Ala Gln Ser Leu His Pro Ser
                165                 170                 175

Asp Gly His Glu Val Ala Leu Asp Thr Ala Ile Thr Met Glu Asn Val
            180                 185                 190

Ser Arg Val Thr Ser Pro Ile Ser Thr Asp Gly Met Ala Glu Glu Leu
        195                 200                 205

Thr Met Asp Gly Val Ala Gly Glu His Ser Gln Ile Pro Asn Gly Ser
    210                 215                 220

Arg Ser His Glu Pro Leu Ser Val Asp Ser Val Ser Asn Asn Leu Ala
225                 230                 235                 240

Ala Asp Ala Val Gly His Gly Gly Val Ile Pro Met His Gly Asn Gly
                245                 250                 255
```

-continued

```
Leu Glu Leu Pro Val Met Glu Thr Asp His Ile Ala Ser Arg Val
            260             265             270

Asn Gly Met Ser Asp Ser Ala Leu Ser Asp Ser Ile His Thr Val Ala
            275             280             285

Met Ser Thr Asn Ser Val Ser Val Ala Leu Ser Thr Ser His Asn Leu
            290             295             300

Ala Ser Leu Glu Ser Val Ser Leu His Glu Val Gly Leu Ser Leu Glu
305             310             315             320

Pro Val Ala Val Ser Ser Ile Thr Gln Glu Val Ala Met Gly Thr Gly
                325             330             335

His Val Asp Val Ser Ser Asp Ser Leu Ser Phe Val Ser Pro Ser Leu
            340             345             350

Gln Met Glu Asp Ser Asn Ser Asn Lys Glu Asn Met Ala Thr Leu Phe
            355             360             365

Thr Ile Trp Cys Thr Leu Cys Asp Arg Ala Tyr Pro Ser Asp Cys Pro
            370             375             380

Glu His Gly Pro Val Thr Phe Val Pro Asp Thr Pro Ile Glu Ser Arg
385             390             395             400

Ala Arg Leu Ser Leu Pro Lys Gln Leu Val Leu Arg Gln Ser Ile Val
                405             410             415

Gly Ala Glu Val Gly Val Trp Thr Gly Glu Thr Ile Pro Val Arg Thr
            420             425             430

Cys Phe Gly Pro Leu Ile Gly Gln Gln Ser His Ser Met Glu Val Ala
            435             440             445

Glu Trp Thr Asp Lys Ala Val Asn His Ile Trp Lys Ile Tyr His Asn
            450             455             460

Gly Val Leu Glu Phe Cys Ile Ile Thr Thr Asp Glu Asn Glu Cys Asn
465             470             475             480

Trp Met Met Phe Val Arg Lys Ala Arg Asn Arg Glu Glu Gln Asn Leu
                485             490             495

Val Ala Tyr Pro His Asp Gly Lys Ile Phe Phe Cys Thr Ser Gln Asp
            500             505             510

Ile Pro Pro Glu Asn Glu Leu Leu Phe Tyr Tyr Ser Arg Asp Tyr Ala
            515             520             525

Gln Gln Ile Gly Val Pro Glu His Pro Asp Val His Leu Cys Asn Cys
            530             535             540

Gly Lys Glu Cys Asn Ser Tyr Thr Glu Phe Lys Ala His Leu Thr Ser
545             550             555             560

His Ile His Asn His Leu Pro Thr Gln Gly His Ser Gly Ser Ile Gly
                565             570             575

Pro Ser His Ser Lys Glu Arg Lys Trp Lys Cys Ser Met Cys Pro Gln
            580             585             590

Ala Phe Ile Ser Pro Ser Lys Leu His Val Tyr Phe Met Gly His Met
            595             600             605

Gly Met Lys Pro His Lys Cys Asp Phe Cys Ser Lys Ala Phe Ser Asp
            610             615             620

Pro Ser Asn Leu Arg Thr His Leu Lys Ile His Thr Gly Gln Lys Asn
625             630             635             640

Tyr Arg Cys Thr Leu Cys Asp Lys Ser Phe Thr Gln Lys Ala His Leu
                645             650             655

Gly Val His Met Val Ile His Thr Gly Glu Lys Asn Leu Lys Cys Asp
            660             665             670

Tyr Cys Asp Lys Leu Phe Met Arg Arg Gln Asp Leu Lys Gln His Val
```

-continued

```
                                675                 680                 685
Leu Ile His Thr Gln Glu Arg Gln Ile Lys Cys Pro Lys Cys Asp Lys
    690                 695                 700

Leu Phe Leu Arg Thr Asn His Leu Lys Lys His Leu Asn Ser His Glu
705                 710                 715                 720

Gly Lys Arg Asp Tyr Val Cys Glu Lys Cys Thr Lys Ala Tyr Leu Thr
                        725                 730                 735

Lys Tyr His Leu Thr Arg His Leu Lys Thr Cys Lys Gly Pro Thr Ser
            740                 745                 750

Ser Ser Ser Ala Pro Glu Glu Glu Glu Asp Asp Ser Glu Glu Glu
            755                 760                 765

Asp Leu Ala Asp Ser Val Gly Thr Glu Asp Cys Arg Ile Asn Ser Ala
770                 775                 780

Val Tyr Ser Ala Asp Glu Ser Leu Ser Ala His Lys
785                 790                 795

<210> SEQ ID NO 3
<211> LENGTH: 1065
<212> TYPE: DNA
<213> ORGANISM: Homo sapiens
<220> FEATURE:
<221> NAME/KEY: CDS
<222> LOCATION: (172)..(1065)

<400> SEQUENCE: 3
cggccgccgg cccgggaaaa tgctgggcat gtacgtgccg acaggttct ccctgaagtc      60 ctcccgggtt caggacggca tggggctcta cacggcccgc agagtgcgaa agggtgaaaa    120
gttcggaccc tttgctggag agaagagaat gcctgaagac ttggatgaaa a atg gat    177
                                                          Met Asp
                                                            1 tac agg ttg atg tgg gag gtt cgt ggg agt aag gga gaa gtt ttg tac    225
Tyr Arg Leu Met Trp Glu Val Arg Gly Ser Lys Gly Glu Val Leu Tyr
        5                   10                  15 att ttg gat gct acc aac cca cgg cac tcc aac tgg ctt cgc ttc gtt    273
Ile Leu Asp Ala Thr Asn Pro Arg His Ser Asn Trp Leu Arg Phe Val
    20                  25                  30 cat gag gca cca tct cag gag cag aag aac ttg gct gcc att caa gaa    321
His Glu Ala Pro Ser Gln Glu Gln Lys Asn Leu Ala Ala Ile Gln Glu
35                  40                  45                  50 gga gaa aac att ttc tat ttg gca gtt gaa gat ata gaa aca gac acg    369
Gly Glu Asn Ile Phe Tyr Leu Ala Val Glu Asp Ile Glu Thr Asp Thr
                55                  60                  65 gag ctt ctg att ggc tac ctg gat agt gac atg gag gct gag gag gaa    417
Glu Leu Leu Ile Gly Tyr Leu Asp Ser Asp Met Glu Ala Glu Glu Glu
            70                  75                  80 gaa cag caa att atg aca gtc atc aaa gaa ggg gaa gtt gaa aat tct    465
Glu Gln Gln Ile Met Thr Val Ile Lys Glu Gly Glu Val Glu Asn Ser
        85                  90                  95 aga aga caa tca aca gcg ggc aga aaa gat cgc ctt ggc tgt aaa gag    513
Arg Arg Gln Ser Thr Ala Gly Arg Lys Asp Arg Leu Gly Cys Lys Glu
    100                 105                 110 gac tat gct tgt cct caa tgt gaa tcg agt ttt acc agt gag gat att    561
Asp Tyr Ala Cys Pro Gln Cys Glu Ser Ser Phe Thr Ser Glu Asp Ile
115                 120                 125                 130 ctt gct gag cat ctc cag aca ttg cac cag aaa ccc aca gag gag aaa    609
Leu Ala Glu His Leu Gln Thr Leu His Gln Lys Pro Thr Glu Glu Lys
                135                 140                 145 gaa ttt aag tgc aag aac tgt ggg aag aaa ttc cca gtt aag cag gct    657
```

```
Glu Phe Lys Cys Lys Asn Cys Gly Lys Lys Phe Pro Val Lys Gln Ala
            150                 155                 160 ttg caa aga cat gtt ctt cag tgc aca gcg aaa agc agt ctg aag gag      705
Leu Gln Arg His Val Leu Gln Cys Thr Ala Lys Ser Ser Leu Lys Glu
        165                 170                 175 tct tcg cga agt ttt cag tgc tct gtt tgc aat tct tcc ttc agt tca      753
Ser Ser Arg Ser Phe Gln Cys Ser Val Cys Asn Ser Ser Phe Ser Ser
    180                 185                 190 gca tcg agt ttt gag cag cac cag gag act tgc cgg ggg gat gcc aag      801
Ala Ser Ser Phe Glu Gln His Gln Glu Thr Cys Arg Gly Asp Ala Lys
195                 200                 205                 210 ttt gtg tgc aag gct gac agc tgt gga aag agg ctg aag agc aag gat      849
Phe Val Cys Lys Ala Asp Ser Cys Gly Lys Arg Leu Lys Ser Lys Asp
            215                 220                 225 gcc ctg aaa aga cac cag gaa aat gtc cac act gga gat cct aag aaa      897
Ala Leu Lys Arg His Gln Glu Asn Val His Thr Gly Asp Pro Lys Lys
        230                 235                 240 aag ctt ata tgt tca gtg tgc aat aaa aag tgt tct tca gca tca agc      945
Lys Leu Ile Cys Ser Val Cys Asn Lys Lys Cys Ser Ser Ala Ser Ser
    245                 250                 255 cta cag gaa cat aga aag att cat gag ata ttt gat tgt caa gaa tgt      993
Leu Gln Glu His Arg Lys Ile His Glu Ile Phe Asp Cys Gln Glu Cys
260                 265                 270 atg aag aaa ttt att tca gct aat cag cta aaa cgt cat atg atc acc     1041
Met Lys Lys Phe Ile Ser Ala Asn Gln Leu Lys Arg His Met Ile Thr
275                 280                 285                 290 tcg tgc cta att ctt ggg ctc gag                                      1065
Ser Cys Leu Ile Leu Gly Leu Glu
            295

<210> SEQ ID NO 4
<211> LENGTH: 298
<212> TYPE: PRT
<213> ORGANISM: Homo sapiens

<400> SEQUENCE: 4

Met Asp Tyr Arg Leu Met Trp Glu Val Arg Gly Ser Lys Gly Glu Val
 1               5                  10                  15

Leu Tyr Ile Leu Asp Ala Thr Asn Pro Arg His Ser Asn Trp Leu Arg
            20                  25                  30

Phe Val His Glu Ala Pro Ser Gln Glu Gln Lys Asn Leu Ala Ala Ile
        35                  40                  45

Gln Glu Gly Glu Asn Ile Phe Tyr Leu Ala Val Glu Asp Ile Glu Thr
    50                  55                  60

Asp Thr Glu Leu Leu Ile Gly Tyr Leu Asp Ser Asp Met Glu Ala Glu
65                  70                  75                  80

Glu Glu Glu Gln Gln Ile Met Thr Val Ile Lys Glu Gly Glu Val Glu
                85                  90                  95

Asn Ser Arg Arg Gln Ser Thr Ala Gly Arg Lys Asp Arg Leu Gly Cys
            100                 105                 110

Lys Glu Asp Tyr Ala Cys Pro Gln Cys Glu Ser Ser Phe Thr Ser Glu
        115                 120                 125

Asp Ile Leu Ala Glu His Leu Gln Thr Leu His Gln Lys Pro Thr Glu
    130                 135                 140

Glu Lys Glu Phe Lys Cys Lys Asn Cys Gly Lys Lys Phe Pro Val Lys
145                 150                 155                 160

Gln Ala Leu Gln Arg His Val Leu Gln Cys Thr Ala Lys Ser Ser Leu
                165                 170                 175
```

-continued

```
Lys Glu Ser Ser Arg Ser Phe Gln Cys Ser Val Cys Asn Ser Ser Phe
            180                 185                 190

Ser Ser Ala Ser Ser Phe Glu Gln His Gln Glu Thr Cys Arg Gly Asp
        195                 200                 205

Ala Lys Phe Val Cys Lys Ala Asp Ser Cys Gly Lys Arg Leu Lys Ser
    210                 215                 220

Lys Asp Ala Leu Lys Arg His Gln Glu Asn Val His Thr Gly Asp Pro
225                 230                 235                 240

Lys Lys Lys Leu Ile Cys Ser Val Cys Asn Lys Lys Cys Ser Ser Ala
                245                 250                 255

Ser Ser Leu Gln Glu His Arg Lys Ile His Glu Ile Phe Asp Cys Gln
        260                 265                 270

Glu Cys Met Lys Lys Phe Ile Ser Ala Asn Gln Leu Lys Arg His Met
        275                 280                 285

Ile Thr Ser Cys Leu Ile Leu Gly Leu Glu
        290                 295

<210> SEQ ID NO 5
<211> LENGTH: 2262
<212> TYPE: DNA
<213> ORGANISM: Mus musculus
<220> FEATURE:
<221> NAME/KEY: CDS
<222> LOCATION: (79)..(2022)

<400> SEQUENCE: 5
tttcctcctc ccggccgccc caggcccgca ccccatctcc acgtgcggcg cctccggagc      60
gcggccgagc cacggagg atg ctg ggc atg tac gta cca gac agg ttc gcc       111
                    Met Leu Gly Met Tyr Val Pro Asp Arg Phe Ala
                     1                5                      10 ctg aag tcg tcc cgg gtc cag gac ggg atg ggg ctc tac acg gcc cgc       159
Leu Lys Ser Ser Arg Val Gln Asp Gly Met Gly Leu Tyr Thr Ala Arg
             15                  20                  25 cgc gtg cgc aag ggt gaa aaa ttt gga ccc ttc gct ggg gag aag cga       207
Arg Val Arg Lys Gly Glu Lys Phe Gly Pro Phe Ala Gly Glu Lys Arg
         30                  35                  40 atg cct gaa gac ttg gat gaa aat atg gac tac aga ctg atg tgg gtg       255
Met Pro Glu Asp Leu Asp Glu Asn Met Asp Tyr Arg Leu Met Trp Val
     45                  50                  55 gta cgt ggg agc aag gga gaa gtt ctg tat att ttg gat gct acc aac       303
Val Arg Gly Ser Lys Gly Glu Val Leu Tyr Ile Leu Asp Ala Thr Asn
 60                  65                  70                  75 cca aga cac tcc aac tgg ctt cgc ttt gtt cac gag gca cca tct cag       351
Pro Arg His Ser Asn Trp Leu Arg Phe Val His Glu Ala Pro Ser Gln
                 80                  85                  90 gag cgg aag aac ctg gct gcc att caa gaa gga gaa aaa tat ttc tac       399
Glu Arg Lys Asn Leu Ala Ala Ile Gln Glu Gly Glu Lys Tyr Phe Tyr
             95                 100                 105 ttg gca gtt gat gat ata gaa aca gat aca gag ctt ttg att ggc tac       447
Leu Ala Val Asp Asp Ile Glu Thr Asp Thr Glu Leu Leu Ile Gly Tyr
         110                 115                 120 ctg gac agt gat gtg gag gca gag gag gag gag caa caa gct ctg acc       495
Leu Asp Ser Asp Val Glu Ala Glu Glu Glu Glu Gln Gln Ala Leu Thr
     125                 130                 135 atg acc aaa gaa ggc aaa gtt gac cac tct aag gga cag ttg gca gct       543
Met Thr Lys Glu Gly Lys Val Asp His Ser Lys Gly Gln Leu Ala Ala
140                 145                 150                 155 gga agt aaa ggt act gca tct tcg ttt ggt gat ctg aag gaa gag aca       591
```

```
                Gly Ser Lys Gly Thr Ala Ser Ser Phe Gly Asp Leu Lys Glu Glu Thr
                                160                 165                 170 ttt gaa gag gaa ggt cac ctt ggc tgt gaa gag gac ttt gcc tgt cca         639
Phe Glu Glu Glu Gly His Leu Gly Cys Glu Glu Asp Phe Ala Cys Pro
                175                 180                 185 cag tgt gaa tcg agc ttt ccc agt gag gaa gtc ctt act gag cac ctt         687
Gln Cys Glu Ser Ser Phe Pro Ser Glu Glu Val Leu Thr Glu His Leu
                190                 195                 200 cag agc ttg cac cag aag ccc aca ggg gag aaa gag ttc aaa tgc gag         735
Gln Ser Leu His Gln Lys Pro Thr Gly Glu Lys Glu Phe Lys Cys Glu
                205                 210                 215 aac tgc ggg aag aaa ttc cct gtg agg cag gcc ttg cag aga cat gtt         783
Asn Cys Gly Lys Lys Phe Pro Val Arg Gln Ala Leu Gln Arg His Val
220                 225                 230                 235 ctt cag tgc aca gcg aaa agc agt ctg aag gag tct tcg cga agt ttt         831
Leu Gln Cys Thr Ala Lys Ser Ser Leu Lys Glu Ser Ser Arg Ser Phe
                240                 245                 250 cag tgc tct gtt tgc aat tct tcc ttc agt tca gca tcg agt ttt gag         879
Gln Cys Ser Val Cys Asn Ser Ser Phe Ser Ser Ala Ser Ser Phe Glu
                255                 260                 265 cag cac cag gag act tgc cgg ggg gat gcc aag ttt gtg tgc aag gct         927
Gln His Gln Glu Thr Cys Arg Gly Asp Ala Lys Phe Val Cys Lys Ala
                270                 275                 280 gac agc tgt gga aag agg ctg aag agc aag gat gcc ctg aaa aga cac         975
Asp Ser Cys Gly Lys Arg Leu Lys Ser Lys Asp Ala Leu Lys Arg His
        285                 290                 295 cag gaa aat gtc cac act gga gat cct aag aga aaa ctc ata tgc tcg        1023
Gln Glu Asn Val His Thr Gly Asp Pro Lys Arg Lys Leu Ile Cys Ser
300                 305                 310                 315 gtg tgc aat aga aaa tgt acc tca gtg tca agc ctg cag gag cac agg        1071
Val Cys Asn Arg Lys Cys Thr Ser Val Ser Ser Leu Gln Glu His Arg
                320                 325                 330 aag att cat gag ata ttt gat tgt caa gaa tgt atg aaa aag ttt att        1119
Lys Ile His Glu Ile Phe Asp Cys Gln Glu Cys Met Lys Lys Phe Ile
                335                 340                 345 tct gct aat cag ctg aag cgt cac atg att acc cac tca gaa aag cgg        1167
Ser Ala Asn Gln Leu Lys Arg His Met Ile Thr His Ser Glu Lys Arg
                350                 355                 360 cct tat aac tgt gag atc tgt aac aag tcc ttc aag agg ctc gat caa        1215
Pro Tyr Asn Cys Glu Ile Cys Asn Lys Ser Phe Lys Arg Leu Asp Gln
                365                 370                 375 gtg ggc gcc cac aaa gtg atc cac agt gag gac aaa ccc tac cag tgc        1263
Val Gly Ala His Lys Val Ile His Ser Glu Asp Lys Pro Tyr Gln Cys
380                 385                 390                 395 aag ctc tgt ggc aag ggc ttt gct cac aga aac gtt tac aag aac cac        1311
Lys Leu Cys Gly Lys Gly Phe Ala His Arg Asn Val Tyr Lys Asn His
                400                 405                 410 aag aag acc cac tcc gag gag aga cct ttc cag tgt gat gca tgt aaa        1359
Lys Lys Thr His Ser Glu Glu Arg Pro Phe Gln Cys Asp Ala Cys Lys
                415                 420                 425 gcc ttg ttc cgc acg ccc ttt tct ctg cag aga cac ctg tta atc cac        1407
Ala Leu Phe Arg Thr Pro Phe Ser Leu Gln Arg His Leu Leu Ile His
                430                 435                 440 aac agt gag agg act ttt aag tgt cac cac tgt gat gcc aca ttt aaa        1455
Asn Ser Glu Arg Thr Phe Lys Cys His His Cys Asp Ala Thr Phe Lys
                445                 450                 455 agg aag gat aca tta aac gtt cat gcc cag gtg gtc cat gaa aga cac        1503
Arg Lys Asp Thr Leu Asn Val His Ala Gln Val Val His Glu Arg His
460                 465                 470                 475
```

```
aag aag tac cga tgt gag ctg tgc aat aag gcc ttt gtc aca cct tca    1551
Lys Lys Tyr Arg Cys Glu Leu Cys Asn Lys Ala Phe Val Thr Pro Ser
            480                 485                 490 gtg ctt agg agt cat aag aag tca cac aca gga gaa aag gag aaa gtc    1599
Val Leu Arg Ser His Lys Lys Ser His Thr Gly Glu Lys Glu Lys Val
495                 500                 505 tgc cca tat tgt ggc cag aaa ttt gcc agc agt ggg acc ctg aga gtt    1647
Cys Pro Tyr Cys Gly Gln Lys Phe Ala Ser Ser Gly Thr Leu Arg Val
        510                 515                 520 cac atc cgg agc cac aca ggt gag cgc ccc tat caa tgc ccg tac tgt    1695
His Ile Arg Ser His Thr Gly Glu Arg Pro Tyr Gln Cys Pro Tyr Cys
    525                 530                 535 gaa aaa ggt ttc agt aaa aat gac gga ctg aag atg cac att cgt act    1743
Glu Lys Gly Phe Ser Lys Asn Asp Gly Leu Lys Met His Ile Arg Thr
540                 545                 550                 555 cac acc agg gag aag ccc tac cag tgc tca gag tgc agc aag gcc ttc    1791
His Thr Arg Glu Lys Pro Tyr Gln Cys Ser Glu Cys Ser Lys Ala Phe
                560                 565                 570 agc cag aag cgg ggc ctc gat gaa cac aag agg aca cac aca gga gaa    1839
Ser Gln Lys Arg Gly Leu Asp Glu His Lys Arg Thr His Thr Gly Glu
            575                 580                 585 aag cct ttt cag tgt gac gta tgt gac ttg gct ttt agc ctg aag aaa    1887
Lys Pro Phe Gln Cys Asp Val Cys Asp Leu Ala Phe Ser Leu Lys Lys
        590                 595                 600 atg ctt att cga cac aag atg aca cac aat cct aac cgt ccg atg gca    1935
Met Leu Ile Arg His Lys Met Thr His Asn Pro Asn Arg Pro Met Ala
    605                 610                 615 gag tgc cat ttc tgc cat aag aag ttt aca aga aat gac tac ctc aaa    1983
Glu Cys His Phe Cys His Lys Lys Phe Thr Arg Asn Asp Tyr Leu Lys
620                 625                 630                 635 gtg cac atg gac aac atc cat ggg gta gct gac agc taa gaggagcggc    2032
Val His Met Asp Asn Ile His Gly Val Ala Asp Ser
                640                 645 aaggaaccac accatgtgaa agagcttcta ctatgaatcc cagattcttc tcacctgatc   2092
ggcttaacag aaatagccac aaaggattca ttgatctgac agtgtttatg tgcctatctt   2152
tgtaatctat agatgcaaaa aaaatccttt taccaaaaat aaattcaaaa tagaaaacaa   2212
taatactttg tagattacag agtattctgg ctgattaaaa attaaatcag               2262
```

<210> SEQ ID NO 6
<211> LENGTH: 647
<212> TYPE: PRT
<213> ORGANISM: Mus musculus

<400> SEQUENCE: 6

```
Met Leu Gly Met Tyr Val Pro Asp Arg Phe Ala Leu Lys Ser Ser Arg
 1               5                  10                  15

Val Gln Asp Gly Met Gly Leu Tyr Thr Ala Arg Arg Val Arg Lys Gly
            20                  25                  30

Glu Lys Phe Gly Pro Phe Ala Gly Glu Lys Arg Met Pro Glu Asp Leu
        35                  40                  45

Asp Glu Asn Met Asp Tyr Arg Leu Met Trp Val Val Arg Gly Ser Lys
    50                  55                  60

Gly Glu Val Leu Tyr Ile Leu Asp Ala Thr Asn Pro Arg His Ser Asn
65                  70                  75                  80

Trp Leu Arg Phe Val His Glu Ala Pro Ser Gln Glu Arg Lys Asn Leu
                85                  90                  95

Ala Ala Ile Gln Glu Gly Glu Lys Tyr Phe Tyr Leu Ala Val Asp Asp
```

-continued

```
                100                 105                 110
Ile Glu Thr Asp Thr Glu Leu Leu Ile Gly Tyr Leu Asp Ser Asp Val
            115                 120                 125

Glu Ala Glu Glu Glu Gln Gln Ala Leu Thr Met Thr Lys Glu Gly
130                 135                 140

Lys Val Asp His Ser Lys Gly Gln Leu Ala Ala Gly Ser Lys Gly Thr
145                 150                 155                 160

Ala Ser Ser Phe Gly Asp Leu Lys Glu Thr Phe Glu Glu Gly
                165                 170                 175

His Leu Gly Cys Glu Glu Asp Phe Ala Cys Pro Gln Cys Glu Ser Ser
            180                 185                 190

Phe Pro Ser Glu Glu Val Leu Thr Glu His Leu Gln Ser Leu His Gln
                195                 200                 205

Lys Pro Thr Gly Glu Lys Glu Phe Lys Cys Glu Asn Cys Gly Lys Lys
            210                 215                 220

Phe Pro Val Arg Gln Ala Leu Gln Arg His Val Leu Gln Cys Thr Ala
225                 230                 235                 240

Lys Ser Ser Leu Lys Glu Ser Ser Arg Ser Phe Gln Cys Ser Val Cys
                245                 250                 255

Asn Ser Ser Phe Ser Ser Ala Ser Ser Phe Glu Gln His Gln Glu Thr
                260                 265                 270

Cys Arg Gly Asp Ala Lys Phe Val Cys Lys Ala Asp Ser Cys Gly Lys
            275                 280                 285

Arg Leu Lys Ser Lys Asp Ala Leu Lys Arg His Gln Glu Asn Val His
            290                 295                 300

Thr Gly Asp Pro Lys Arg Lys Leu Ile Cys Ser Val Cys Asn Arg Lys
305                 310                 315                 320

Cys Thr Ser Val Ser Ser Leu Gln Glu His Arg Lys Ile His Glu Ile
                325                 330                 335

Phe Asp Cys Gln Glu Cys Met Lys Lys Phe Ile Ser Ala Asn Gln Leu
            340                 345                 350

Lys Arg His Met Ile Thr His Ser Glu Lys Arg Pro Tyr Asn Cys Glu
            355                 360                 365

Ile Cys Asn Lys Ser Phe Lys Arg Leu Asp Gln Val Gly Ala His Lys
            370                 375                 380

Val Ile His Ser Glu Asp Lys Pro Tyr Gln Cys Lys Leu Cys Gly Lys
385                 390                 395                 400

Gly Phe Ala His Arg Asn Val Tyr Lys Asn His Lys Lys Thr His Ser
                405                 410                 415

Glu Glu Arg Pro Phe Gln Cys Asp Ala Cys Lys Ala Leu Phe Arg Thr
            420                 425                 430

Pro Phe Ser Leu Gln Arg His Leu Leu Ile His Asn Ser Glu Arg Thr
                435                 440                 445

Phe Lys Cys His His Cys Asp Ala Thr Phe Lys Arg Lys Asp Thr Leu
            450                 455                 460

Asn Val His Ala Gln Val Val His Glu Arg His Lys Lys Tyr Arg Cys
465                 470                 475                 480

Glu Leu Cys Asn Lys Ala Phe Val Thr Pro Ser Val Leu Arg Ser His
                485                 490                 495

Lys Lys Ser His Thr Gly Glu Lys Glu Lys Val Cys Pro Tyr Cys Gly
            500                 505                 510

Gln Lys Phe Ala Ser Ser Gly Thr Leu Arg Val His Ile Arg Ser His
            515                 520                 525
```

```
Thr Gly Glu Arg Pro Tyr Gln Cys Pro Tyr Cys Glu Lys Gly Phe Ser
    530                 535                 540
Lys Asn Asp Gly Leu Lys Met His Ile Arg Thr His Thr Arg Glu Lys
545                 550                 555                 560
Pro Tyr Gln Cys Ser Glu Cys Ser Lys Ala Phe Ser Gln Lys Arg Gly
                565                 570                 575
Leu Asp Glu His Lys Arg Thr His Thr Gly Leu Lys Pro Phe Gln Cys
            580                 585                 590
Asp Val Cys Asp Leu Ala Phe Ser Leu Lys Lys Met Leu Ile Arg His
        595                 600                 605
Lys Met Thr His Asn Pro Asn Arg Pro Met Ala Glu Cys His Phe Cys
    610                 615                 620
His Lys Lys Phe Thr Arg Asn Asp Tyr Leu Lys Val His Met Asp Asn
625                 630                 635                 640
Ile His Gly Val Ala Asp Ser
                645

<210> SEQ ID NO 7
<211> LENGTH: 1126
<212> TYPE: DNA
<213> ORGANISM: Mus musculus
<220> FEATURE:
<221> NAME/KEY: CDS
<222> LOCATION: (54)..(386)

<400> SEQUENCE: 7
tttcttacgt accagacagg ttcgccctga agtcgtcccg ggtccaggac ggg atg      56
                                                         Met
                                                          1 ggg ctc tac acg gcc cgc cgc gtg cgc aag ggt gaa aaa ttt gga ccc    104
Gly Leu Tyr Thr Ala Arg Arg Val Arg Lys Gly Glu Lys Phe Gly Pro
          5                  10                  15 ttc gct ggg gag aag cga atg cct gaa gac ttg gat gaa aat atg gac    152
Phe Ala Gly Glu Lys Arg Met Pro Glu Asp Leu Asp Glu Asn Met Asp
     20                  25                  30 tac aga ctg atg tgg gag gta cgt ggg agc aag gga gaa gtt ctg tat    200
Tyr Arg Leu Met Trp Glu Val Arg Gly Ser Lys Gly Glu Val Leu Tyr
 35                  40                  45 att ttg gat gct acc aac cca aga cac tcc aac tgg ctt cgc ttt gtt    248
Ile Leu Asp Ala Thr Asn Pro Arg His Ser Asn Trp Leu Arg Phe Val
 50                  55                  60                  65 cac gag gca cca tct cag gag cgg aag aac ctg gct gcc att caa gtg    296
His Glu Ala Pro Ser Gln Glu Arg Lys Asn Leu Ala Ala Ile Gln Val
                 70                  75                  80 agc ctg ttg gtt cat att tgt aca atg cac tgt gag agt aat gga tta    344
Ser Leu Leu Val His Ile Cys Thr Met His Cys Glu Ser Asn Gly Leu
             85                  90                  95 att tat aac tct gct cca tgt ctt caa ttt att tcc ctg tga            386
Ile Tyr Asn Ser Ala Pro Cys Leu Gln Phe Ile Ser Leu
        100                 105                 110 tcagcttcat ataacagtat ctaactcata aaagcaaaga aatcatgtag tcggcatatg   446
caggaaaacg caactgaact gtcagctaaa accagacttc tggctttatt ggaattcttg   506
ggggaatgaa ttacacggtc tgatactgtg cttggcagag cttgcgttca agtactttga   566
tttccttcag tgaatgtttt ttgatagcag tttggtttgc tagttgcttt ggatcgtctt   626
actctgctgt gggttattct ttgagaaagg aaaaaaaaaa aaaaaaaaa aaaaaaaaa    686 aaaaaaaaaa aaaataaagt gcagaagaag tcaaggagcc atggctgaca taaacatgaa   746
```

-continued

```
gggaagcaca gaacaactgc ctacactgtt ctagattgct catctctatg tgataattgc      806
ttttaggaac ttataatgta gaaattttct gactagtata ctgatttcac ttaagtctca      866
aggaactata gtgaggaaac atcacagcat aagtttaat ccaacaataa tacagttgtc       926
tgctatgtaa ttttctatcc tcagctaagt aatttctctg ttaatacaag tgttatagcc      986
gggtggtggt ggtgcgcgcc tttaatctca gcacttggga gacagaggca ggcggatttc     1046
tgagttcgag gccagcctgg tctacaaagt gagttccagg acagccagca gggctatacc     1106
aagaacccct gtcttgaaaa                                                  1126
```

<210> SEQ ID NO 8
<211> LENGTH: 110
<212> TYPE: PRT
<213> ORGANISM: Mus musculus

<400> SEQUENCE: 8

```
Met Gly Leu Tyr Thr Ala Arg Arg Val Arg Lys Gly Glu Lys Phe Gly
 1               5                  10                  15

Pro Phe Ala Gly Glu Lys Arg Met Pro Glu Asp Leu Asp Glu Asn Met
            20                  25                  30

Asp Tyr Arg Leu Met Trp Glu Val Arg Gly Ser Lys Gly Glu Val Leu
        35                  40                  45

Tyr Ile Leu Asp Ala Thr Asn Pro Arg His Ser Asn Trp Leu Arg Phe
    50                  55                  60

Val His Glu Ala Pro Ser Gln Glu Arg Lys Asn Leu Ala Ala Ile Gln
65                  70                  75                  80

Val Ser Leu Leu Val His Ile Cys Thr Met His Cys Glu Ser Asn Gly
                85                  90                  95

Leu Ile Tyr Asn Ser Ala Pro Cys Leu Gln Phe Ile Ser Leu
            100                 105                 110
```

<210> SEQ ID NO 9
<211> LENGTH: 2488
<212> TYPE: DNA
<213> ORGANISM: Homo sapiens
<220> FEATURE:
<221> NAME/KEY: CDS
<222> LOCATION: (1)..(1707)

<400> SEQUENCE: 9

```
aaa gcg cag cag ccc acg gcg gtt gag tcg ggc gcc cag gtc cgt ccg        48
Lys Ala Gln Gln Pro Thr Ala Val Glu Ser Gly Ala Gln Val Arg Pro
 1               5                  10                  15 cac tct cgc gcc ctc cgc ggg cct ccc aat ttt ctc gct tgc agg tcg        96
His Ser Arg Ala Leu Arg Gly Pro Pro Asn Phe Leu Ala Cys Arg Ser
            20                  25                  30 gga ggt ttc cgg gcg gca caa tct cta gga ctc tcc tcc cgc gct gct       144
Gly Gly Phe Arg Ala Ala Gln Ser Leu Gly Leu Ser Ser Arg Ala Ala
        35                  40                  45 cag ggg cat gta gcg cac gca ggg cgc aca ctc tcg cgc acc cgc acg       192
Gln Gly His Val Ala His Ala Gly Arg Thr Leu Ser Arg Thr Arg Thr
    50                  55                  60 ctc acc gag aca ccc gcg ctg gct ggt ctc tcg gcc ctg ccg gtg tcg       240
Leu Thr Glu Thr Pro Ala Leu Ala Gly Leu Ser Ala Leu Pro Val Ser
65                  70                  75                  80 cag ctg ccg gtg ttc gcg cct cta gcc gcc gct gcc gtc gcc gcc gag       288
Gln Leu Pro Val Phe Ala Pro Leu Ala Ala Ala Ala Val Ala Ala Glu
                85                  90                  95
```

```
ccg ctg ccc ccc aag gaa ctg tgc ctc ggc gcc acc tcc ggc ccc ggg      336
Pro Leu Pro Pro Lys Glu Leu Cys Leu Gly Ala Thr Ser Gly Pro Gly
            100                 105                 110 ccc gtc aag tgc ggt ggt ggt ggc ggc ggc ggg gag ggt cgc ggc          384
Pro Val Lys Cys Gly Gly Gly Gly Gly Gly Gly Glu Gly Arg Gly
        115                 120                 125 gcc ccg cgc ttc cgc tgc agc gca gag gag ctg gac tat tac ctg tat      432
Ala Pro Arg Phe Arg Cys Ser Ala Glu Glu Leu Asp Tyr Tyr Leu Tyr
130                 135                 140 ggc cag cag cgc atg gag atc atc ccg ctc aac cag cac acc agc gac      480
Gly Gln Gln Arg Met Glu Ile Ile Pro Leu Asn Gln His Thr Ser Asp
145                 150                 155                 160 ccc aac aac cgt tgc gac atg tgc gcg gac aac cgc aac ggc gag tgc      528
Pro Asn Asn Arg Cys Asp Met Cys Ala Asp Asn Arg Asn Gly Glu Cys
                165                 170                 175 cct atg cat ggg cca ctg cac tcg ctg cgc cgg ctt gtg ggc acc agc      576
Pro Met His Gly Pro Leu His Ser Leu Arg Arg Leu Val Gly Thr Ser
            180                 185                 190 agc gct gcg gcc gcc gcg ccc ccg ccg gag ctg ccg gag tgg ctg cgg      624
Ser Ala Ala Ala Ala Ala Pro Pro Pro Glu Leu Pro Glu Trp Leu Arg
        195                 200                 205 gac ctg cct cgc gag gtg tgc ctc tgc acc agt act gtg ccc ggc ctg      672
Asp Leu Pro Arg Glu Val Cys Leu Cys Thr Ser Thr Val Pro Gly Leu
210                 215                 220 gcc tac ggc atc tgc gcg gcg cag agg atc cag caa ggc acc tgg att      720
Ala Tyr Gly Ile Cys Ala Ala Gln Arg Ile Gln Gln Gly Thr Trp Ile
225                 230                 235                 240 gga cct ttc caa ggc gtg ctt ctg ccc cca gag aag gtg cag gca ggc      768
Gly Pro Phe Gln Gly Val Leu Leu Pro Pro Glu Lys Val Gln Ala Gly
                245                 250                 255 gcc gtg agg aac acg cag cat ctc tgg gag ata tat gac cag gat ggg      816
Ala Val Arg Asn Thr Gln His Leu Trp Glu Ile Tyr Asp Gln Asp Gly
            260                 265                 270 aca cta cag cac ttt att gat ggt ggg gaa cct agt aag tcg agc tgg      864
Thr Leu Gln His Phe Ile Asp Gly Gly Glu Pro Ser Lys Ser Ser Trp
        275                 280                 285 atg agg tat atc cga tgt gca agg cac tgc gga gaa cag aat cta aca      912
Met Arg Tyr Ile Arg Cys Ala Arg His Cys Gly Glu Gln Asn Leu Thr
290                 295                 300 gta gtt cag tac agg tcg aat ata ttc tac cga gcc tgt ata gat atc      960
Val Val Gln Tyr Arg Ser Asn Ile Phe Tyr Arg Ala Cys Ile Asp Ile
305                 310                 315                 320 cct agg ggc acc gag ctt ctg gtg tgg tac aat gac agc tat acg tct     1008
Pro Arg Gly Thr Glu Leu Leu Val Trp Tyr Asn Asp Ser Tyr Thr Ser
                325                 330                 335 ttc ttt ggg atc cct tta caa tgc att gcc cag gat gaa aac tta aat     1056
Phe Phe Gly Ile Pro Leu Gln Cys Ile Ala Gln Asp Glu Asn Leu Asn
            340                 345                 350 gtc cct tca acg gta atg gaa gcc atg tgc aga caa gac gcc ctg cag     1104
Val Pro Ser Thr Val Met Glu Ala Met Cys Arg Gln Asp Ala Leu Gln
        355                 360                 365 ccc ttc aac aaa agc agc aaa ctc gcc cct acc acc cag cag cgc tcc     1152
Pro Phe Asn Lys Ser Ser Lys Leu Ala Pro Thr Thr Gln Gln Arg Ser
370                 375                 380 gtt gtt ttc ccc cag act ccg tgc agc agg aac ttc tct ctt ctg gat     1200
Val Val Phe Pro Gln Thr Pro Cys Ser Arg Asn Phe Ser Leu Leu Asp
385                 390                 395                 400 aag tct ggg ccc att gaa tca gga ttt aat caa atc aac gtg aaa aac     1248
Lys Ser Gly Pro Ile Glu Ser Gly Phe Asn Gln Ile Asn Val Lys Asn
                405                 410                 415
```

```
cag cga gtc ctg gca agc cca act tcc aca agc cag ctc cac tcg gag      1296
Gln Arg Val Leu Ala Ser Pro Thr Ser Thr Ser Gln Leu His Ser Glu
        420                 425                 430 ttc agt gac tgg cat ctt tgg aaa tgt ggg cag tgc ttt aag act ttc      1344
Phe Ser Asp Trp His Leu Trp Lys Cys Gly Gln Cys Phe Lys Thr Phe
    435                 440                 445 acc cag cgg atc ctc tta cag atg cac gtg tgc acg cag aac acc gac      1392
Thr Gln Arg Ile Leu Leu Gln Met His Val Cys Thr Gln Asn Thr Asp
450                 455                 460 aga ccc tac caa tgc ggc cac tgc tcc cag tcc ttt tcc cag cct tca      1440
Arg Pro Tyr Gln Cys Gly His Cys Ser Gln Ser Phe Ser Gln Pro Ser
465                 470                 475                 480 gaa ctg agg aac cac gtg gtc act cac tct agt gac cgg cct ttc aag      1488
Glu Leu Arg Asn His Val Val Thr His Ser Ser Asp Arg Pro Phe Lys
                485                 490                 495 tgc ggc tac tgt ggt cgt gcc ttt gcc ggg gcc acc acc ctc aac aac      1536
Cys Gly Tyr Cys Gly Arg Ala Phe Ala Gly Ala Thr Thr Leu Asn Asn
            500                 505                 510 cac atc cga acc cac act gga gaa aag ccc ttc aag tgc gag agg tgt      1584
His Ile Arg Thr His Thr Gly Glu Lys Pro Phe Lys Cys Glu Arg Cys
        515                 520                 525 gag agg agc ttc acg cag gcc acc cag ttg agc cga cac cag cgg atg      1632
Glu Arg Ser Phe Thr Gln Ala Thr Gln Leu Ser Arg His Gln Arg Met
    530                 535                 540 ccc aat gag tgc aag cca ata act gag agc cca gaa tca atc gaa gtg      1680
Pro Asn Glu Cys Lys Pro Ile Thr Glu Ser Pro Glu Ser Ile Glu Val
545                 550                 555                 560 gat aac gga ttg act ggt tgg aat taa actgcaagga atgtcatgat            1727
Asp Asn Gly Leu Thr Gly Trp Asn
                565 taaatgtcac ggacacttaa gcaaaaccaa agatttcctt tgagcaactt tcaatcagtc    1787 ccagaaacca aaagcagtaa taaaataagt aagattgtta gagatattga tcctggcatg    1847 gaagtcagac caggaaagag attatttatt tatgactaag ggatgagact tatttcagtg    1907 gaaaacttaa cttgggattg gtaaacattc ccagtcccac catgtatttt gctttgtttt    1967 ctaaaaagct ttttaaaaac tgttatttaa ttaccaaagg gaggaatcgt atgggttctt    2027 ctgcccaccg ttgtgactaa gaatgcacag ggacttggtt ctcgttgcac cttttttag     2087 taacatgttt catggggacc cactgtacag cccttcattc tgctgtgtca gtttggcctg    2147 gcctgacact ggcttgccca gcggggacca cggaagcaga gtgagagcct cgctgagtc     2207 aatgctacct tcagccccag acgcatccca tttccatgtc ttccatgctc actgctcatg    2267 cactttttac acggtttctt ccaaacagcc cggtcttgat gcaggagagt ctggaaaagg    2327 aagaaaatgg tttcagtttc aaaattcaaa ggaaaaagtt gaggacttat tttgtcctgt    2387 caagattgca agaacatgta aaatgtacgg agcttcataa tacgttatat tgttccgaag    2447 cagctcgttg agaaacattt gttttcaata acatttagc t                        2488

<210> SEQ ID NO 10
<211> LENGTH: 568
<212> TYPE: PRT
<213> ORGANISM: Homo sapiens

<400> SEQUENCE: 10

Lys Ala Gln Gln Pro Thr Ala Val Glu Ser Gly Ala Gln Val Arg Pro
 1               5                  10                  15

His Ser Arg Ala Leu Arg Gly Pro Pro Asn Phe Leu Ala Cys Arg Ser
```

-continued

```
                20                  25                  30
Gly Gly Phe Arg Ala Ala Gln Ser Leu Gly Leu Ser Arg Ala Ala
            35                  40                  45

Gln Gly His Val Ala His Ala Gly Arg Thr Leu Ser Arg Thr Arg Thr
    50                  55                  60

Leu Thr Glu Thr Pro Ala Leu Ala Gly Leu Ser Ala Leu Pro Val Ser
65                  70                  75                  80

Gln Leu Pro Val Phe Ala Pro Leu Ala Ala Ala Val Ala Ala Glu
                85                  90                  95

Pro Leu Pro Pro Lys Glu Leu Cys Leu Gly Ala Thr Ser Gly Pro Gly
            100                 105                 110

Pro Val Lys Cys Gly Gly Gly Gly Gly Gly Gly Glu Gly Arg Gly
            115                 120                 125

Ala Pro Arg Phe Arg Cys Ser Ala Glu Glu Leu Asp Tyr Tyr Leu Tyr
    130                 135                 140

Gly Gln Gln Arg Met Glu Ile Ile Pro Leu Asn Gln His Thr Ser Asp
145                 150                 155                 160

Pro Asn Asn Arg Cys Asp Met Cys Ala Asp Asn Arg Asn Gly Glu Cys
                165                 170                 175

Pro Met His Gly Pro Leu His Ser Leu Arg Arg Leu Val Gly Thr Ser
            180                 185                 190

Ser Ala Ala Ala Ala Pro Pro Glu Leu Pro Glu Trp Leu Arg
    195                 200                 205

Asp Leu Pro Arg Glu Val Cys Leu Cys Thr Ser Thr Val Pro Gly Leu
    210                 215                 220

Ala Tyr Gly Ile Cys Ala Ala Gln Arg Ile Gln Gln Gly Thr Trp Ile
225                 230                 235                 240

Gly Pro Phe Gln Gly Val Leu Leu Pro Pro Glu Lys Val Gln Ala Gly
                245                 250                 255

Ala Val Arg Asn Thr Gln His Leu Trp Glu Ile Tyr Asp Gln Asp Gly
            260                 265                 270

Thr Leu Gln His Phe Ile Asp Gly Gly Glu Pro Ser Lys Ser Ser Trp
    275                 280                 285

Met Arg Tyr Ile Arg Cys Ala Arg His Cys Gly Glu Gln Asn Leu Thr
    290                 295                 300

Val Val Gln Tyr Arg Ser Asn Ile Phe Tyr Arg Ala Cys Ile Asp Ile
305                 310                 315                 320

Pro Arg Gly Thr Glu Leu Leu Val Trp Tyr Asn Asp Ser Tyr Thr Ser
            325                 330                 335

Phe Phe Gly Ile Pro Leu Gln Cys Ile Ala Gln Asp Glu Asn Leu Asn
            340                 345                 350

Val Pro Ser Thr Val Met Glu Ala Met Cys Arg Gln Asp Ala Leu Gln
            355                 360                 365

Pro Phe Asn Lys Ser Ser Lys Leu Ala Pro Thr Thr Gln Gln Arg Ser
    370                 375                 380

Val Val Phe Pro Gln Thr Pro Cys Ser Arg Asn Phe Ser Leu Leu Asp
385                 390                 395                 400

Lys Ser Gly Pro Ile Glu Ser Gly Phe Asn Gln Ile Asn Val Lys Asn
                405                 410                 415

Gln Arg Val Leu Ala Ser Pro Thr Thr Ser Gln Leu His Ser Glu
            420                 425                 430

Phe Ser Asp Trp His Leu Trp Lys Cys Gly Gln Cys Phe Lys Thr Phe
    435                 440                 445
```

```
Thr Gln Arg Ile Leu Leu Gln Met His Val Cys Thr Gln Asn Thr Asp
    450                 455                 460
Arg Pro Tyr Gln Cys Gly His Cys Ser Gln Ser Phe Ser Gln Pro Ser
465                 470                 475                 480
Glu Leu Arg Asn His Val Val Thr His Ser Ser Asp Arg Pro Phe Lys
                485                 490                 495
Cys Gly Tyr Cys Gly Arg Ala Phe Ala Gly Ala Thr Thr Leu Asn Asn
            500                 505                 510
His Ile Arg Thr His Thr Gly Glu Lys Pro Phe Lys Cys Glu Arg Cys
        515                 520                 525
Glu Arg Ser Phe Thr Gln Ala Thr Gln Leu Ser Arg His Gln Arg Met
    530                 535                 540
Pro Asn Glu Cys Lys Pro Ile Thr Glu Ser Pro Glu Ser Ile Glu Val
545                 550                 555                 560
Asp Asn Gly Leu Thr Gly Trp Asn
                565

<210> SEQ ID NO 11
<211> LENGTH: 2236
<212> TYPE: DNA
<213> ORGANISM: Homo sapiens
<220> FEATURE:
<221> NAME/KEY: CDS
<222> LOCATION: (1)..(1455)

<400> SEQUENCE: 11 aaa gcg cag cag ccc acg gcg gtt gag tcg ggc gcc cag gtc cgt ccg      48
Lys Ala Gln Gln Pro Thr Ala Val Glu Ser Gly Ala Gln Val Arg Pro
  1               5                  10                  15 cac tct cgc gcc ctc cgc ggg cct ccc aat ttt ctc gct tgc agg tcg      96
His Ser Arg Ala Leu Arg Gly Pro Pro Asn Phe Leu Ala Cys Arg Ser
             20                  25                  30 gga ggt ttc cgg gcg gca caa tct cta gga ctc tcc tcc cgc gct gct     144
Gly Gly Phe Arg Ala Ala Gln Ser Leu Gly Leu Ser Ser Arg Ala Ala
         35                  40                  45 cag ggg cat gta gcg cac gca ggg cgc aca ctc tcg cgc acc cgc acg     192
Gln Gly His Val Ala His Ala Gly Arg Thr Leu Ser Arg Thr Arg Thr
     50                  55                  60 ctc acc gag aca ccc gcg ctg gct ggt ctc tcg gcc ctg ccg gtg tcg     240
Leu Thr Glu Thr Pro Ala Leu Ala Gly Leu Ser Ala Leu Pro Val Ser
 65                  70                  75                  80 cag ctg ccg gtg ttc gcg cct cta gcc gcc gct gcc gtc gcc gcc gag     288
Gln Leu Pro Val Phe Ala Pro Leu Ala Ala Ala Ala Val Ala Ala Glu
                 85                  90                  95 ccg ctg ccc ccc aag gaa ctg tgc ctc ggc gcc acc tcc ggc ccc ggg     336
Pro Leu Pro Pro Lys Glu Leu Cys Leu Gly Ala Thr Ser Gly Pro Gly
            100                 105                 110 ccc gtc aag tgc ggt ggt ggt ggc ggc ggc ggg gag ggt cgc ggc         384
Pro Val Lys Cys Gly Gly Gly Gly Gly Gly Gly Glu Gly Arg Gly
        115                 120                 125 gcc ccg cgc ttc cgc tgc agc gca gag gag ctg gac tat tac ctg tat     432
Ala Pro Arg Phe Arg Cys Ser Ala Glu Glu Leu Asp Tyr Tyr Leu Tyr
    130                 135                 140 ggc cag cag cgc atg gag atc atc ccg ctc aac cag cac acc agc gac     480
Gly Gln Gln Arg Met Glu Ile Ile Pro Leu Asn Gln His Thr Ser Asp
145                 150                 155                 160 ccc aac aac cgt tgc gac atg tgc gcg gac aac cgc aac ggc gag tgc     528
Pro Asn Asn Arg Cys Asp Met Cys Ala Asp Asn Arg Asn Gly Glu Cys
                165                 170                 175
```

```
cct atg cat ggg cca ctg cac tcg ctg cgc cgg ctt gtg ggc acc agc        576
Pro Met His Gly Pro Leu His Ser Leu Arg Arg Leu Val Gly Thr Ser
        180                 185                 190 agc gct gcg gcc gcc gcg ccc ccg gag ctg ccg gag tgg ctg cgg            624
Ser Ala Ala Ala Ala Ala Pro Pro Glu Leu Pro Glu Trp Leu Arg
    195                 200                 205 gac ctg cct cgc gag gtg tgc ctc tgc acc agt act gtg ccc ggc ctg        672
Asp Leu Pro Arg Glu Val Cys Leu Cys Thr Ser Thr Val Pro Gly Leu
210                 215                 220 gcc tac ggc atc tgc gcg gcg cag agg atc cag caa ggc acc tgg att        720
Ala Tyr Gly Ile Cys Ala Ala Gln Arg Ile Gln Gln Gly Thr Trp Ile
225                 230                 235                 240 gga cct ttc caa ggc gtg ctt ctg ccc cca gag aag gtg cag gca ggc        768
Gly Pro Phe Gln Gly Val Leu Leu Pro Pro Glu Lys Val Gln Ala Gly
                245                 250                 255 gcc gtg agg aac acg cag cat ctc tgg gag tta aat gtc cct tca acg        816
Ala Val Arg Asn Thr Gln His Leu Trp Glu Leu Asn Val Pro Ser Thr
            260                 265                 270 gta atg gaa gcc atg tgc aga caa gac gcc ctg cag ccc ttc aac aaa        864
Val Met Glu Ala Met Cys Arg Gln Asp Ala Leu Gln Pro Phe Asn Lys
        275                 280                 285 agc agc aaa ctc gcc cct acc acc cag cag cgc tcc gtt gtt ttc ccc        912
Ser Ser Lys Leu Ala Pro Thr Thr Gln Gln Arg Ser Val Val Phe Pro
    290                 295                 300 cag act ccg tgc agc agg aac ttc tct ctt ctg gat aag tct ggg ccc        960
Gln Thr Pro Cys Ser Arg Asn Phe Ser Leu Leu Asp Lys Ser Gly Pro
305                 310                 315                 320 att gaa tca gga ttt aat caa atc aac gtg aaa aac cag cga gtc ctg       1008
Ile Glu Ser Gly Phe Asn Gln Ile Asn Val Lys Asn Gln Arg Val Leu
                325                 330                 335 gca agc cca act tcc aca agc cag ctc cac tcg gag ttc agt gac tgg       1056
Ala Ser Pro Thr Ser Thr Ser Gln Leu His Ser Glu Phe Ser Asp Trp
            340                 345                 350 cat ctt tgg aaa tgt ggg cag tgc ttt aag act ttc acc cag cgg atc       1104
His Leu Trp Lys Cys Gly Gln Cys Phe Lys Thr Phe Thr Gln Arg Ile
        355                 360                 365 ctc tta cag atg cac gtg tgc acg cag aac acc gac aga ccc tac caa       1152
Leu Leu Gln Met His Val Cys Thr Gln Asn Thr Asp Arg Pro Tyr Gln
    370                 375                 380 tgc ggc cac tgc tcc cag tcc ttt tcc cag cct tca gaa ctg agg aac       1200
Cys Gly His Cys Ser Gln Ser Phe Ser Gln Pro Ser Glu Leu Arg Asn
385                 390                 395                 400 cac gtg gtc act cac tct agt gac cgg cct ttc aag tgc ggc tac tgt       1248
His Val Val Thr His Ser Ser Asp Arg Pro Phe Lys Cys Gly Tyr Cys
                405                 410                 415 ggt cgt gcc ttt gcc ggg gcc acc acc ctc aac aac cac atc cga acc       1296
Gly Arg Ala Phe Ala Gly Ala Thr Thr Leu Asn Asn His Ile Arg Thr
            420                 425                 430 cac act gga gaa aag ccc ttc aag tgc gag agg tgt gag agg agc ttc       1344
His Thr Gly Glu Lys Pro Phe Lys Cys Glu Arg Cys Glu Arg Ser Phe
        435                 440                 445 acg cag gcc acc cag ttg agc cga cac cag cgg atg ccc aat gag tgc       1392
Thr Gln Ala Thr Gln Leu Ser Arg His Gln Arg Met Pro Asn Glu Cys
    450                 455                 460 aag cca ata act gag agc cca gaa tca atc gaa gtg gat aac gga ttg       1440
Lys Pro Ile Thr Glu Ser Pro Glu Ser Ile Glu Val Asp Asn Gly Leu
465                 470                 475                 480 act ggt tgg aat taa actgcaagga atgtcatgat taaatgtcac ggacacttaa      1495
Thr Gly Trp Asn
```

```
                   485
gcaaaaccaa agatttcctt tgagcaactt tcaatcagtc ccagaaacca aaagcagtaa    1555
taaaataagt aagattgtta gagatattga tcctggcatg gaagtcagac caggaaagag    1615
attatttatt tatgactaag ggatgagact tatttcagtg gaaaacttaa cttgggattg    1675
gtaaacattc ccagtcccac catgtatttt gctttgtttt ctaaaaagct ttttaaaaac    1735
tgttatttaa ttaccaaagg gaggaatcgt atgggttctt ctgcccaccg ttgtgactaa    1795
gaatgcacag ggacttggtt ctcgttgcac ctttttttag taacatgttt catggggacc    1855
cactgtacag cccttcattc tgctgtgtca gtttggcctg gcctgacact ggcttgccca    1915
gcggggacca cggaagcaga gtgagagcct tcgctgagtc aatgctacct tcagccccag    1975
acgcatccca tttccatgtc ttccatgctc actgctcatg cactttttac acggtttctt    2035
ccaaacagcc cggtcttgat gcaggagagt ctggaaaagg aagaaaatgg tttcagtttc    2095
aaaattcaaa ggaaaagtt gaggactat tttgtcctgt caagattgca agaacatgta     2155
aaatgtacgg agcttcataa tacgttatat tgttccgaag cagctcgttg agaaacattt    2215
gttttcaata acattttagc t                                              2236
```

<210> SEQ ID NO 12
<211> LENGTH: 484
<212> TYPE: PRT
<213> ORGANISM: Homo sapiens

<400> SEQUENCE: 12

```
Lys Ala Gln Gln Pro Thr Ala Val Glu Ser Gly Ala Gln Val Arg Pro
  1               5                  10                  15

His Ser Arg Ala Leu Arg Gly Pro Pro Asn Phe Leu Ala Cys Arg Ser
             20                  25                  30

Gly Gly Phe Arg Ala Ala Gln Ser Leu Gly Leu Ser Ser Arg Ala Ala
         35                  40                  45

Gln Gly His Val Ala His Ala Gly Arg Thr Leu Ser Arg Thr Arg Thr
     50                  55                  60

Leu Thr Glu Thr Pro Ala Leu Ala Gly Leu Ser Ala Leu Pro Val Ser
 65                  70                  75                  80

Gln Leu Pro Val Phe Ala Pro Leu Ala Ala Ala Val Ala Ala Glu
                 85                  90                  95

Pro Leu Pro Pro Lys Glu Leu Cys Leu Gly Ala Thr Ser Gly Pro Gly
            100                 105                 110

Pro Val Lys Cys Gly Gly Gly Gly Gly Gly Gly Glu Gly Arg Gly
        115                 120                 125

Ala Pro Arg Phe Arg Cys Ser Ala Glu Glu Leu Asp Tyr Tyr Leu Tyr
    130                 135                 140

Gly Gln Gln Arg Met Glu Ile Ile Pro Leu Asn Gln His Thr Ser Asp
145                 150                 155                 160

Pro Asn Asn Arg Cys Asp Met Cys Ala Asp Asn Arg Asn Gly Glu Cys
                165                 170                 175

Pro Met His Gly Pro Leu His Ser Leu Arg Arg Leu Val Gly Thr Ser
            180                 185                 190

Ser Ala Ala Ala Ala Pro Pro Glu Leu Pro Glu Trp Leu Arg
        195                 200                 205

Asp Leu Pro Arg Glu Val Cys Leu Cys Thr Ser Thr Val Pro Gly Leu
    210                 215                 220

Ala Tyr Gly Ile Cys Ala Ala Gln Arg Ile Gln Gln Gly Thr Trp Ile
```

-continued

```
                225                 230                 235                 240
Gly Pro Phe Gln Gly Val Leu Leu Pro Pro Glu Lys Val Gln Ala Gly
                245                 250                 255

Ala Val Arg Asn Thr Gln His Leu Trp Glu Leu Asn Val Pro Ser Thr
            260                 265                 270

Val Met Glu Ala Met Cys Arg Gln Asp Ala Leu Gln Pro Phe Asn Lys
        275                 280                 285

Ser Ser Lys Leu Ala Pro Thr Thr Gln Gln Arg Ser Val Val Phe Pro
    290                 295                 300

Gln Thr Pro Cys Ser Arg Asn Phe Ser Leu Leu Asp Lys Ser Gly Pro
305                 310                 315                 320

Ile Glu Ser Gly Phe Asn Gln Ile Asn Val Lys Asn Gln Arg Val Leu
                325                 330                 335

Ala Ser Pro Thr Ser Thr Ser Gln Leu His Ser Glu Phe Ser Asp Trp
            340                 345                 350

His Leu Trp Lys Cys Gly Gln Cys Phe Lys Thr Phe Thr Gln Arg Ile
        355                 360                 365

Leu Leu Gln Met His Val Cys Thr Gln Asn Thr Asp Arg Pro Tyr Gln
    370                 375                 380

Cys Gly His Cys Ser Gln Ser Phe Ser Gln Pro Ser Glu Leu Arg Asn
385                 390                 395                 400

His Val Val Thr His Ser Ser Asp Arg Pro Phe Lys Cys Gly Tyr Cys
                405                 410                 415

Gly Arg Ala Phe Ala Gly Ala Thr Thr Leu Asn Asn His Ile Arg Thr
            420                 425                 430

His Thr Gly Glu Lys Pro Phe Lys Cys Glu Arg Cys Glu Arg Ser Phe
        435                 440                 445

Thr Gln Ala Thr Gln Leu Ser Arg His Gln Arg Met Pro Asn Glu Cys
    450                 455                 460

Lys Pro Ile Thr Glu Ser Pro Glu Ser Ile Glu Val Asp Asn Gly Leu
465                 470                 475                 480

Thr Gly Trp Asn

<210> SEQ ID NO 13
<211> LENGTH: 1427
<212> TYPE: DNA
<213> ORGANISM: Homo sapiens
<220> FEATURE:
<221> NAME/KEY: CDS
<222> LOCATION: (142)..(1365)

<400> SEQUENCE: 13
atcattccct tactcgaatg aattaaagta caggattggg gctaaataat gtgagtgcca      60
cgctctttct gaagctctta tatcaaggaa catgcattac aactttccta atccctgctt     120
ccctcacttc cagattgtga g atg tgt cag aac ttc ttc att gac agc tgt       171
                         Met Cys Gln Asn Phe Phe Ile Asp Ser Cys
                           1               5                  10 gct gct cat ggg ccc cct aca ttt gta aag gac agt gca gtg gac aag       219
Ala Ala His Gly Pro Pro Thr Phe Val Lys Asp Ser Ala Val Asp Lys
                 15                  20                  25 ggg cat ccc aac cgt tca gcc ctc agt ctg ccc ccg ggg ctg aga att       267
Gly His Pro Asn Arg Ser Ala Leu Ser Leu Pro Pro Gly Leu Arg Ile
         30                  35                  40 ggg cca tca ggc atc cct cag gct ggg ctt gga gta tgg aac gag gca       315
Gly Pro Ser Gly Ile Pro Gln Ala Gly Leu Gly Val Trp Asn Glu Ala
     45                  50                  55
```

-continued

```
tct gat ctg cca ctg ggt ctg cac ttt ggc ccc tat gag ggc cga att      363
Ser Asp Leu Pro Leu Gly Leu His Phe Gly Pro Tyr Glu Gly Arg Ile
    60              65                  70 aca gaa gac gaa gag gca gcc aac agt gga tat tcc tgg cta atc acc      411
Thr Glu Asp Glu Glu Ala Ala Asn Ser Gly Tyr Ser Trp Leu Ile Thr
75              80                  85                  90 aag ggg aga aac tgc tat gag tat gtg gat gga aaa gat aaa tcc tcg      459
Lys Gly Arg Asn Cys Tyr Glu Tyr Val Asp Gly Lys Asp Lys Ser Ser
                95                  100                 105 gcc aac tgg atg agg tat gtg aac tgt gcc cgg gat gat gaa gag cag      507
Ala Asn Trp Met Arg Tyr Val Asn Cys Ala Arg Asp Asp Glu Glu Gln
            110                 115                 120 aac ctg gtg gcc ttc cag tac cac agg cag atc ttc tat aga acc tgc      555
Asn Leu Val Ala Phe Gln Tyr His Arg Gln Ile Phe Tyr Arg Thr Cys
        125                 130                 135 cga gtc att agg cca ggc tgt gaa ctg ctg gtc tgg tat ggg gat gag      603
Arg Val Ile Arg Pro Gly Cys Glu Leu Leu Val Trp Tyr Gly Asp Glu
    140                 145                 150 tat ggc cag gaa ctg ggc atc aag tgg ggc agc aag tgg aag aaa gag      651
Tyr Gly Gln Glu Leu Gly Ile Lys Trp Gly Ser Lys Trp Lys Lys Glu
155                 160                 165                 170 ctc atg gca ggg aga gaa cca aag cca gag atc cat cca tgt ccc tca      699
Leu Met Ala Gly Arg Glu Pro Lys Pro Glu Ile His Pro Cys Pro Ser
                175                 180                 185 tgc tgt ctg gcc ttt tca agt caa aaa ttt ctc agt caa cat gtg gaa      747
Cys Cys Leu Ala Phe Ser Ser Gln Lys Phe Leu Ser Gln His Val Glu
            190                 195                 200 cgc aat cac tcc tct cag aac ttc cca gga cca tct gca aga aaa ctt      795
Arg Asn His Ser Ser Gln Asn Phe Pro Gly Pro Ser Ala Arg Lys Leu
        205                 210                 215 ctc caa cca gag aat ccc tgc cca ggg gat cag aat cag gag cgg caa      843
Leu Gln Pro Glu Asn Pro Cys Pro Gly Asp Gln Asn Gln Glu Arg Gln
    220                 225                 230 tat tct gat cca cgc tgc tgt aat gac aaa acc aaa ggt caa gag atc      891
Tyr Ser Asp Pro Arg Cys Cys Asn Asp Lys Thr Lys Gly Gln Glu Ile
235                 240                 245                 250 aaa gaa agg tcc aaa ctc ttg aat aaa agg aca tgg cag agg gag att      939
Lys Glu Arg Ser Lys Leu Leu Asn Lys Arg Thr Trp Gln Arg Glu Ile
                255                 260                 265 tca agg gcc ttt tct agc cca ccc aaa gga caa atg ggg agc tct aga      987
Ser Arg Ala Phe Ser Ser Pro Pro Lys Gly Gln Met Gly Ser Ser Arg
            270                 275                 280 gtg gga gaa aga atg atg gaa gaa gag tcc aga aca ggc cag aaa gtg     1035
Val Gly Glu Arg Met Met Glu Glu Glu Ser Arg Thr Gly Gln Lys Val
        285                 290                 295 aat cca ggg aac aca ggc aaa tta ttt gtg ggg gta gga atc tca aga     1083
Asn Pro Gly Asn Thr Gly Lys Leu Phe Val Gly Val Gly Ile Ser Arg
    300                 305                 310 att gcg aaa gtc aaa tat gga gag tgt ggg caa ggt ttc agt gat aag     1131
Ile Ala Lys Val Lys Tyr Gly Glu Cys Gly Gln Gly Phe Ser Asp Lys
315                 320                 325                 330 tca gat gtt att aca cac caa agg aca cac aca ggg ggg aag ccc tac     1179
Ser Asp Val Ile Thr His Gln Arg Thr His Thr Gly Gly Lys Pro Tyr
                335                 340                 345 gtc tgc aga gag tgt ggg gag ggc ttt agc cgg aag tca gac ctc ctc     1227
Val Cys Arg Glu Cys Gly Glu Gly Phe Ser Arg Lys Ser Asp Leu Leu
            350                 355                 360 agt cac cag agg aca cac aca ggg gag aag cct tat gtc tgc aga gag     1275
Ser His Gln Arg Thr His Thr Gly Glu Lys Pro Tyr Val Cys Arg Glu
```

```
                    365                  370                  375
tgt gag cgg ggc ttt agc cgg aag tca gtc ctc ctc att cac cag agg    1323
Cys Glu Arg Gly Phe Ser Arg Lys Ser Val Leu Leu Ile His Gln Arg
    380                 385                 390 aca cac agg gga gaa gcc cca gtc tgc agg aag gat gag taa            1365
Thr His Arg Gly Glu Ala Pro Val Cys Arg Lys Asp Glu
395                 400                 405 gtcattagta ataaaacctt atctcaatag ccacaagaag acaaacgtga tcaccacaca  1425
ct                                                                 1427

<210> SEQ ID NO 14
<211> LENGTH: 407
<212> TYPE: PRT
<213> ORGANISM: Homo sapiens

<400> SEQUENCE: 14

Met Cys Gln Asn Phe Phe Ile Asp Ser Cys Ala Ala His Gly Pro Pro
 1               5                  10                  15

Thr Phe Val Lys Asp Ser Ala Val Asp Lys Gly His Pro Asn Arg Ser
                20                  25                  30

Ala Leu Ser Leu Pro Pro Gly Leu Arg Ile Gly Pro Ser Gly Ile Pro
            35                  40                  45

Gln Ala Gly Leu Gly Val Trp Asn Glu Ala Ser Asp Leu Pro Leu Gly
        50                  55                  60

Leu His Phe Gly Pro Tyr Glu Gly Arg Ile Thr Glu Asp Glu Glu Ala
 65                  70                  75                  80

Ala Asn Ser Gly Tyr Ser Trp Leu Ile Thr Lys Gly Arg Asn Cys Tyr
                85                  90                  95

Glu Tyr Val Asp Gly Lys Asp Lys Ser Ser Ala Asn Trp Met Arg Tyr
                100                 105                 110

Val Asn Cys Ala Arg Asp Asp Glu Glu Gln Asn Leu Val Ala Phe Gln
            115                 120                 125

Tyr His Arg Gln Ile Phe Tyr Arg Thr Cys Arg Val Ile Arg Pro Gly
        130                 135                 140

Cys Glu Leu Leu Val Trp Tyr Gly Asp Glu Tyr Gly Gln Glu Leu Gly
145                 150                 155                 160

Ile Lys Trp Gly Ser Lys Trp Lys Lys Glu Leu Met Ala Gly Arg Glu
                165                 170                 175

Pro Lys Pro Glu Ile His Pro Cys Pro Ser Cys Cys Leu Ala Phe Ser
            180                 185                 190

Ser Gln Lys Phe Leu Ser Gln His Val Glu Arg Asn His Ser Ser Gln
        195                 200                 205

Asn Phe Pro Gly Pro Ser Ala Arg Lys Leu Leu Gln Pro Glu Asn Pro
    210                 215                 220

Cys Pro Gly Asp Gln Asn Gln Glu Arg Gln Tyr Ser Asp Pro Arg Cys
225                 230                 235                 240

Cys Asn Asp Lys Thr Lys Gly Gln Glu Ile Lys Glu Arg Ser Lys Leu
                245                 250                 255

Leu Asn Lys Arg Thr Trp Gln Arg Glu Ile Ser Arg Ala Phe Ser Ser
            260                 265                 270

Pro Pro Lys Gly Gln Met Gly Ser Ser Arg Val Gly Glu Arg Met Met
        275                 280                 285

Glu Glu Glu Ser Arg Thr Gly Gln Lys Val Asn Pro Gly Asn Thr Gly
    290                 295                 300
```

| | | | | | | | | | | | | |
|---|---|---|---|---|---|---|---|---|---|---|---|---|
| Lys | Leu | Phe | Val | Gly | Val | Gly | Ile | Ser | Arg | Ile | Ala | Lys | Val | Lys | Tyr |
| 305 | | | | 310 | | | | 315 | | | | 320 |

| Gly | Glu | Cys | Gly | Gln | Gly | Phe | Ser | Asp | Lys | Ser | Asp | Val | Ile | Thr | His |
|---|---|---|---|---|---|---|---|---|---|---|---|---|---|---|---|
| | | | 325 | | | | | 330 | | | | | 335 | | |

| Gln | Arg | Thr | His | Thr | Gly | Gly | Lys | Pro | Tyr | Val | Cys | Arg | Glu | Cys | Gly |
|---|---|---|---|---|---|---|---|---|---|---|---|---|---|---|---|
| | | | 340 | | | | | 345 | | | | | 350 | | |

| Glu | Gly | Phe | Ser | Arg | Lys | Ser | Asp | Leu | Leu | Ser | His | Gln | Arg | Thr | His |
|---|---|---|---|---|---|---|---|---|---|---|---|---|---|---|---|
| | | | 355 | | | | | 360 | | | | | 365 | | |

| Thr | Gly | Glu | Lys | Pro | Tyr | Val | Cys | Arg | Glu | Cys | Glu | Arg | Gly | Phe | Ser |
|---|---|---|---|---|---|---|---|---|---|---|---|---|---|---|---|
| | 370 | | | | | 375 | | | | | 380 | | | | |

| Arg | Lys | Ser | Val | Leu | Leu | Ile | His | Gln | Arg | Thr | His | Arg | Gly | Glu | Ala |
|---|---|---|---|---|---|---|---|---|---|---|---|---|---|---|---|
| 385 | | | | | 390 | | | | | 395 | | | | | 400 |

| Pro | Val | Cys | Arg | Lys | Asp | Glu |
|---|---|---|---|---|---|---|
| | | | 405 | | | |

```
<210> SEQ ID NO 15
<211> LENGTH: 2506
<212> TYPE: DNA
<213> ORGANISM: Homo sapiens
<220> FEATURE:
<221> NAME/KEY: CDS
<222> LOCATION: (1234)..(2133)

<400> SEQUENCE: 15
```

| | |
|---|---|
| aaaagcagca tcagacaaga gctttattaa tcccttacac gagcaaatgc gatctctgac | 60 |
| ctactagact tgttttccta caatttcaca aaaagcctcg ctagaggaat gtgcaaggac | 120 |
| agaagggaaa ctgaggagag acccgcaact cattagcgaa ataatagggt gcacttcaat | 180 |
| aaaaatgcgg tcctgaagtg gagcagactc accggcaagg agcccggaaa atcgtcaggg | 240 |
| gcggcggcaa atactatca aatcagcctg gaagcatct tttcgctcag caagttcaag | 300 |
| agaacaaata tgttacaatc cttgcctatt cttgcctcca cttcataatg tcataaaagc | 360 |
| cacctggggt gtcatttatc aacctctctc cagcccactc ttccaaaata cactacagt | 420 |
| ttcctacatg tgtattttg ccaggactcc aaagagcctt gctaaagtgg aacaagcaaa | 480 |
| atcctcccct ggcctcctgg gactgcagtc accaggctgt caaagcctca atccccact | 540 |
| gagttccaga aagggtctc aaagctggga gaggatcaaa ctaacatgga gtagagaatt | 600 |
| gaactgtgaa aaagaagccc gagattcccc agcgacgtgg tgttgcagcc ccgttgaagg | 660 |
| agtcaacttg caggctgtta agacctcaa gtcattagca tcagctgctg cactaaaggg | 720 |
| gcaagtcagc gcctctaagt ggcttagcgc acaaacgagg ctcccgagac ggcctcggca | 780 |
| actccatccc ctcctccacc acccgctgga tgtgaaaagc tttccggagc ccatcttggg | 840 |
| ggaagcttgg tagtgttggc gctcctgaag agagacgacg cccgtttatc accccaggc | 900 |
| aactagctgc gcaaatcagc ggtggctcca gggctagaga atccctggag ctaaccgcac | 960 |
| ccctctccct ttcacggaac gcggactccg gggaaatacg cacggggtcc gcacgcgctg | 1020 |
| ggtgtccagc tctctgtcac agcttctcca agtgcctagt gaaacgggga aaggccctct | 1080 |
| ccaatcattt tggaagagcc taaaaggcgg caacaccaac acctcttgac atggaaatac | 1140 |
| actgatacaa taggcaaaag gaaacactcg attgcatctt cccggttcca ggtggcctta | 1200 |
| tttgggagat ctatactga ccttattcct gtg atg gag gat act ggc atc cag | 1254 |
|                                                  Met Glu Asp Thr Gly Ile Gln<br>                                                   1             5 | |
| cga ggc atc tgg gat gga gat gcc aag gct gtc caa caa tgt ctg aca | 1302 |
| Arg Gly Ile Trp Asp Gly Asp Ala Lys Ala Val Gln Gln Cys Leu Thr<br>    10                    15                    20 | |

| | | | | | | | | | | | | | | |
|---|---|---|---|---|---|---|---|---|---|---|---|---|---|---|
| gat | att | ttt | acc | agc | gtt | tac | acc | acc | tgc | gac | atc | cct | gag | aat | gct | 1350 |
| Asp | Ile | Phe | Thr | Ser | Val | Tyr | Thr | Thr | Cys | Asp | Ile | Pro | Glu | Asn | Ala |
| | 25 | | | | 30 | | | | 35 | | | | | | |

```
gat att ttt acc agc gtt tac acc acc tgc gac atc cct gag aat gct    1350
Asp Ile Phe Thr Ser Val Tyr Thr Thr Cys Asp Ile Pro Glu Asn Ala
     25                  30                  35 ata ttt ggt ccc tgt gtc ctg agc cat act tcc cta tat gac agc ata    1398
Ile Phe Gly Pro Cys Val Leu Ser His Thr Ser Leu Tyr Asp Ser Ile
 40                  45                  50                  55 gct ttc ata gct ctc aag tct act gac aag aga aca gta ccg tat atc    1446
Ala Phe Ile Ala Leu Lys Ser Thr Asp Lys Arg Thr Val Pro Tyr Ile
                 60                  65                  70 ttt cgg gta gac acc tca gca gca aat ggt tcc tca gaa ggt ctc atg    1494
Phe Arg Val Asp Thr Ser Ala Ala Asn Gly Ser Ser Glu Gly Leu Met
             75                  80                  85 tgg ctg cgg ttg gtc caa tcg gcc aga gat aag gaa gag cag aac ctt    1542
Trp Leu Arg Leu Val Gln Ser Ala Arg Asp Lys Glu Glu Gln Asn Leu
         90                  95                 100 gaa gcc tac ata aaa aac gga cag ctg ttc tac cgc tct ctc cgc agg    1590
Glu Ala Tyr Ile Lys Asn Gly Gln Leu Phe Tyr Arg Ser Leu Arg Arg
    105                 110                 115 att gcc aaa gac gag gag tta cta gtt tgg tac ggg aaa gaa ctg act    1638
Ile Ala Lys Asp Glu Glu Leu Leu Val Trp Tyr Gly Lys Glu Leu Thr
120                 125                 130                 135 gag tta ctc ttg ctt tgc ccc tct aga tcc cac aac aaa atg aat ggg    1686
Glu Leu Leu Leu Leu Cys Pro Ser Arg Ser His Asn Lys Met Asn Gly
                140                 145                 150 tcg tcc cct tac aca tgc ctg gaa tgc agc caa cgt ttc cag ttt gag    1734
Ser Ser Pro Tyr Thr Cys Leu Glu Cys Ser Gln Arg Phe Gln Phe Glu
            155                 160                 165 ttc ccc tat gtg gcg cat ctg cgt ttc cgc tgc ccc aag aga ctt cac    1782
Phe Pro Tyr Val Ala His Leu Arg Phe Arg Cys Pro Lys Arg Leu His
        170                 175                 180 agc gct gat ata agt ccc caa gac gaa caa ggc ggc ggc gtg ggc acc    1830
Ser Ala Asp Ile Ser Pro Gln Asp Glu Gln Gly Gly Gly Val Gly Thr
    185                 190                 195 aag gac cac ggg ggc ggc ggc ggc ggt ggc aaa gac cag cag cag cag    1878
Lys Asp His Gly Gly Gly Gly Gly Gly Lys Asp Gln Gln Gln Gln
200                 205                 210                 215 cag cag gag gca cct tta ggc ccg ggt ccc aag ttt tgc aaa gcc ggc    1926
Gln Gln Glu Ala Pro Leu Gly Pro Gly Pro Lys Phe Cys Lys Ala Gly
                220                 225                 230 ccc ctc cac cac tac cca tcc ccc tcc ccg gaa agc agc aac cca tcc    1974
Pro Leu His His Tyr Pro Ser Pro Ser Pro Glu Ser Ser Asn Pro Ser
            235                 240                 245 gct gcc gcc ggc ggc agc agc gcg aag cca tcc aca gac ttc cac aac    2022
Ala Ala Ala Gly Gly Ser Ser Ala Lys Pro Ser Thr Asp Phe His Asn
        250                 255                 260 ctg gcc agg gag ctg gaa aac tcc cgg gga ggc agc agc tgc tcc cca    2070
Leu Ala Arg Glu Leu Glu Asn Ser Arg Gly Gly Ser Ser Cys Ser Pro
    265                 270                 275 gcc cag agc ctc agc agc ggt agg gca gcg gcg gcg gcg gcc acc        2118
Ala Gln Ser Leu Ser Ser Gly Arg Ala Ala Ala Ala Ala Ala Thr
280                 285                 290                 295 agg agg cgg agc tga gtcccgacgg catcgccacg ggcggcggca aaggaaagag    2173
Arg Arg Arg Ser
                300 gaaattcccg gaggaggcgg cggaggccgg cggtggcgct ggtttggtag gggccgcgtt    2233 gtaacggccc ctcccggcct ccaaggagga tctggtgtgc acaccgcagc agtaccgagc    2293 ctcgggcagc tacttcggcc tggaagagaa cggccgcctc ttcgcgccgc caagtcccga    2353
```

```
gacgggcgag gcgaagcgca gcgccttcgt ggaggtgaag aaggctgccc gcgcggccag    2413
cctgcaggag gagggacag ccgacggcgc gggagtcgcc tccgaggacc aggacgctgg    2473
cggcggcggc ggctcctcca cgcccgcggc cgc                                 2506
```

<210> SEQ ID NO 16
<211> LENGTH: 299
<212> TYPE: PRT
<213> ORGANISM: Homo sapiens

<400> SEQUENCE: 16

```
Met Glu Asp Thr Gly Ile Gln Arg Gly Ile Trp Asp Gly Asp Ala Lys
 1               5                  10                  15

Ala Val Gln Gln Cys Leu Thr Asp Ile Phe Thr Ser Val Tyr Thr Thr
                20                  25                  30

Cys Asp Ile Pro Glu Asn Ala Ile Phe Gly Pro Cys Val Leu Ser His
            35                  40                  45

Thr Ser Leu Tyr Asp Ser Ile Ala Phe Ile Ala Leu Lys Ser Thr Asp
        50                  55                  60

Lys Arg Thr Val Pro Tyr Ile Phe Arg Val Asp Thr Ser Ala Ala Asn
 65                  70                  75                  80

Gly Ser Ser Glu Gly Leu Met Trp Leu Arg Leu Val Gln Ser Ala Arg
                85                  90                  95

Asp Lys Glu Glu Gln Asn Leu Glu Ala Tyr Ile Lys Asn Gly Gln Leu
                100                 105                 110

Phe Tyr Arg Ser Leu Arg Arg Ile Ala Lys Asp Glu Glu Leu Leu Val
            115                 120                 125

Trp Tyr Gly Lys Glu Leu Thr Glu Leu Leu Leu Cys Pro Ser Arg
        130                 135                 140

Ser His Asn Lys Met Asn Gly Ser Ser Pro Tyr Thr Cys Leu Glu Cys
145                 150                 155                 160

Ser Gln Arg Phe Gln Phe Glu Phe Pro Tyr Val Ala His Leu Arg Phe
                165                 170                 175

Arg Cys Pro Lys Arg Leu His Ser Ala Asp Ile Ser Pro Gln Asp Glu
            180                 185                 190

Gln Gly Gly Gly Val Gly Thr Lys Asp His Gly Gly Gly Gly Gly
        195                 200                 205

Gly Lys Asp Gln Gln Gln Gln Gln Glu Ala Pro Leu Gly Pro Gly
    210                 215                 220

Pro Lys Phe Cys Lys Ala Gly Pro Leu His His Tyr Pro Ser Pro Ser
225                 230                 235                 240

Pro Glu Ser Ser Asn Pro Ser Ala Ala Ala Gly Gly Ser Ser Ala Lys
                245                 250                 255

Pro Ser Thr Asp Phe His Asn Leu Ala Arg Glu Leu Glu Asn Ser Arg
            260                 265                 270

Gly Gly Ser Ser Cys Ser Pro Ala Gln Ser Leu Ser Ser Gly Arg Ala
        275                 280                 285

Ala Ala Ala Ala Ala Thr Arg Arg Arg Ser
    290                 295
```

<210> SEQ ID NO 17
<211> LENGTH: 369
<212> TYPE: DNA
<213> ORGANISM: Homo sapiens
<220> FEATURE:
<221> NAME/KEY: CDS
<222> LOCATION: (1)..(369)

<400> SEQUENCE: 17

| cgt | cag | tca | att | gtg | gga | gca | gaa | gtt | ggt | gta | tgg | act | gga | gaa | acc | 48 |
| Arg | Gln | Ser | Ile | Val | Gly | Ala | Glu | Val | Gly | Val | Trp | Thr | Gly | Glu | Thr | |
| 1 | | | | 5 | | | | | 10 | | | | | 15 | | |

| att | cct | gtg | cgg | act | tgc | ttt | gga | cct | cta | att | ggc | cag | cag | agt | cac | 96 |
| Ile | Pro | Val | Arg | Thr | Cys | Phe | Gly | Pro | Leu | Ile | Gly | Gln | Gln | Ser | His | |
| | | | 20 | | | | | 25 | | | | | 30 | | | |

| tcc | atg | gaa | gta | gca | gaa | tgg | aca | gac | aag | gca | gtt | aac | cat | atc | tgg | 144 |
| Ser | Met | Glu | Val | Ala | Glu | Trp | Thr | Asp | Lys | Ala | Val | Asn | His | Ile | Trp | |
| | 35 | | | | | 40 | | | | | 45 | | | | | |

| aag | ata | tac | cac | aat | ggt | gtc | cta | gaa | ttc | tgc | atc | att | aca | act | gat | 192 |
| Lys | Ile | Tyr | His | Asn | Gly | Val | Leu | Glu | Phe | Cys | Ile | Ile | Thr | Thr | Asp | |
| 50 | | | | | 55 | | | | | 60 | | | | | | |

| gaa | aat | gaa | tgt | aat | tgg | atg | atg | ttt | gtg | cgc | aaa | gcc | agg | aac | cgg | 240 |
| Glu | Asn | Glu | Cys | Asn | Trp | Met | Met | Phe | Val | Arg | Lys | Ala | Arg | Asn | Arg | |
| 65 | | | | | 70 | | | | 75 | | | | | 80 | | |

| gaa | gag | cag | aat | ttg | gtg | gct | tat | cct | cat | gat | gga | aaa | atc | ttt | ttc | 288 |
| Glu | Glu | Gln | Asn | Leu | Val | Ala | Tyr | Pro | His | Asp | Gly | Lys | Ile | Phe | Phe | |
| | | | | 85 | | | | | 90 | | | | | 95 | | |

| tgc | acc | tca | caa | gat | atc | cct | cct | gaa | aat | gaa | ctg | ctt | ttt | tat | tat | 336 |
| Cys | Thr | Ser | Gln | Asp | Ile | Pro | Pro | Glu | Asn | Glu | Leu | Leu | Phe | Tyr | Tyr | |
| | | | 100 | | | | | 105 | | | | | 110 | | | |

| agc | cga | gat | tat | gct | caa | cag | att | ggt | gtt | cct | | | | | | 369 |
| Ser | Arg | Asp | Tyr | Ala | Gln | Gln | Ile | Gly | Val | Pro | | | | | | |
| | | | 115 | | | | | 120 | | | | | | | | |

<210> SEQ ID NO 18
<211> LENGTH: 123
<212> TYPE: PRT
<213> ORGANISM: Homo sapiens

<400> SEQUENCE: 18

Arg Gln Ser Ile Val Gly Ala Glu Val Gly Val Trp Thr Gly Glu Thr
1               5                   10                  15

Ile Pro Val Arg Thr Cys Phe Gly Pro Leu Ile Gly Gln Gln Ser His
            20                  25                  30

Ser Met Glu Val Ala Glu Trp Thr Asp Lys Ala Val Asn His Ile Trp
        35                  40                  45

Lys Ile Tyr His Asn Gly Val Leu Glu Phe Cys Ile Ile Thr Thr Asp
    50                  55                  60

Glu Asn Glu Cys Asn Trp Met Met Phe Val Arg Lys Ala Arg Asn Arg
65                  70                  75                  80

Glu Glu Gln Asn Leu Val Ala Tyr Pro His Asp Gly Lys Ile Phe Phe
                85                  90                  95

Cys Thr Ser Gln Asp Ile Pro Pro Glu Asn Glu Leu Leu Phe Tyr Tyr
            100                 105                 110

Ser Arg Asp Tyr Ala Gln Gln Ile Gly Val Pro
        115                 120

<210> SEQ ID NO 19
<211> LENGTH: 231
<212> TYPE: DNA
<213> ORGANISM: Homo sapiens
<220> FEATURE:
<221> NAME/KEY: CDS
<222> LOCATION: (1)..(231)

<400> SEQUENCE: 19 atg gat tac agg ttg atg tgg gag gtt cgt ggg agt aag gga gaa gtt     48

```
Met Asp Tyr Arg Leu Met Trp Glu Val Arg Gly Ser Lys Gly Glu Val
 1               5                  10                  15 ttg tac att ttg gat gct acc aac cca cgg cac tcc aac tgg ctt cgc      96
Leu Tyr Ile Leu Asp Ala Thr Asn Pro Arg His Ser Asn Trp Leu Arg
             20                  25                  30 ttc gtt cat gag gca cca tct cag gag cag aag aac ttg gct gcc att     144
Phe Val His Glu Ala Pro Ser Gln Glu Gln Lys Asn Leu Ala Ala Ile
         35                  40                  45 caa gaa gga gaa aac att ttc tat ttg gca gtt gaa gat ata gaa aca     192
Gln Glu Gly Glu Asn Ile Phe Tyr Leu Ala Val Glu Asp Ile Glu Thr
     50                  55                  60 gac acg gag ctt ctg att ggc tac ctg gat agt gac atg                 231
Asp Thr Glu Leu Leu Ile Gly Tyr Leu Asp Ser Asp Met
 65                  70                  75

<210> SEQ ID NO 20
<211> LENGTH: 77
<212> TYPE: PRT
<213> ORGANISM: Homo sapiens

<400> SEQUENCE: 20

Met Asp Tyr Arg Leu Met Trp Glu Val Arg Gly Ser Lys Gly Glu Val
 1               5                  10                  15

Leu Tyr Ile Leu Asp Ala Thr Asn Pro Arg His Ser Asn Trp Leu Arg
             20                  25                  30

Phe Val His Glu Ala Pro Ser Gln Glu Gln Lys Asn Leu Ala Ala Ile
         35                  40                  45

Gln Glu Gly Glu Asn Ile Phe Tyr Leu Ala Val Glu Asp Ile Glu Thr
     50                  55                  60

Asp Thr Glu Leu Leu Ile Gly Tyr Leu Asp Ser Asp Met
 65                  70                  75

<210> SEQ ID NO 21
<211> LENGTH: 354
<212> TYPE: DNA
<213> ORGANISM: Mus musculus
<220> FEATURE:
<221> NAME/KEY: CDS
<222> LOCATION: (1)..(354)

<400> SEQUENCE: 21 tcg tcc cgg gtc cag gac ggg atg ggg ctc tac acg gcc cgc cgc gtg      48
Ser Ser Arg Val Gln Asp Gly Met Gly Leu Tyr Thr Ala Arg Arg Val
 1               5                  10                  15 cgc aag ggt gaa aaa ttt gga ccc ttc gct ggg gag aag cga atg cct      96
Arg Lys Gly Glu Lys Phe Gly Pro Phe Ala Gly Glu Lys Arg Met Pro
             20                  25                  30 gaa gac ttg gat gaa aat atg gac tac aga ctg atg tgg gtg gta cgt     144
Glu Asp Leu Asp Glu Asn Met Asp Tyr Arg Leu Met Trp Val Val Arg
         35                  40                  45 ggg agc aag gga gaa gtt ctg tat att ttg gat gct acc aac cca aga     192
Gly Ser Lys Gly Glu Val Leu Tyr Ile Leu Asp Ala Thr Asn Pro Arg
     50                  55                  60 cac tcc aac tgg ctt cgc ttt gtt cac gag gca cca tct cag gag cgg     240
His Ser Asn Trp Leu Arg Phe Val His Glu Ala Pro Ser Gln Glu Arg
 65                  70                  75                  80 aag aac ctg gct gcc att caa gaa gga gaa aaa tat ttc tac ttg gca     288
Lys Asn Leu Ala Ala Ile Gln Glu Gly Glu Lys Tyr Phe Tyr Leu Ala
             85                  90                  95 gtt gat gat ata gaa aca gat aca gag ctt ttg att ggc tac ctg gac     336
Val Asp Asp Ile Glu Thr Asp Thr Glu Leu Leu Ile Gly Tyr Leu Asp
```

```
                100               105               110
agt gat gtg gag gca gag                                              354
Ser Asp Val Glu Ala Glu
        115

<210> SEQ ID NO 22
<211> LENGTH: 118
<212> TYPE: PRT
<213> ORGANISM: Mus musculus

<400> SEQUENCE: 22

Ser Ser Arg Val Gln Asp Gly Met Gly Leu Tyr Thr Ala Arg Arg Val
  1               5                  10                  15

Arg Lys Gly Glu Lys Phe Gly Pro Phe Ala Gly Glu Lys Arg Met Pro
                 20                  25                  30

Glu Asp Leu Asp Glu Asn Met Asp Tyr Arg Leu Met Trp Val Val Arg
             35                  40                  45

Gly Ser Lys Gly Glu Val Leu Tyr Ile Leu Asp Ala Thr Asn Pro Arg
         50                  55                  60

His Ser Asn Trp Leu Arg Phe Val His Glu Ala Pro Ser Gln Glu Arg
 65                  70                  75                  80

Lys Asn Leu Ala Ala Ile Gln Glu Gly Glu Lys Tyr Phe Tyr Leu Ala
                 85                  90                  95

Val Asp Asp Ile Glu Thr Asp Thr Glu Leu Leu Ile Gly Tyr Leu Asp
                100                 105                 110

Ser Asp Val Glu Ala Glu
        115

<210> SEQ ID NO 23
<211> LENGTH: 369
<212> TYPE: DNA
<213> ORGANISM: Homo sapiens
<220> FEATURE:
<221> NAME/KEY: CDS
<222> LOCATION: (1)..(369)

<400> SEQUENCE: 23 acc agt act gtg ccc ggc ctg gcc tac ggc atc tgc gcg gcg cag agg      48
Thr Ser Thr Val Pro Gly Leu Ala Tyr Gly Ile Cys Ala Ala Gln Arg
  1               5                  10                  15 atc cag caa ggc acc tgg att gga cct ttc caa ggc gtg ctt ctg ccc      96
Ile Gln Gln Gly Thr Trp Ile Gly Pro Phe Gln Gly Val Leu Leu Pro
                 20                  25                  30 cca gag aag gtg cag gca ggc gcc gtg agg aac acg cag cat ctc tgg     144
Pro Glu Lys Val Gln Ala Gly Ala Val Arg Asn Thr Gln His Leu Trp
             35                  40                  45 gag ata tat gac cag gat ggg aca cta cag cac ttt att gat ggt ggg     192
Glu Ile Tyr Asp Gln Asp Gly Thr Leu Gln His Phe Ile Asp Gly Gly
         50                  55                  60 gaa cct agt aag tcg agc tgg atg agg tat atc cga tgt gca agg cac     240
Glu Pro Ser Lys Ser Ser Trp Met Arg Tyr Ile Arg Cys Ala Arg His
 65                  70                  75                  80 tgc gga gaa cag aat cta aca gta gtt cag tac agg tcg aat ata ttc     288
Cys Gly Glu Gln Asn Leu Thr Val Val Gln Tyr Arg Ser Asn Ile Phe
                 85                  90                  95 tac cga gcc tgt ata gat atc cct agg ggc acc gag ctt ctg gtg tgg     336
Tyr Arg Ala Cys Ile Asp Ile Pro Arg Gly Thr Glu Leu Leu Val Trp
                100                 105                 110 tac aat gac agc tat acg tct ttc ttt ggg atc                         369
Tyr Asn Asp Ser Tyr Thr Ser Phe Phe Gly Ile
```

<210> SEQ ID NO 24
<211> LENGTH: 123
<212> TYPE: PRT
<213> ORGANISM: Homo sapiens

<400> SEQUENCE: 24

Thr Ser Thr Val Pro Gly Leu Ala Tyr Gly Ile Cys Ala Ala Gln Arg
1               5                   10                  15

Ile Gln Gln Gly Thr Trp Ile Gly Pro Phe Gln Gly Val Leu Leu Pro
            20                  25                  30

Pro Glu Lys Val Gln Ala Gly Ala Val Arg Asn Thr Gln His Leu Trp
        35                  40                  45

Glu Ile Tyr Asp Gln Asp Gly Thr Leu Gln His Phe Ile Asp Gly Gly
    50                  55                  60

Glu Pro Ser Lys Ser Ser Trp Met Arg Tyr Ile Arg Cys Ala Arg His
65                  70                  75                  80

Cys Gly Glu Gln Asn Leu Thr Val Val Gln Tyr Arg Ser Asn Ile Phe
                85                  90                  95

Tyr Arg Ala Cys Ile Asp Ile Pro Arg Gly Thr Glu Leu Leu Val Trp
            100                 105                 110

Tyr Asn Asp Ser Tyr Thr Ser Phe Phe Gly Ile
        115                 120

<210> SEQ ID NO 25
<211> LENGTH: 342
<212> TYPE: DNA
<213> ORGANISM: Homo sapiens
<220> FEATURE:
<221> NAME/KEY: CDS
<222> LOCATION: (1)..(342)

<400> SEQUENCE: 25 ggc atc cct cag gct ggg ctt gga gta tgg aac gag gca tct gat ctg        48
Gly Ile Pro Gln Ala Gly Leu Gly Val Trp Asn Glu Ala Ser Asp Leu
1               5                   10                  15 cca ctg ggt ctg cac ttt ggc ccc tat gag ggc cga att aca gaa gac        96
Pro Leu Gly Leu His Phe Gly Pro Tyr Glu Gly Arg Ile Thr Glu Asp
            20                  25                  30 gaa gag gca gcc aac agt gga tat tcc tgg cta atc acc aag ggg aga       144
Glu Glu Ala Ala Asn Ser Gly Tyr Ser Trp Leu Ile Thr Lys Gly Arg
        35                  40                  45 aac tgc tat gag tat gtg gat gga aaa gat aaa tcc tcg gcc aac tgg       192
Asn Cys Tyr Glu Tyr Val Asp Gly Lys Asp Lys Ser Ser Ala Asn Trp
    50                  55                  60 atg agg tat gtg aac tgt gcc cgg gat gat gaa gag cag aac ctg gtg       240
Met Arg Tyr Val Asn Cys Ala Arg Asp Asp Glu Glu Gln Asn Leu Val
65                  70                  75                  80 gcc ttc cag tac cac agg cag atc ttc tat aga acc tgc cga gtc att       288
Ala Phe Gln Tyr His Arg Gln Ile Phe Tyr Arg Thr Cys Arg Val Ile
                85                  90                  95 agg cca ggc tgt gaa ctg ctg gtc tgg tat ggg gat gag tat ggc cag       336
Arg Pro Gly Cys Glu Leu Leu Val Trp Tyr Gly Asp Glu Tyr Gly Gln
            100                 105                 110 gaa ctg                                                                342
Glu Leu

<210> SEQ ID NO 26
<211> LENGTH: 114

<212> TYPE: PRT
<213> ORGANISM: Homo sapiens

<400> SEQUENCE: 26

```
Gly Ile Pro Gln Ala Gly Leu Gly Val Trp Asn Glu Ala Ser Asp Leu
 1               5                  10                  15

Pro Leu Gly Leu His Phe Gly Pro Tyr Glu Gly Arg Ile Thr Glu Asp
                20                  25                  30

Glu Glu Ala Ala Asn Ser Gly Tyr Ser Trp Leu Ile Thr Lys Gly Arg
            35                  40                  45

Asn Cys Tyr Glu Tyr Val Asp Gly Lys Asp Lys Ser Ser Ala Asn Trp
        50                  55                  60

Met Arg Tyr Val Asn Cys Ala Arg Asp Asp Glu Glu Gln Asn Leu Val
 65                  70                  75                  80

Ala Phe Gln Tyr His Arg Gln Ile Phe Tyr Arg Thr Cys Arg Val Ile
                85                  90                  95

Arg Pro Gly Cys Glu Leu Leu Val Trp Tyr Gly Asp Glu Tyr Gly Gln
               100                 105                 110

Glu Leu
```

<210> SEQ ID NO 27
<211> LENGTH: 342
<212> TYPE: DNA
<213> ORGANISM: Homo sapiens
<220> FEATURE:
<221> NAME/KEY: CDS
<222> LOCATION: (1)..(342)

<400> SEQUENCE: 27

```
att ttt acc agc gtt tac acc acc tgc gac atc cct gag aat gct ata      48
Ile Phe Thr Ser Val Tyr Thr Thr Cys Asp Ile Pro Glu Asn Ala Ile
 1               5                  10                  15 ttt ggt ccc tgt gtc ctg agc cat act tcc cta tat gac agc ata gct      96
Phe Gly Pro Cys Val Leu Ser His Thr Ser Leu Tyr Asp Ser Ile Ala
                20                  25                  30 ttc ata gct ctc aag tct act gac aag aga aca gta ccg tat atc ttt     144
Phe Ile Ala Leu Lys Ser Thr Asp Lys Arg Thr Val Pro Tyr Ile Phe
            35                  40                  45 cgg gta gac acc tca gca gca aat ggt tcc tca gaa ggt ctc atg tgg     192
Arg Val Asp Thr Ser Ala Ala Asn Gly Ser Ser Glu Gly Leu Met Trp
        50                  55                  60 ctg cgg ttg gtc caa tcg gcc aga gat aag gaa gag cag aac ctt gaa     240
Leu Arg Leu Val Gln Ser Ala Arg Asp Lys Glu Glu Gln Asn Leu Glu
 65                  70                  75                  80 gcc tac ata aaa aac gga cag ctg ttc tac cgc tct ctc cgc agg att     288
Ala Tyr Ile Lys Asn Gly Gln Leu Phe Tyr Arg Ser Leu Arg Arg Ile
                85                  90                  95 gcc aaa gac gag gag tta cta gtt tgg tac ggg aaa gaa ctg act gag     336
Ala Lys Asp Glu Glu Leu Leu Val Trp Tyr Gly Lys Glu Leu Thr Glu
               100                 105                 110 tta ctc                                                              342
Leu Leu
```

<210> SEQ ID NO 28
<211> LENGTH: 114
<212> TYPE: PRT
<213> ORGANISM: Homo sapiens

<400> SEQUENCE: 28

Ile Phe Thr Ser Val Tyr Thr Thr Cys Asp Ile Pro Glu Asn Ala Ile

```
                1               5              10              15
Phe Gly Pro Cys Val Leu Ser His Thr Ser Leu Tyr Asp Ser Ile Ala
               20                      25                      30

Phe Ile Ala Leu Lys Ser Thr Asp Lys Arg Thr Val Pro Tyr Ile Phe
           35                      40                      45

Arg Val Asp Thr Ser Ala Ala Asn Gly Ser Ser Glu Gly Leu Met Trp
       50                      55                      60

Leu Arg Leu Val Gln Ser Ala Arg Asp Lys Glu Gln Asn Leu Glu
 65                      70                      75              80

Ala Tyr Ile Lys Asn Gly Gln Leu Phe Tyr Arg Ser Leu Arg Arg Ile
               85                      90                      95

Ala Lys Asp Glu Glu Leu Leu Val Trp Tyr Gly Lys Gly Leu Thr Glu
              100                     105                     110

Leu Leu
```

<210> SEQ ID NO 29
<211> LENGTH: 36
<212> TYPE: DNA
<213> ORGANISM: Homo sapiens
<220> FEATURE:
<221> NAME/KEY: CDS
<222> LOCATION: (1)..(36)

<400> SEQUENCE: 29

```
att cct gtg cgg act tgc ttt gga cct cta att ggc                    36
Ile Pro Val Arg Thr Cys Phe Gly Pro Leu Ile Gly
 1               5                  10
```

<210> SEQ ID NO 30
<211> LENGTH: 12
<212> TYPE: PRT
<213> ORGANISM: Homo sapiens

<400> SEQUENCE: 30

```
Ile Pro Val Arg Thr Cys Phe Gly Pro Leu Ile Gly
 1               5                  10
```

<210> SEQ ID NO 31
<211> LENGTH: 36
<212> TYPE: DNA
<213> ORGANISM: Homo sapiens
<220> FEATURE:
<221> NAME/KEY: CDS
<222> LOCATION: (1)..(36)

<400> SEQUENCE: 31

```
atc att aca act gat gaa aat gaa tgt aat tgg atg                    36
Ile Ile Thr Thr Asp Glu Asn Glu Cys Asn Trp Met
 1               5                  10
```

<210> SEQ ID NO 32
<211> LENGTH: 12
<212> TYPE: PRT
<213> ORGANISM: Homo sapiens

<400> SEQUENCE: 32

```
Ile Ile Thr Thr Asp Glu Asn Glu Cys Asn Trp Met
 1               5                  10
```

<210> SEQ ID NO 33
<211> LENGTH: 18
<212> TYPE: DNA
<213> ORGANISM: Homo sapiens

```
<220> FEATURE:
<221> NAME/KEY: CDS
<222> LOCATION: (1)..(18)

<400> SEQUENCE: 33 gaa ctg ctt ttt tat tat                                                  18
Glu Leu Leu Phe Tyr Tyr
 1               5

<210> SEQ ID NO 34
<211> LENGTH: 6
<212> TYPE: PRT
<213> ORGANISM: Homo sapiens

<400> SEQUENCE: 34

Glu Leu Leu Phe Tyr Tyr
 1               5

<210> SEQ ID NO 35
<211> LENGTH: 45
<212> TYPE: DNA
<213> ORGANISM: Homo sapiens
<220> FEATURE:
<221> NAME/KEY: CDS
<222> LOCATION: (1)..(45)

<400> SEQUENCE: 35 ttg tac att ttg gat gct acc aac cca cgg cac tcc aac tgg ctt              45
Leu Tyr Ile Leu Asp Ala Thr Asn Pro Arg His Ser Asn Trp Leu
 1               5                  10                  15

<210> SEQ ID NO 36
<211> LENGTH: 15
<212> TYPE: PRT
<213> ORGANISM: Homo sapiens

<400> SEQUENCE: 36

Leu Tyr Ile Leu Asp Ala Thr Asn Pro Arg His Ser Asn Trp Leu
 1               5                  10                  15

<210> SEQ ID NO 37
<211> LENGTH: 18
<212> TYPE: DNA
<213> ORGANISM: Homo sapiens
<220> FEATURE:
<221> NAME/KEY: CDS
<222> LOCATION: (1)..(18)

<400> SEQUENCE: 37 gag ctt ctg att ggc tac                                                  18
Glu Leu Leu Ile Gly Tyr
 1               5

<210> SEQ ID NO 38
<211> LENGTH: 6
<212> TYPE: PRT
<213> ORGANISM: Homo sapiens

<400> SEQUENCE: 38

Glu Leu Leu Ile Gly Tyr
 1               5

<210> SEQ ID NO 39
<211> LENGTH: 36
<212> TYPE: DNA
<213> ORGANISM: Mus musculus
<220> FEATURE:
```

```
<221> NAME/KEY: CDS
<222> LOCATION: (1)..(36)

<400> SEQUENCE: 39 gtg cgc aag ggt gaa aaa ttt gga ccc ttc gct ggg                    36
Val Arg Lys Gly Glu Lys Phe Gly Pro Phe Ala Gly
 1               5                  10

<210> SEQ ID NO 40
<211> LENGTH: 12
<212> TYPE: PRT
<213> ORGANISM: Mus musculus

<400> SEQUENCE: 40

Val Arg Lys Gly Glu Lys Phe Gly Pro Phe Ala Gly
 1               5                  10

<210> SEQ ID NO 41
<211> LENGTH: 36
<212> TYPE: DNA
<213> ORGANISM: Mus musculus
<220> FEATURE:
<221> NAME/KEY: CDS
<222> LOCATION: (1)..(36)

<400> SEQUENCE: 41 ttg gat gct acc aac cca aga cac tcc aac tgg ctt                    36
Leu Asp Ala Thr Asn Pro Arg His Ser Asn Trp Leu
 1               5                  10

<210> SEQ ID NO 42
<211> LENGTH: 12
<212> TYPE: PRT
<213> ORGANISM: Mus musculus

<400> SEQUENCE: 42

Leu Asp Ala Thr Asn Pro Arg His Ser Asn Trp Leu
 1               5                  10

<210> SEQ ID NO 43
<211> LENGTH: 18
<212> TYPE: DNA
<213> ORGANISM: Mus musculus
<220> FEATURE:
<221> NAME/KEY: CDS
<222> LOCATION: (1)..(18)

<400> SEQUENCE: 43 gag ctt ttg att ggc tac                                            18
Glu Leu Leu Ile Gly Tyr
 1               5

<210> SEQ ID NO 44
<211> LENGTH: 6
<212> TYPE: PRT
<213> ORGANISM: Mus musculus

<400> SEQUENCE: 44

Glu Leu Leu Ile Gly Tyr
 1               5

<210> SEQ ID NO 45
<211> LENGTH: 36
<212> TYPE: DNA
<213> ORGANISM: Homo sapiens
<220> FEATURE:
<221> NAME/KEY: CDS
```

```
<222> LOCATION: (1)..(36)

<400> SEQUENCE: 45 atc cag caa ggc acc tgg att gga cct ttc caa ggc                    36
Ile Gln Gln Gly Thr Trp Ile Gly Pro Phe Gln Gly
  1               5                  10

<210> SEQ ID NO 46
<211> LENGTH: 12
<212> TYPE: PRT
<213> ORGANISM: Homo sapiens

<400> SEQUENCE: 46

Ile Gln Gln Gly Thr Trp Ile Gly Pro Phe Gln Gly
  1               5                  10

<210> SEQ ID NO 47
<211> LENGTH: 36
<212> TYPE: DNA
<213> ORGANISM: Homo sapiens
<220> FEATURE:
<221> NAME/KEY: CDS
<222> LOCATION: (1)..(36)

<400> SEQUENCE: 47 att gat ggt ggg gaa cct agt aag tcg agc tgg atg                    36
Ile Asp Gly Gly Glu Pro Ser Lys Ser Ser Trp Met
  1               5                  10

<210> SEQ ID NO 48
<211> LENGTH: 12
<212> TYPE: PRT
<213> ORGANISM: Homo sapiens

<400> SEQUENCE: 48

Ile Asp Gly Gly Glu Pro Ser Lys Ser Ser Trp Met
  1               5                  10

<210> SEQ ID NO 49
<211> LENGTH: 18
<212> TYPE: DNA
<213> ORGANISM: Homo sapiens
<220> FEATURE:
<221> NAME/KEY: CDS
<222> LOCATION: (1)..(18)

<400> SEQUENCE: 49 gag ctt ctg gtg tgg tac                                            18
Glu Leu Leu Val Trp Tyr
  1               5

<210> SEQ ID NO 50
<211> LENGTH: 6
<212> TYPE: PRT
<213> ORGANISM: Homo sapiens

<400> SEQUENCE: 50

Glu Leu Leu Val Trp Tyr
  1               5

<210> SEQ ID NO 51
<211> LENGTH: 36
<212> TYPE: DNA
<213> ORGANISM: Homo sapiens
<220> FEATURE:
<221> NAME/KEY: CDS
<222> LOCATION: (1)..(36)
```

```
<400> SEQUENCE: 51 ctg cca ctg ggt ctg cac ttt ggc ccc tat gag ggc                    36
Leu Pro Leu Gly Leu His Phe Gly Pro Tyr Glu Gly
 1               5                  10

<210> SEQ ID NO 52
<211> LENGTH: 12
<212> TYPE: PRT
<213> ORGANISM: Homo sapiens

<400> SEQUENCE: 52

Leu Pro Leu Gly Leu His Phe Gly Pro Tyr Glu Gly
 1               5                  10

<210> SEQ ID NO 53
<211> LENGTH: 36
<212> TYPE: DNA
<213> ORGANISM: Homo sapiens
<220> FEATURE:
<221> NAME/KEY: CDS
<222> LOCATION: (1)..(36)

<400> SEQUENCE: 53 gtg gat gga aaa gat aaa tcc tcg gcc aac tgg atg                    36
Val Asp Gly Lys Asp Lys Ser Ser Ala Asn Trp Met
 1               5                  10

<210> SEQ ID NO 54
<211> LENGTH: 12
<212> TYPE: PRT
<213> ORGANISM: Homo sapiens

<400> SEQUENCE: 54

Val Asp Gly Lys Asp Lys Ser Ser Ala Asn Trp Met
 1               5                  10

<210> SEQ ID NO 55
<211> LENGTH: 18
<212> TYPE: DNA
<213> ORGANISM: Homo sapiens
<220> FEATURE:
<221> NAME/KEY: CDS
<222> LOCATION: (1)..(18)

<400> SEQUENCE: 55 gaa ctg ctg gtc tgg tat                                            18
Glu Leu Leu Val Trp Tyr
 1               5

<210> SEQ ID NO 56
<211> LENGTH: 6
<212> TYPE: PRT
<213> ORGANISM: Homo sapiens

<400> SEQUENCE: 56

Glu Leu Leu Val Trp Tyr
 1               5

<210> SEQ ID NO 57
<211> LENGTH: 33
<212> TYPE: DNA
<213> ORGANISM: Homo sapiens
<220> FEATURE:
<221> NAME/KEY: CDS
<222> LOCATION: (1)..(33)
```

```
<400> SEQUENCE: 57 atc cct gag aat gct ata ttt ggt ccc tgt gtc                    33
Ile Pro Glu Asn Ala Ile Phe Gly Pro Cys Val
 1               5                  10

<210> SEQ ID NO 58
<211> LENGTH: 11
<212> TYPE: PRT
<213> ORGANISM: Homo sapiens

<400> SEQUENCE: 58

Ile Pro Glu Asn Ala Ile Phe Gly Pro Cys Val
 1               5                  10

<210> SEQ ID NO 59
<211> LENGTH: 48
<212> TYPE: DNA
<213> ORGANISM: Homo sapiens
<220> FEATURE:
<221> NAME/KEY: CDS
<222> LOCATION: (1)..(48)

<400> SEQUENCE: 59 gta gac acc tca gca gca aat ggt tcc tca gaa ggt ctc atg tgg ctg    48
Val Asp Thr Ser Ala Ala Asn Gly Ser Ser Glu Gly Leu Met Trp Leu
 1               5                  10                  15

<210> SEQ ID NO 60
<211> LENGTH: 16
<212> TYPE: PRT
<213> ORGANISM: Homo sapiens

<400> SEQUENCE: 60

Val Asp Thr Ser Ala Ala Asn Gly Ser Ser Glu Gly Leu Met Trp Leu
 1               5                  10                  15

<210> SEQ ID NO 61
<211> LENGTH: 18
<212> TYPE: DNA
<213> ORGANISM: Homo sapiens
<220> FEATURE:
<221> NAME/KEY: CDS
<222> LOCATION: (1)..(18)

<400> SEQUENCE: 61 gag tta cta gtt tgg tac                                        18
Glu Leu Leu Val Trp Tyr
 1               5

<210> SEQ ID NO 62
<211> LENGTH: 6
<212> TYPE: PRT
<213> ORGANISM: Homo sapiens

<400> SEQUENCE: 62

Glu Leu Leu Val Trp Tyr
 1               5

<210> SEQ ID NO 63
<211> LENGTH: 483
<212> TYPE: DNA
<213> ORGANISM: Homo sapiens
<220> FEATURE:
<221> NAME/KEY: CDS
<222> LOCATION: (1)..(483)

<400> SEQUENCE: 63
```

```
tgc tca atg tgc ccc caa gct ttt atc tct cct tcc aaa ctt cat gtc      48
Cys Ser Met Cys Pro Gln Ala Phe Ile Ser Pro Ser Lys Leu His Val
 1               5                  10                  15 tac ttt atg ggt cac atg ggt atg aag ccc cac aag tgt gat ttc tgt      96
Tyr Phe Met Gly His Met Gly Met Lys Pro His Lys Cys Asp Phe Cys
             20                  25                  30 agc aag gct ttt agt gat ccc agc aac ctg cgg acc cac ctc aag ata     144
Ser Lys Ala Phe Ser Asp Pro Ser Asn Leu Arg Thr His Leu Lys Ile
         35                  40                  45 cat aca ggt cag aag aac tac agg tgt acc ttg tgt gac aag tct ttc     192
His Thr Gly Gln Lys Asn Tyr Arg Cys Thr Leu Cys Asp Lys Ser Phe
     50                  55                  60 acc cag aag gct cac ctg gga gtc cac atg gtt atc cac act ggg gag     240
Thr Gln Lys Ala His Leu Gly Val His Met Val Ile His Thr Gly Glu
 65                  70                  75                  80 aag aat ctt aag tgt gat tac tgt gac aag ttg ttt atg cgg agg cag     288
Lys Asn Leu Lys Cys Asp Tyr Cys Asp Lys Leu Phe Met Arg Arg Gln
                 85                  90                  95 gac ctc aag cag cac gtg ctc atc cac act caa gaa cgc cag atc aag     336
Asp Leu Lys Gln His Val Leu Ile His Thr Gln Glu Arg Gln Ile Lys
             100                 105                 110 tgt ccc aag tgt gat aag ctg ttc ttg aga aca aat cac tta aag aag     384
Cys Pro Lys Cys Asp Lys Leu Phe Leu Arg Thr Asn His Leu Lys Lys
         115                 120                 125 cat ctc aat tct cat gaa gga aaa cgg gat tat gtc tgt gaa aaa tgt     432
His Leu Asn Ser His Glu Gly Lys Arg Asp Tyr Val Cys Glu Lys Cys
     130                 135                 140 aca aag gct tat cta acc aaa tac cat ctc acc cgc cac ctg aaa acc     480
Thr Lys Ala Tyr Leu Thr Lys Tyr His Leu Thr Arg His Leu Lys Thr
145                 150                 155                 160 tgc                                                                  483
Cys

<210> SEQ ID NO 64
<211> LENGTH: 161
<212> TYPE: PRT
<213> ORGANISM: Homo sapiens

<400> SEQUENCE: 64

Cys Ser Met Cys Pro Gln Ala Phe Ile Ser Pro Ser Lys Leu His Val
 1               5                  10                  15

Tyr Phe Met Gly His Met Gly Met Lys Pro His Lys Cys Asp Phe Cys
             20                  25                  30

Ser Lys Ala Phe Ser Asp Pro Ser Asn Leu Arg Thr His Leu Lys Ile
         35                  40                  45

His Thr Gly Gln Lys Asn Tyr Arg Cys Thr Leu Cys Asp Lys Ser Phe
     50                  55                  60

Thr Gln Lys Ala His Leu Gly Val His Met Val Ile His Thr Gly Glu
 65                  70                  75                  80

Lys Asn Leu Lys Cys Asp Tyr Cys Asp Lys Leu Phe Met Arg Arg Gln
                 85                  90                  95

Asp Leu Lys Gln His Val Leu Ile His Thr Gln Glu Arg Gln Ile Lys
             100                 105                 110

Cys Pro Lys Cys Asp Lys Leu Phe Leu Arg Thr Asn His Leu Lys Lys
         115                 120                 125

His Leu Asn Ser His Glu Gly Lys Arg Asp Tyr Val Cys Glu Lys Cys
     130                 135                 140
```

```
Thr Lys Ala Tyr Leu Thr Lys Tyr His Leu Thr Arg His Leu Lys Thr
145                 150                 155                 160

Cys

<210> SEQ ID NO 65
<211> LENGTH: 525
<212> TYPE: DNA
<213> ORGANISM: Homo sapiens
<220> FEATURE:
<221> NAME/KEY: CDS
<222> LOCATION: (1)..(525)

<400> SEQUENCE: 65 tgt cct caa tgt gaa tcg agt ttt acc agt gag gat att ctt gct gag      48
Cys Pro Gln Cys Glu Ser Ser Phe Thr Ser Glu Asp Ile Leu Ala Glu
 1               5                  10                  15 cat ctc cag aca ttg cac cag aaa ccc aca gag gag aaa gaa ttt aag      96
His Leu Gln Thr Leu His Gln Lys Pro Thr Glu Glu Lys Glu Phe Lys
             20                  25                  30 tgc aag aac tgt ggg aag aaa ttc cca gtt aag cag gct ttg caa aga     144
Cys Lys Asn Cys Gly Lys Lys Phe Pro Val Lys Gln Ala Leu Gln Arg
         35                  40                  45 cat gtt ctt cag tgc aca gcg aaa agc agt ctg aag gag tct tcg cga     192
His Val Leu Gln Cys Thr Ala Lys Ser Ser Leu Lys Glu Ser Ser Arg
     50                  55                  60 agt ttt cag tgc tct gtt tgc aat tct tcc ttc agt tca gca tcg agt     240
Ser Phe Gln Cys Ser Val Cys Asn Ser Ser Phe Ser Ser Ala Ser Ser
 65                  70                  75                  80 ttt gag cag cac cag gag act tgc cgg ggg gat gcc aag ttt gtg tgc     288
Phe Glu Gln His Gln Glu Thr Cys Arg Gly Asp Ala Lys Phe Val Cys
                 85                  90                  95 aag gct gac agc tgt gga aag agg ctg aag agc aag gat gcc ctg aaa     336
Lys Ala Asp Ser Cys Gly Lys Arg Leu Lys Ser Lys Asp Ala Leu Lys
            100                 105                 110 aga cac cag gaa aat gtc cac act gga gat cct aag aaa aag ctt ata     384
Arg His Gln Glu Asn Val His Thr Gly Asp Pro Lys Lys Lys Leu Ile
        115                 120                 125 tgt tca gtg tgc aat aaa aag tgt tct tca gca tca agc cta cag gaa     432
Cys Ser Val Cys Asn Lys Lys Cys Ser Ser Ala Ser Ser Leu Gln Glu
    130                 135                 140 cat aga aag att cat gag ata ttt gat tgt caa gaa tgt atg aag aaa     480
His Arg Lys Ile His Glu Ile Phe Asp Cys Gln Glu Cys Met Lys Lys
145                 150                 155                 160 ttt att tca gct aat cag cta aaa cgt cat atg atc acc tcg tgc         525
Phe Ile Ser Ala Asn Gln Leu Lys Arg His Met Ile Thr Ser Cys
                165                 170                 175

<210> SEQ ID NO 66
<211> LENGTH: 175
<212> TYPE: PRT
<213> ORGANISM: Homo sapiens

<400> SEQUENCE: 66

Cys Pro Gln Cys Glu Ser Ser Phe Thr Ser Glu Asp Ile Leu Ala Glu
 1               5                  10                  15

His Leu Gln Thr Leu His Gln Lys Pro Thr Glu Glu Lys Glu Phe Lys
             20                  25                  30

Cys Lys Asn Cys Gly Lys Lys Phe Pro Val Lys Gln Ala Leu Gln Arg
         35                  40                  45

His Val Leu Gln Cys Thr Ala Lys Ser Ser Leu Lys Glu Ser Ser Arg
     50                  55                  60
```

```
Ser Phe Gln Cys Ser Val Cys Asn Ser Ser Phe Ser Ser Ala Ser Ser
 65                  70                  75                  80

Phe Glu Gln His Gln Glu Thr Cys Arg Gly Asp Ala Lys Phe Val Cys
                 85                  90                  95

Lys Ala Asp Ser Cys Gly Lys Arg Leu Lys Ser Lys Asp Ala Leu Lys
            100                 105                 110

Arg His Gln Glu Asn Val His Thr Gly Asp Pro Lys Lys Lys Leu Ile
        115                 120                 125

Cys Ser Val Cys Asn Lys Lys Cys Ser Ser Ala Ser Ser Leu Gln Glu
    130                 135                 140

His Arg Lys Ile His Glu Ile Phe Asp Cys Gln Glu Cys Met Lys Lys
145                 150                 155                 160

Phe Ile Ser Ala Asn Gln Leu Lys Arg His Met Ile Thr Ser Cys
                165                 170                 175

<210> SEQ ID NO 67
<211> LENGTH: 1371
<212> TYPE: DNA
<213> ORGANISM: Mus musculus
<220> FEATURE:
<221> NAME/KEY: CDS
<222> LOCATION: (1)..(1371)

<400> SEQUENCE: 67 tgt cca cag tgt gaa tcg agc ttt ccc agt gag gaa gtc ctt act gag      48
Cys Pro Gln Cys Glu Ser Ser Phe Pro Ser Glu Glu Val Leu Thr Glu
  1               5                  10                  15 cac ctt cag agc ttg cac cag aag ccc aca ggg gag aaa gag ttc aaa      96
His Leu Gln Ser Leu His Gln Lys Pro Thr Gly Glu Lys Glu Phe Lys
             20                  25                  30 tgc gag aac tgc ggg aag aaa ttc cct gtg agg cag gcc ttg cag aga     144
Cys Glu Asn Cys Gly Lys Lys Phe Pro Val Arg Gln Ala Leu Gln Arg
         35                  40                  45 cat gtt ctt cag tgc aca gcg aaa agc agt ctg aag gag tct tcg cga     192
His Val Leu Gln Cys Thr Ala Lys Ser Ser Leu Lys Glu Ser Ser Arg
     50                  55                  60 agt ttt cag tgc tct gtt tgc aat tct tcc ttc agt tca gca tcg agt     240
Ser Phe Gln Cys Ser Val Cys Asn Ser Ser Phe Ser Ser Ala Ser Ser
 65                  70                  75                  80 ttt gag cag cac cag gag act tgc cgg ggg gat gcc aag ttt gtg tgc     288
Phe Glu Gln His Gln Glu Thr Cys Arg Gly Asp Ala Lys Phe Val Cys
                 85                  90                  95 aag gct gac agc tgt gga aag agg ctg aag agc aag gat gcc ctg aaa     336
Lys Ala Asp Ser Cys Gly Lys Arg Leu Lys Ser Lys Asp Ala Leu Lys
            100                 105                 110 aga cac cag gaa aat gtc cac act gga gat cct aag aga aaa ctc ata     384
Arg His Gln Glu Asn Val His Thr Gly Asp Pro Lys Arg Lys Leu Ile
        115                 120                 125 tgc tcg gtg tgc aat aga aaa tgt acc tca gtg tca agc ctg cag gag     432
Cys Ser Val Cys Asn Arg Lys Cys Thr Ser Val Ser Ser Leu Gln Glu
    130                 135                 140 cac agg aag att cat gag ata ttt gat tgt caa gaa tgt atg aaa aag     480
His Arg Lys Ile His Glu Ile Phe Asp Cys Gln Glu Cys Met Lys Lys
145                 150                 155                 160 ttt att tct gct aat cag ctg aag cgt cac atg att acc cac tca gaa     528
Phe Ile Ser Ala Asn Gln Leu Lys Arg His Met Ile Thr His Ser Glu
                165                 170                 175 aag cgg cct tat aac tgt gag atc tgt aac aag tcc ttc aag agg ctc     576
Lys Arg Pro Tyr Asn Cys Glu Ile Cys Asn Lys Ser Phe Lys Arg Leu
```

```
            180                 185                 190
gat caa gtg ggc gcc cac aaa gtg atc cac agt gag gac aaa ccc tac    624
Asp Gln Val Gly Ala His Lys Val Ile His Ser Glu Asp Lys Pro Tyr
        195                 200                 205 cag tgc aag ctc tgt ggc aag ggc ttt gct cac aga aac gtt tac aag    672
Gln Cys Lys Leu Cys Gly Lys Gly Phe Ala His Arg Asn Val Tyr Lys
    210                 215                 220 aac cac aag aag acc cac tcc gag gag aga cct ttc cag tgt gat gca    720
Asn His Lys Lys Thr His Ser Glu Glu Arg Pro Phe Gln Cys Asp Ala
225                 230                 235                 240 tgt aaa gcc ttg ttc cgc acg ccc ttt tct ctg cag aga cac ctg tta    768
Cys Lys Ala Leu Phe Arg Thr Pro Phe Ser Leu Gln Arg His Leu Leu
                245                 250                 255 atc cac aac agt gag agg act ttt aag tgt cac cac tgt gat gcc aca    816
Ile His Asn Ser Glu Arg Thr Phe Lys Cys His His Cys Asp Ala Thr
            260                 265                 270 ttt aaa agg aag gat aca tta aac gtt cat gcc cag gtg gtc cat gaa    864
Phe Lys Arg Lys Asp Thr Leu Asn Val His Ala Gln Val Val His Glu
        275                 280                 285 aga cac aag aag tac cga tgt gag ctg tgc aat aag gcc ttt gtc aca    912
Arg His Lys Lys Tyr Arg Cys Glu Leu Cys Asn Lys Ala Phe Val Thr
    290                 295                 300 cct tca gtg ctt agg agt cat aag aag tca cac aca gga gaa aag gag    960
Pro Ser Val Leu Arg Ser His Lys Lys Ser His Thr Gly Glu Lys Glu
305                 310                 315                 320 aaa gtc tgc cca tat tgt ggc cag aaa ttt gcc agc agt ggg acc ctg   1008
Lys Val Cys Pro Tyr Cys Gly Gln Lys Phe Ala Ser Ser Gly Thr Leu
                325                 330                 335 aga gtt cac atc cgg agc cac aca ggt gag cgc ccc tat caa tgc ccg   1056
Arg Val His Ile Arg Ser His Thr Gly Glu Arg Pro Tyr Gln Cys Pro
            340                 345                 350 tac tgt gaa aaa ggt ttc agt aaa aat gac gga ctg aag atg cac att   1104
Tyr Cys Glu Lys Gly Phe Ser Lys Asn Asp Gly Leu Lys Met His Ile
        355                 360                 365 cgt act cac acc agg gag aag ccc tac cag tgc tca gag tgc agc aag   1152
Arg Thr His Thr Arg Glu Lys Pro Tyr Gln Cys Ser Glu Cys Ser Lys
    370                 375                 380 gcc ttc agc cag aag cgg ggc ctc gat gaa cac aag agg aca cac aca   1200
Ala Phe Ser Gln Lys Arg Gly Leu Asp Glu His Lys Arg Thr His Thr
385                 390                 395                 400 gga gaa aag cct ttt cag tgt gac gta tgt gac ttg gct ttt agc ctg   1248
Gly Glu Lys Pro Phe Gln Cys Asp Val Cys Asp Leu Ala Phe Ser Leu
                405                 410                 415 aag aaa atg ctt att cga cac aag atg aca cac aat cct aac cgt ccg   1296
Lys Lys Met Leu Ile Arg His Lys Met Thr His Asn Pro Asn Arg Pro
            420                 425                 430 atg gca gag tgc cat ttc tgc cat aag aag ttt aca aga aat gac tac   1344
Met Ala Glu Cys His Phe Cys His Lys Lys Phe Thr Arg Asn Asp Tyr
        435                 440                 445 ctc aaa gtg cac atg gac aac atc cat                                1371
Leu Lys Val His Met Asp Asn Ile His
    450                 455

<210> SEQ ID NO 68
<211> LENGTH: 457
<212> TYPE: PRT
<213> ORGANISM: Mus musculus

<400> SEQUENCE: 68

Cys Pro Gln Cys Glu Ser Ser Phe Pro Ser Glu Glu Val Leu Thr Glu
```

-continued

```
  1               5               10              15
His Leu Gln Ser Leu His Gln Lys Pro Thr Gly Glu Lys Glu Phe Lys
                20                  25                  30
Cys Glu Asn Cys Gly Lys Lys Phe Pro Val Arg Gln Ala Leu Gln Arg
                35                  40                  45
His Val Leu Gln Cys Thr Ala Lys Ser Ser Leu Lys Glu Ser Ser Arg
                50                  55                  60
Ser Phe Gln Cys Ser Val Cys Asn Ser Ser Phe Ser Ser Ala Ser Ser
 65                 70                  75                  80
Phe Glu Gln His Gln Glu Thr Cys Arg Gly Asp Ala Lys Phe Val Cys
                85                  90                  95
Lys Ala Asp Ser Cys Gly Lys Arg Leu Lys Ser Lys Asp Ala Leu Lys
                100                 105                 110
Arg His Gln Glu Asn Val His Thr Gly Asp Pro Lys Arg Lys Leu Ile
                115                 120                 125
Cys Ser Val Cys Asn Arg Lys Cys Thr Ser Val Ser Ser Leu Gln Glu
                130                 135                 140
His Arg Lys Ile His Glu Ile Phe Asp Cys Gln Glu Cys Met Lys Lys
145                 150                 155                 160
Phe Ile Ser Ala Asn Gln Leu Lys Arg His Met Ile Thr His Ser Glu
                165                 170                 175
Lys Arg Pro Tyr Asn Cys Glu Ile Cys Asn Lys Ser Phe Lys Arg Leu
                180                 185                 190
Asp Gln Val Gly Ala His Lys Val Ile His Ser Glu Asp Lys Pro Tyr
                195                 200                 205
Gln Cys Lys Leu Cys Gly Lys Gly Phe Ala His Arg Asn Val Tyr Lys
                210                 215                 220
Asn His Lys Lys Thr His Ser Glu Glu Arg Pro Phe Gln Cys Asp Ala
225                 230                 235                 240
Cys Lys Ala Leu Phe Arg Thr Pro Phe Ser Leu Gln Arg His Leu Leu
                245                 250                 255
Ile His Asn Ser Glu Arg Thr Phe Lys Cys His His Cys Asp Ala Thr
                260                 265                 270
Phe Lys Arg Lys Asp Thr Leu Asn Val His Ala Gln Val Val His Glu
                275                 280                 285
Arg His Lys Lys Tyr Arg Cys Glu Leu Cys Asn Lys Ala Phe Val Thr
                290                 295                 300
Pro Ser Val Leu Arg Ser His Lys Ser His Thr Gly Glu Lys Glu
305                 310                 315                 320
Lys Val Cys Pro Tyr Cys Gly Gln Lys Phe Ala Ser Ser Gly Thr Leu
                325                 330                 335
Arg Val His Ile Arg Ser His Thr Gly Glu Arg Pro Tyr Gln Cys Pro
                340                 345                 350
Tyr Cys Glu Lys Gly Phe Ser Lys Asn Asp Gly Leu Lys Met His Ile
                355                 360                 365
Arg Thr His Thr Arg Glu Lys Pro Tyr Gln Cys Ser Glu Cys Ser Lys
                370                 375                 380
Ala Phe Ser Gln Lys Arg Gly Leu Asp Glu His Lys Arg Thr His Thr
385                 390                 395                 400
Gly Glu Lys Pro Phe Gln Cys Asp Val Cys Asp Leu Ala Phe Ser Leu
                405                 410                 415
Lys Lys Met Leu Ile Arg His Lys Met Thr His Asn Pro Asn Arg Pro
                420                 425                 430
```

```
Met Ala Glu Cys His Phe Cys His Lys Lys Phe Thr Arg Asn Asp Tyr
        435                 440                 445

Leu Lys Val His Met Asp Asn Ile His
    450                 455

<210> SEQ ID NO 69
<211> LENGTH: 315
<212> TYPE: DNA
<213> ORGANISM: Homo sapiens
<220> FEATURE:
<221> NAME/KEY: CDS
<222> LOCATION: (1)..(315)

<400> SEQUENCE: 69 tgt ggg cag tgc ttt aag act ttc acc cag cgg atc ctc tta cag atg        48
Cys Gly Gln Cys Phe Lys Thr Phe Thr Gln Arg Ile Leu Leu Gln Met
  1               5                  10                  15 cac gtg tgc acg cag aac acc gac aga ccc tac caa tgc ggc cac tgc        96
His Val Cys Thr Gln Asn Thr Asp Arg Pro Tyr Gln Cys Gly His Cys
             20                  25                  30 tcc cag tcc ttt tcc cag cct tca gaa ctg agg aac cac gtg gtc act       144
Ser Gln Ser Phe Ser Gln Pro Ser Glu Leu Arg Asn His Val Val Thr
         35                  40                  45 cac tct agt gac cgg cct ttc aag tgc ggc tac tgt ggt cgt gcc ttt       192
His Ser Ser Asp Arg Pro Phe Lys Cys Gly Tyr Cys Gly Arg Ala Phe
     50                  55                  60 gcc ggg gcc acc acc ctc aac aac cac atc cga acc cac act gga gaa       240
Ala Gly Ala Thr Thr Leu Asn Asn His Ile Arg Thr His Thr Gly Glu
 65                  70                  75                  80 aag ccc ttc aag tgc gag agg tgt gag agg agc ttc acg cag gcc acc       288
Lys Pro Phe Lys Cys Glu Arg Cys Glu Arg Ser Phe Thr Gln Ala Thr
                 85                  90                  95 cag ttg agc cga cac cag cgg atg ccc                                   315
Gln Leu Ser Arg His Gln Arg Met Pro
            100                 105

<210> SEQ ID NO 70
<211> LENGTH: 105
<212> TYPE: PRT
<213> ORGANISM: Homo sapiens

<400> SEQUENCE: 70

Cys Gly Gln Cys Phe Lys Thr Phe Thr Gln Arg Ile Leu Leu Gln Met
  1               5                  10                  15

His Val Cys Thr Gln Asn Thr Asp Arg Pro Tyr Gln Cys Gly His Cys
             20                  25                  30

Ser Gln Ser Phe Ser Gln Pro Ser Glu Leu Arg Asn His Val Val Thr
         35                  40                  45

His Ser Ser Asp Arg Pro Phe Lys Cys Gly Tyr Cys Gly Arg Ala Phe
     50                  55                  60

Ala Gly Ala Thr Thr Leu Asn Asn His Ile Arg Thr His Thr Gly Glu
 65                  70                  75                  80

Lys Pro Phe Lys Cys Glu Arg Cys Glu Arg Ser Phe Thr Gln Ala Thr
                 85                  90                  95

Gln Leu Ser Arg His Gln Arg Met Pro
            100                 105

<210> SEQ ID NO 71
<211> LENGTH: 66
<212> TYPE: DNA
```

-continued

<213> ORGANISM: Homo sapiens
<220> FEATURE:
<221> NAME/KEY: CDS
<222> LOCATION: (1)..(66)

<400> SEQUENCE: 71

```
tgt ccc tca tgc tgt ctg gcc ttt tca agt caa aaa ttt ctc agt caa      48
Cys Pro Ser Cys Cys Leu Ala Phe Ser Ser Gln Lys Phe Leu Ser Gln
 1               5                  10                  15 cat gtg gaa cgc aat cac                                              66
His Val Glu Arg Asn His
             20
```

<210> SEQ ID NO 72
<211> LENGTH: 22
<212> TYPE: PRT
<213> ORGANISM: Homo sapiens

<400> SEQUENCE: 72

```
Cys Pro Ser Cys Cys Leu Ala Phe Ser Ser Gln Lys Phe Leu Ser Gln
 1               5                  10                  15

His Val Glu Arg Asn His
             20
```

<210> SEQ ID NO 73
<211> LENGTH: 231
<212> TYPE: DNA
<213> ORGANISM: Homo sapiens
<220> FEATURE:
<221> NAME/KEY: CDS
<222> LOCATION: (1)..(231)

<400> SEQUENCE: 73

```
tat gga gag tgt ggg caa ggt ttc agt gat aag tca gat gtt att aca      48
Tyr Gly Glu Cys Gly Gln Gly Phe Ser Asp Lys Ser Asp Val Ile Thr
 1               5                  10                  15 cac caa agg aca cac aca ggg ggg aag ccc tac gtc tgc aga gag tgt      96
His Gln Arg Thr His Thr Gly Gly Lys Pro Tyr Val Cys Arg Glu Cys
                 20                  25                  30 ggg gag ggc ttt agc cgg aag tca gac ctc ctc agt cac cag agg aca     144
Gly Glu Gly Phe Ser Arg Lys Ser Asp Leu Leu Ser His Gln Arg Thr
             35                  40                  45 cac aca ggg gag aag cct tat gtc tgc aga gag tgt gag cgg ggc ttt     192
His Thr Gly Glu Lys Pro Tyr Val Cys Arg Glu Cys Glu Arg Gly Phe
         50                  55                  60 agc cgg aag tca gtc ctc ctc att cac cag agg aca cac                 231
Ser Arg Lys Ser Val Leu Leu Ile His Gln Arg Thr His
 65                  70                  75
```

<210> SEQ ID NO 74
<211> LENGTH: 77
<212> TYPE: PRT
<213> ORGANISM: Homo sapiens

<400> SEQUENCE: 74

```
Tyr Gly Glu Cys Gly Gln Gly Phe Ser Asp Lys Ser Asp Val Ile Thr
 1               5                  10                  15

His Gln Arg Thr His Thr Gly Gly Lys Pro Tyr Val Cys Arg Glu Cys
                 20                  25                  30

Gly Glu Gly Phe Ser Arg Lys Ser Asp Leu Leu Ser His Gln Arg Thr
             35                  40                  45

His Thr Gly Glu Lys Pro Tyr Val Cys Arg Glu Cys Glu Arg Gly Phe
         50                  55                  60
```

Ser Arg Lys Ser Val Leu Leu Ile His Gln Arg Thr His
 65                  70                  75

<210> SEQ ID NO 75
<211> LENGTH: 66
<212> TYPE: DNA
<213> ORGANISM: Homo sapiens
<220> FEATURE:
<221> NAME/KEY: CDS
<222> LOCATION: (1)..(66)

<400> SEQUENCE: 75 tgc ctg gaa tgc agc caa cgt ttc cag ttt gag ttc ccc tat gtg gcg      48
Cys Leu Glu Cys Ser Gln Arg Phe Gln Phe Glu Phe Pro Tyr Val Ala
 1               5                  10                  15 cat ctg cgt ttc cgc tgc                                              66
His Leu Arg Phe Arg Cys
            20

<210> SEQ ID NO 76
<211> LENGTH: 22
<212> TYPE: PRT
<213> ORGANISM: Homo sapiens

<400> SEQUENCE: 76

Cys Leu Glu Cys Ser Gln Arg Phe Gln Phe Glu Phe Pro Tyr Val Ala
 1               5                  10                  15

His Leu Arg Phe Arg Cys
            20

<210> SEQ ID NO 77
<211> LENGTH: 1836
<212> TYPE: DNA
<213> ORGANISM: Homo sapiens
<220> FEATURE:
<221> NAME/KEY: CDS
<222> LOCATION: (31)..(1659)

<400> SEQUENCE: 77
actgcgtgag tgcaacactg tccctggtga gca tgc ctg ggt ttt gtg tta cag     54
                                  Ala Cys Leu Gly Phe Val Leu Gln
                                   1               5 gct ttc ttg gca ttt ggg gat gtc act gtg gat ttc acc cag aag gaa     102
Ala Phe Leu Ala Phe Gly Asp Val Thr Val Asp Phe Thr Gln Lys Glu
         10                  15                  20 tgg agg ctg ctg agc cct gct cag agg gcc ctg tac agg gag gtg aca     150
Trp Arg Leu Leu Ser Pro Ala Gln Arg Ala Leu Tyr Arg Glu Val Thr
 25                  30                  35                  40 ctg gag aac tac agc cac ctg gtc tca cta gga att ctc cat tct aaa     198
Leu Glu Asn Tyr Ser His Leu Val Ser Leu Gly Ile Leu His Ser Lys
                 45                  50                  55 cca gaa ctc atc agg cgg cta gag caa ggg gaa gtg ccc tgg gga gaa     246
Pro Glu Leu Ile Arg Arg Leu Glu Gln Gly Glu Val Pro Trp Gly Glu
             60                  65                  70 gag aga aga cgc cgg cca ggc ccc tgt gca gaa aga ctt ttc gtt act     294
Glu Arg Arg Arg Arg Pro Gly Pro Cys Ala Glu Arg Leu Phe Val Thr
         75                  80                  85 gat tca gtc tca ttg ttg gtc tat tct cca gga ata tat gca gaa cat     342
Asp Ser Val Ser Leu Leu Val Tyr Ser Pro Gly Ile Tyr Ala Glu His
         90                  95                 100 gtc ctg cgg ccc aag aat ctt gga ctt gca cat cag agg caa cag caa     390
Val Leu Arg Pro Lys Asn Leu Gly Leu Ala His Gln Arg Gln Gln Gln
105                 110                 115                 120

-continued

| | |
|---|---|
| cta caa ttt tct gat caa agc ttc cag agt gac aca gct gaa ggt caa<br>Leu Gln Phe Ser Asp Gln Ser Phe Gln Ser Asp Thr Ala Glu Gly Gln<br>                         125                      130                      135 | 438 |
| gag aaa gaa aaa agc act aag ccc atg gca ttt tcc agc cca ccc cta<br>Glu Lys Glu Lys Ser Thr Lys Pro Met Ala Phe Ser Ser Pro Pro Leu<br>140                      145                      150 | 486 |
| aga cat gca gta agc tca agg agg agg aac agt gta gtg gaa ata gag<br>Arg His Ala Val Ser Ser Arg Arg Arg Asn Ser Val Val Glu Ile Glu<br>                         155                      160                      165 | 534 |
| tct agt caa ggc cag agg gaa aat cct aca gaa ata gac aaa gta ttg<br>Ser Ser Gln Gly Gln Arg Glu Asn Pro Thr Glu Ile Asp Lys Val Leu<br>170                      175                      180 | 582 |
| aaa gga ata gaa aat tca aga tgg gga gca ttc aag tgt gca gag tgt<br>Lys Gly Ile Glu Asn Ser Arg Trp Gly Ala Phe Lys Cys Ala Glu Cys<br>185                      190                      195                      200 | 630 |
| ggg caa gac ttc agc cgg aag atg atg gta atc ata cac aaa aaa gca<br>Gly Gln Asp Phe Ser Arg Lys Met Met Val Ile Ile His Lys Lys Ala<br>                         205                      210                      215 | 678 |
| cat tcc agg cag aaa ctt ttt aca tgc agg gag tgt cac cag ggc ttt<br>His Ser Arg Gln Lys Leu Phe Thr Cys Arg Glu Cys His Gln Gly Phe<br>                      220                      225                      230 | 726 |
| aga gat gag tca gca ttg ctc ttg cac cag aac aca cac aca gga gag<br>Arg Asp Glu Ser Ala Leu Leu Leu His Gln Asn Thr His Thr Gly Glu<br>                235                      240                      245 | 774 |
| aag tcc tat gtg tgc agt gtg tgt ggg cga ggc ttc agc ctc aag gcc<br>Lys Ser Tyr Val Cys Ser Val Cys Gly Arg Gly Phe Ser Leu Lys Ala<br>      250                      255                      260 | 822 |
| aac ctc ctc aga cac cag agg aca cac tca gag gag aag cct tat gga<br>Asn Leu Leu Arg His Gln Arg Thr His Ser Glu Glu Lys Pro Tyr Gly<br>265                      270                      275                      280 | 870 |
| tgt cgg gag tgt ggg cga agg ttt cgg gat aag tcc tcc tat aac aag<br>Cys Arg Glu Cys Gly Arg Arg Phe Arg Asp Lys Ser Ser Tyr Asn Lys<br>                         285                      290                      295 | 918 |
| cac ctg agg gca cac ttg ggt gag aaa cgt ttt ttc tgc agg gat tgt<br>His Leu Arg Ala His Leu Gly Glu Lys Arg Phe Phe Cys Arg Asp Cys<br>300                      305                      310 | 966 |
| ggg cga ggc ttt acc ttg aag cca aat ctc acc ata cat cag agg aca<br>Gly Arg Gly Phe Thr Leu Lys Pro Asn Leu Thr Ile His Gln Arg Thr<br>                315                      320                      325 | 1014 |
| cac tca gga gag aag ccc ttc atg tgc aag cag tgt gag aaa agt ttt<br>His Ser Gly Glu Lys Pro Phe Met Cys Lys Gln Cys Glu Lys Ser Phe<br>330                      335                      340 | 1062 |
| agt ttg aag gca aat ctt ctt aga cat cag tgg aca cac tcg ggg gaa<br>Ser Leu Lys Ala Asn Leu Leu Arg His Gln Trp Thr His Ser Gly Glu<br>345                      350                      355                      360 | 1110 |
| agg cca ttt aat tgc aag gat tgc ggg cga ggc ttc atc cta aaa tca<br>Arg Pro Phe Asn Cys Lys Asp Cys Gly Arg Gly Phe Ile Leu Lys Ser<br>                         365                      370                      375 | 1158 |
| act ctc ctc ttc cac cag aag aca cac tca ggg gag aag cct ttc atc<br>Thr Leu Leu Phe His Gln Lys Thr His Ser Gly Glu Lys Pro Phe Ile<br>                380                      385                      390 | 1206 |
| tgt agt gaa tgt ggg caa gga ttt atc tgg aag tca aat ctt gtg aaa<br>Cys Ser Glu Cys Gly Gln Gly Phe Ile Trp Lys Ser Asn Leu Val Lys<br>      395                      400                      405 | 1254 |
| cac cag ctt gca cat tct ggc aag cag cct ttt gta tgc aag gag tgt<br>His Gln Leu Ala His Ser Gly Lys Gln Pro Phe Val Cys Lys Glu Cys<br>410                      415                      420 | 1302 |
| ggg cga ggc ttc aac tgg aag gga aat ctc ctc aca cac cag agg aca<br>Gly Arg Gly Phe Asn Trp Lys Gly Asn Leu Leu Thr His Gln Arg Thr | 1350 |

```
                425                 430                 435                 440
cac tca ggg gag aag ccc ttc gtg tgt aat gtg tgt ggg caa ggc ttc       1398
His Ser Gly Glu Lys Pro Phe Val Cys Asn Val Cys Gly Gln Gly Phe
                    445                 450                 455 agc tgg aag aga agt ctc acc aga cac cac tgg cgg ata cac tca aag       1446
Ser Trp Lys Arg Ser Leu Thr Arg His His Trp Arg Ile His Ser Lys
460                 465                 470 gag aag cct ttt gtt tgc cag gag tgt aag cga ggc tat acc agt aag       1494
Glu Lys Pro Phe Val Cys Gln Glu Cys Lys Arg Gly Tyr Thr Ser Lys
    475                 480                 485 tca gac ctc act gtg cat gaa aga ata cac aca gga gag agg cct tat       1542
Ser Asp Leu Thr Val His Glu Arg Ile His Thr Gly Glu Arg Pro Tyr
490                 495                 500 gaa tgc caa gag tgt gga cga aag ttt agc aat aag tca tac tac agt       1590
Glu Cys Gln Glu Cys Gly Arg Lys Phe Ser Asn Lys Ser Tyr Tyr Ser
505                 510                 515                 520 aag cac tta aag aga cac tta cgt gag aag cgt ttt tgt aca ggg agt       1638
Lys His Leu Lys Arg His Leu Arg Glu Lys Arg Phe Cys Thr Gly Ser
                    525                 530                 535 gtg ggt gag gct tca tct tga agttatatct caccatccat cagaggacac          1689
Val Gly Glu Ala Ser Ser
                540 actcaggaga gtaactttgc tttgttacaa gctttagttg aggctgcata acttgttcgt    1749 gaagatataa cagaggcaga cagaatccag agggctacag agaacctgaa ttcaacccat    1809 gtgtccccaa gagattcaga gaaaaga                                        1836

<210> SEQ ID NO 78
<211> LENGTH: 542
<212> TYPE: PRT
<213> ORGANISM: Homo sapiens

<400> SEQUENCE: 78

Ala Cys Leu Gly Phe Val Leu Gln Ala Phe Leu Ala Phe Gly Asp Val
 1               5                  10                  15

Thr Val Asp Phe Thr Gln Lys Glu Trp Arg Leu Leu Ser Pro Ala Gln
                20                  25                  30

Arg Ala Leu Tyr Arg Glu Val Thr Leu Glu Asn Tyr Ser His Leu Val
            35                  40                  45

Ser Leu Gly Ile Leu His Ser Lys Pro Glu Leu Ile Arg Arg Leu Glu
        50                  55                  60

Gln Gly Glu Val Pro Trp Gly Glu Arg Arg Arg Pro Gly Pro
 65                 70                  75                  80

Cys Ala Glu Arg Leu Phe Val Thr Asp Ser Val Ser Leu Leu Val Tyr
                85                  90                  95

Ser Pro Gly Ile Tyr Ala Glu His Val Leu Arg Pro Lys Asn Leu Gly
            100                 105                 110

Leu Ala His Gln Arg Gln Gln Leu Gln Phe Ser Asp Gln Ser Phe
        115                 120                 125

Gln Ser Asp Thr Ala Glu Gly Gln Glu Lys Lys Ser Thr Lys Pro
    130                 135                 140

Met Ala Phe Ser Ser Pro Leu Arg His Ala Val Ser Ser Arg Arg
145                 150                 155                 160

Arg Asn Ser Val Val Glu Ile Glu Ser Ser Gln Gly Gln Arg Glu Asn
                165                 170                 175

Pro Thr Glu Ile Asp Lys Val Leu Lys Gly Ile Glu Asn Ser Arg Trp
            180                 185                 190
```

-continued

```
Gly Ala Phe Lys Cys Ala Glu Cys Gly Gln Asp Phe Ser Arg Lys Met
            195                 200                 205

Met Val Ile Ile His Lys Lys Ala His Ser Arg Gln Lys Leu Phe Thr
        210                 215                 220

Cys Arg Glu Cys His Gln Gly Phe Arg Asp Glu Ser Ala Leu Leu Leu
225                 230                 235                 240

His Gln Asn Thr His Thr Gly Glu Lys Ser Tyr Val Cys Ser Val Cys
                245                 250                 255

Gly Arg Gly Phe Ser Leu Lys Ala Asn Leu Leu Arg His Gln Arg Thr
            260                 265                 270

His Ser Glu Glu Lys Pro Tyr Gly Cys Arg Glu Cys Gly Arg Arg Phe
        275                 280                 285

Arg Asp Lys Ser Ser Tyr Asn Lys His Leu Arg Ala His Leu Gly Glu
290                 295                 300

Lys Arg Phe Phe Cys Arg Asp Cys Gly Arg Gly Phe Thr Leu Lys Pro
305                 310                 315                 320

Asn Leu Thr Ile His Gln Arg Thr His Ser Gly Glu Lys Pro Phe Met
                325                 330                 335

Cys Lys Gln Cys Glu Lys Ser Phe Ser Leu Lys Ala Asn Leu Leu Arg
            340                 345                 350

His Gln Trp Thr His Ser Gly Glu Arg Pro Phe Asn Cys Lys Asp Cys
        355                 360                 365

Gly Arg Gly Phe Ile Leu Lys Ser Thr Leu Leu Phe His Gln Lys Thr
370                 375                 380

His Ser Gly Glu Lys Pro Phe Ile Cys Ser Glu Cys Gly Gln Gly Phe
385                 390                 395                 400

Ile Trp Lys Ser Asn Leu Val Lys His Gln Leu Ala His Ser Gly Lys
                405                 410                 415

Gln Pro Phe Val Cys Lys Glu Cys Gly Arg Gly Phe Asn Trp Lys Gly
            420                 425                 430

Asn Leu Leu Thr His Gln Arg Thr His Ser Gly Glu Lys Pro Phe Val
        435                 440                 445

Cys Asn Val Cys Gly Gln Gly Phe Ser Trp Lys Arg Ser Leu Thr Arg
450                 455                 460

His His Trp Arg Ile His Ser Lys Glu Lys Pro Phe Val Cys Gln Glu
465                 470                 475                 480

Cys Lys Arg Gly Tyr Thr Ser Lys Ser Asp Leu Thr Val His Glu Arg
                485                 490                 495

Ile His Thr Gly Glu Arg Pro Tyr Glu Cys Gln Glu Cys Gly Arg Lys
            500                 505                 510

Phe Ser Asn Lys Ser Tyr Tyr Ser Lys His Leu Lys Arg His Leu Arg
        515                 520                 525

Glu Lys Arg Phe Cys Thr Gly Ser Val Gly Glu Ala Ser Ser
530                 535                 540

<210> SEQ ID NO 79
<211> LENGTH: 1970
<212> TYPE: DNA
<213> ORGANISM: Homo sapiens
<220> FEATURE:
<221> NAME/KEY: CDS
<222> LOCATION: (1)..(1596)

<400> SEQUENCE: 79 aca ttc agg gat gtg act gtg atc ttc aca gaa gca gaa tgg aag aga        48
```

```
      Thr Phe Arg Asp Val Thr Val Ile Phe Thr Glu Ala Glu Trp Lys Arg
        1           5                  10                  15 ctg agt cca gag cag agg aat cta tac aaa gaa gtg atg ctg gag aat            96
Leu Ser Pro Glu Gln Arg Asn Leu Tyr Lys Glu Val Met Leu Glu Asn
            20                  25                  30 tac agg aat ctt ctc tca ttg gaa atc tac act tgt tcc tcc tgc ctt           144
Tyr Arg Asn Leu Leu Ser Leu Glu Ile Tyr Thr Cys Ser Ser Cys Leu
                35                  40                  45 ctg gcc ttc tcc tgt cag cag ttc ctc agt caa cat gta ctt cag atc           192
Leu Ala Phe Ser Cys Gln Gln Phe Leu Ser Gln His Val Leu Gln Ile
    50                  55                  60 ttc ctg ggc tta tgt gca gaa aat cac ttc cat cca ggg aat tct agc           240
Phe Leu Gly Leu Cys Ala Glu Asn His Phe His Pro Gly Asn Ser Ser
65                  70                  75                  80 cca ggg cat tgg aaa cag cag ggg cag cag tat tcc cat gta agc tgt           288
Pro Gly His Trp Lys Gln Gln Gly Gln Gln Tyr Ser His Val Ser Cys
                85                  90                  95 tgg ttt gaa aat gca gaa ggt cag gag aga gga ggt ggc tcc aaa ccc           336
Trp Phe Glu Asn Ala Glu Gly Gln Glu Arg Gly Gly Gly Ser Lys Pro
                100                 105                 110 tgg tct gca agg aca gag gag aga gaa acc tca agg gca ttc ccc agc           384
Trp Ser Ala Arg Thr Glu Glu Arg Glu Thr Ser Arg Ala Phe Pro Ser
            115                 120                 125 cca ctc caa aga cag tca gca agt cct aga aaa ggc aac atg gtg gta           432
Pro Leu Gln Arg Gln Ser Ala Ser Pro Arg Lys Gly Asn Met Val Val
130                 135                 140 gaa aca gag ccc agc tca gcc caa aga cca aac cct gtg cag cta gac           480
Glu Thr Glu Pro Ser Ser Ala Gln Arg Pro Asn Pro Val Gln Leu Asp
145                 150                 155                 160 aaa ggc ttg aag gaa tta gaa acc ttg aga ttt gga gca atc aac tgt           528
Lys Gly Leu Lys Glu Leu Glu Thr Leu Arg Phe Gly Ala Ile Asn Cys
                165                 170                 175 aga gag tat gaa ccg gac cat aac ctg gaa tca aac ttt att aca aac           576
Arg Glu Tyr Glu Pro Asp His Asn Leu Glu Ser Asn Phe Ile Thr Asn
            180                 185                 190 ccg agg acc ctc tta ggg aag aag ccc tac att tgc agt gat tgt ggg           624
Pro Arg Thr Leu Leu Gly Lys Lys Pro Tyr Ile Cys Ser Asp Cys Gly
            195                 200                 205 cga agc ttt aaa gat aga tca acc ctc atc aga cac cat cgt ata cac           672
Arg Ser Phe Lys Asp Arg Ser Thr Leu Ile Arg His His Arg Ile His
        210                 215                 220 tcg atg gag aag cct tat gtg tgc agt gag tgc ggg cga ggt ttt agc           720
Ser Met Glu Lys Pro Tyr Val Cys Ser Glu Cys Gly Arg Gly Phe Ser
225                 230                 235                 240 cag aag tcc aac ctc agc aga cac cag aga aca cat tca gaa gag aag           768
Gln Lys Ser Asn Leu Ser Arg His Gln Arg Thr His Ser Glu Glu Lys
                245                 250                 255 cct tat ttg tgc agg gag tgt ggg caa agc ttt aga agt aag tcc atc           816
Pro Tyr Leu Cys Arg Glu Cys Gly Gln Ser Phe Arg Ser Lys Ser Ile
            260                 265                 270 ctc aat aga cat cag tgg act cac tca gag gag aag ccc tat gtt tgc           864
Leu Asn Arg His Gln Trp Thr His Ser Glu Glu Lys Pro Tyr Val Cys
        275                 280                 285 agc gag tgt ggg cga ggc ttt agc gag aag tca tcc ttc atc aga cac           912
Ser Glu Cys Gly Arg Gly Phe Ser Glu Lys Ser Ser Phe Ile Arg His
        290                 295                 300 cag agg aca cac tcc ggt gag aaa ccc tat gtg tgc ctg gag tgt gga           960
Gln Arg Thr His Ser Gly Glu Lys Pro Tyr Val Cys Leu Glu Cys Gly
305                 310                 315                 320
```

```
cga agc ttt tgt gat aag tca acc ctc aga aaa cac cag agg ata cac       1008
Arg Ser Phe Cys Asp Lys Ser Thr Leu Arg Lys His Gln Arg Ile His
            325                 330                 335 tca ggg gag aag cct tat gtt tgc agg gag tgt ggg cga ggc ttt agc       1056
Ser Gly Glu Lys Pro Tyr Val Cys Arg Glu Cys Gly Arg Gly Phe Ser
        340                 345                 350 cag aac tca gat ctc atc aaa cac cag agg aca cac ttg gat gag aag       1104
Gln Asn Ser Asp Leu Ile Lys His Gln Arg Thr His Leu Asp Glu Lys
    355                 360                 365 cct tat gtt tgc agg gag tgt ggg cga ggc ttt tgt gac aag tca acc       1152
Pro Tyr Val Cys Arg Glu Cys Gly Arg Gly Phe Cys Asp Lys Ser Thr
370                 375                 380 ctc atc ata cac gag cgg acg cac tct gga gag aag cct tat gtg tgt       1200
Leu Ile Ile His Glu Arg Thr His Ser Gly Glu Lys Pro Tyr Val Cys
385                 390                 395                 400 ggt gag tgt ggc cga ggc ttt agt cgg aaa tca ctc ctc ctt gtc cac       1248
Gly Glu Cys Gly Arg Gly Phe Ser Arg Lys Ser Leu Leu Leu Val His
            405                 410                 415 cag agg aca cac tca ggg gag aag cat tat gtc tgc agg gag tgt agg       1296
Gln Arg Thr His Ser Gly Glu Lys His Tyr Val Cys Arg Glu Cys Arg
        420                 425                 430 cga ggt ttt agc cag aag tca aat ctc atc aga cac cag agg acg cac       1344
Arg Gly Phe Ser Gln Lys Ser Asn Leu Ile Arg His Gln Arg Thr His
    435                 440                 445 tca aat gag aag cct tat att tgc agg gaa tgt ggg cga ggc ttt tgt       1392
Ser Asn Glu Lys Pro Tyr Ile Cys Arg Glu Cys Gly Arg Gly Phe Cys
450                 455                 460 gac aag tca acc ctc att gta cat gag agg aca cac tca gga gag aag       1440
Asp Lys Ser Thr Leu Ile Val His Glu Arg Thr His Ser Gly Glu Lys
465                 470                 475                 480 cct tac gtg tgc agt gag tgt ggc cga ggc ttt agc cgg aaa tca ctc       1488
Pro Tyr Val Cys Ser Glu Cys Gly Arg Gly Phe Ser Arg Lys Ser Leu
            485                 490                 495 ctc ctt gtc cac cag agg aca cac tca ggg gag aag cat tat gtt tgt       1536
Leu Leu Val His Gln Arg Thr His Ser Gly Glu Lys His Tyr Val Cys
        500                 505                 510 agg gag tgt ggg cga ggc ttt agt cat aag tca aat ctc atc aga cac       1584
Arg Glu Cys Gly Arg Gly Phe Ser His Lys Ser Asn Leu Ile Arg His
    515                 520                 525 cag agg aca cac tgacgggaga aacctgtgta tgcaggggtc atgaacaaga           1636
Gln Arg Thr His
530 cctgagtgac cagtcaagcc tcatgttacc ccagagagac acatggggag tagaccctgt     1696 gtacacagat tgtgagtgaa gttccagaga tgtgtcagcc cttatcaggc atgggaggga     1756 cacgttcagg agaggagcct tatgagtata gagtacgggc aactgtagcc atcagtcagc     1816 cttgagcatg cacaaaagga cacacttagg agagaagttt atgtgtaggg actgtgggaa     1876 ggctttagca ataatcaaca tttaccagac atccaatgac agcctcaggg gaaagcaccc     1936 ttgtctgggg agtgttgggg agcatcagta aaag                                 1970
```

<210> SEQ ID NO 80
<211> LENGTH: 532
<212> TYPE: PRT
<213> ORGANISM: Homo sapiens

<400> SEQUENCE: 80

Thr Phe Arg Asp Val Thr Val Ile Phe Thr Glu Ala Glu Trp Lys Arg
 1               5                   10                  15

-continued

```
Leu Ser Pro Glu Gln Arg Asn Leu Tyr Lys Glu Val Met Leu Glu Asn
             20                  25                  30
Tyr Arg Asn Leu Leu Ser Leu Glu Ile Tyr Thr Cys Ser Ser Cys Leu
         35                  40                  45
Leu Ala Phe Ser Cys Gln Gln Phe Leu Ser Gln His Val Leu Gln Ile
     50                  55                  60
Phe Leu Gly Leu Cys Ala Glu Asn His Phe His Pro Gly Asn Ser Ser
 65                  70                  75                  80
Pro Gly His Trp Lys Gln Gln Gly Gln Tyr Ser His Val Ser Cys
                 85                  90                  95
Trp Phe Glu Asn Ala Glu Gly Gln Glu Arg Gly Gly Ser Lys Pro
                100                 105                 110
Trp Ser Ala Arg Thr Glu Glu Arg Glu Thr Ser Arg Ala Phe Pro Ser
             115                 120                 125
Pro Leu Gln Arg Gln Ser Ala Ser Pro Arg Lys Gly Asn Met Val Val
     130                 135                 140
Glu Thr Glu Pro Ser Ser Ala Gln Arg Pro Asn Pro Val Gln Leu Asp
145                 150                 155                 160
Lys Gly Leu Lys Glu Leu Glu Thr Leu Arg Phe Gly Ala Ile Asn Cys
                 165                 170                 175
Arg Glu Tyr Glu Pro Asp His Asn Leu Glu Ser Asn Phe Ile Thr Asn
             180                 185                 190
Pro Arg Thr Leu Leu Gly Lys Lys Pro Tyr Ile Cys Ser Asp Cys Gly
         195                 200                 205
Arg Ser Phe Lys Asp Arg Ser Thr Leu Ile Arg His His Arg Ile His
     210                 215                 220
Ser Met Glu Lys Pro Tyr Val Cys Ser Glu Cys Gly Arg Gly Phe Ser
225                 230                 235                 240
Gln Lys Ser Asn Leu Ser Arg His Gln Arg Thr His Ser Glu Glu Lys
                 245                 250                 255
Pro Tyr Leu Cys Arg Glu Cys Gly Gln Ser Phe Arg Ser Lys Ser Ile
             260                 265                 270
Leu Asn Arg His Gln Trp Thr His Ser Glu Glu Lys Pro Tyr Val Cys
         275                 280                 285
Ser Glu Cys Gly Arg Gly Phe Ser Glu Lys Ser Ser Phe Ile Arg His
     290                 295                 300
Gln Arg Thr His Ser Gly Glu Lys Pro Tyr Val Cys Leu Glu Cys Gly
305                 310                 315                 320
Arg Ser Phe Cys Asp Lys Ser Thr Leu Arg Lys His Gln Arg Ile His
                 325                 330                 335
Ser Gly Glu Lys Pro Tyr Val Cys Arg Glu Cys Gly Arg Gly Phe Ser
             340                 345                 350
Gln Asn Ser Asp Leu Ile Lys His Gln Arg Thr His Leu Asp Glu Lys
         355                 360                 365
Pro Tyr Val Cys Arg Glu Cys Gly Arg Gly Phe Cys Asp Lys Ser Thr
     370                 375                 380
Leu Ile Ile His Glu Arg Thr His Ser Gly Glu Lys Pro Tyr Val Cys
385                 390                 395                 400
Gly Glu Cys Gly Arg Gly Phe Ser Arg Lys Ser Leu Leu Leu Val His
                 405                 410                 415
Gln Arg Thr His Ser Gly Glu Lys His Tyr Val Cys Arg Glu Cys Arg
             420                 425                 430
Arg Gly Phe Ser Gln Lys Ser Asn Leu Ile Arg His Gln Arg Thr His
```

```
                  435                 440                 445
Ser Asn Glu Lys Pro Tyr Ile Cys Arg Glu Cys Gly Arg Gly Phe Cys
    450                 455                 460

Asp Lys Ser Thr Leu Ile Val His Glu Arg Thr His Ser Gly Glu Lys
465                 470                 475                 480

Pro Tyr Val Cys Ser Glu Cys Gly Arg Gly Phe Ser Arg Lys Ser Leu
                485                 490                 495

Leu Leu Val His Gln Arg Thr His Ser Gly Glu Lys His Tyr Val Cys
            500                 505                 510

Arg Glu Cys Gly Arg Gly Phe Ser His Lys Ser Asn Leu Ile Arg His
        515                 520                 525

Gln Arg Thr His
    530

<210> SEQ ID NO 81
<211> LENGTH: 21
<212> TYPE: DNA
<213> ORGANISM: Homo sapiens

<400> SEQUENCE: 81
ggtgaaaagt tcggaccctt t                                        21

<210> SEQ ID NO 82
<211> LENGTH: 21
<212> TYPE: DNA
<213> ORGANISM: Homo sapiens

<400> SEQUENCE: 82
tgcccgctgt tgattgtctt c                                        21

<210> SEQ ID NO 83
<211> LENGTH: 22
<212> TYPE: DNA
<213> ORGANISM: Homo sapiens

<400> SEQUENCE: 83
gctgcctgaa agtcttaaag ca                                       22

<210> SEQ ID NO 84
<211> LENGTH: 23
<212> TYPE: DNA
<213> ORGANISM: Homo sapiens

<400> SEQUENCE: 84
cagcaaggca cctggattgg acc                                      23

<210> SEQ ID NO 85
<211> LENGTH: 21
<212> TYPE: DNA
<213> ORGANISM: Homo sapiens

<400> SEQUENCE: 85
aacggacagc tgttctaccg c                                        21

<210> SEQ ID NO 86
<211> LENGTH: 21
<212> TYPE: DNA
<213> ORGANISM: Homo sapiens

<400> SEQUENCE: 86
aagtctcttg gggcagcgga a                                        21
```

<210> SEQ ID NO 87
<211> LENGTH: 20
<212> TYPE: DNA
<213> ORGANISM: Homo sapiens

<400> SEQUENCE: 87 gaat ttcctctttg                                                      20

<210> SEQ ID NO 88
<211> LENGTH: 15
<212> TYPE: DNA
<213> ORGANISM: Homo sapiens
<220> FEATURE:
<221> NAME/KEY: CDS
<222> LOCATION: (1)..(15)

<400> SEQUENCE: 88 ctt ggc tgt aaa gag                                                  15
Leu Gly Cys Lys Glu
  1               5

<210> SEQ ID NO 89
<211> LENGTH: 5
<212> TYPE: PRT
<213> ORGANISM: Homo sapiens

<400> SEQUENCE: 89

Leu Gly Cys Lys Glu
  1               5

<210> SEQ ID NO 90
<211> LENGTH: 15
<212> TYPE: DNA
<213> ORGANISM: Mus musculus
<220> FEATURE:
<221> NAME/KEY: CDS
<222> LOCATION: (1)..(15)

<400> SEQUENCE: 90 ctt ggc tgt gaa gag                                                  15
Leu Gly Cys Glu Glu
  1               5

<210> SEQ ID NO 91
<211> LENGTH: 5
<212> TYPE: PRT
<213> ORGANISM: Mus musculus

<400> SEQUENCE: 91

Leu Gly Cys Glu Glu
  1               5

<210> SEQ ID NO 92
<211> LENGTH: 9
<212> TYPE: PRT
<213> ORGANISM: Homo sapiens

<400> SEQUENCE: 92

Asp Arg Leu Gly Cys Lys Glu Asp Tyr
  1               5

<210> SEQ ID NO 93
<211> LENGTH: 9
<212> TYPE: PRT
<213> ORGANISM: Mus musculus

-continued

```
<400> SEQUENCE: 93

Gly His Leu Gly Cys Glu Glu Asp Phe
 1               5
```